United States Patent
Asokan et al.

(10) Patent No.: US 10,907,176 B2
(45) Date of Patent: Feb. 2, 2021

(54) METHODS AND COMPOSITIONS FOR TARGETED GENE TRANSFER

(71) Applicant: The University of North Carolina at Chapel Hill, Chapel Hill, NC (US)

(72) Inventors: Aravind Asokan, Chapel Hill, NC (US); Giridhar Murlidharan, Carrboro, NC (US); Shen Shen, Watertown, MA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 607 days.

(21) Appl. No.: 15/543,536

(22) PCT Filed: Jan. 14, 2016

(86) PCT No.: PCT/US2016/013460
§ 371 (c)(1),
(2) Date: Jul. 13, 2017

(87) PCT Pub. No.: WO2016/115382
PCT Pub. Date: Jul. 21, 2016

(65) Prior Publication Data
US 2018/0002722 A1    Jan. 4, 2018

Related U.S. Application Data

(60) Provisional application No. 62/103,462, filed on Jan. 14, 2015.

(51) Int. Cl.
| | | |
|---|---|---|
| C12N 15/86 | (2006.01) | |
| C12N 5/10 | (2006.01) | |
| A61K 31/7088 | (2006.01) | |
| C07K 14/005 | (2006.01) | |
| A61K 48/00 | (2006.01) | |
| C12N 7/00 | (2006.01) | |

(52) U.S. Cl.
CPC .......... *C12N 15/86* (2013.01); *A61K 31/7088* (2013.01); *C07K 14/005* (2013.01); *C12N 5/10* (2013.01); *A61K 48/00* (2013.01); *C12N 7/00* (2013.01); *C12N 2510/00* (2013.01); *C12N 2750/14122* (2013.01); *C12N 2750/14145* (2013.01)

(58) Field of Classification Search
None
See application file for complete search history.

(56) References Cited

U.S. PATENT DOCUMENTS

| | | | |
|---|---|---|---|
| 5,399,346 A | 3/1995 | Anderson et al. | |
| 5,478,745 A | 12/1995 | Samulski et al. | |
| 5,863,541 A | 1/1999 | Samulski et al. | |
| 5,869,248 A | 2/1999 | Yuan et al. | |
| 5,877,022 A | 3/1999 | Stinchcomb et al. | |
| 5,882,652 A | 3/1999 | Valdes et al. | |
| 5,905,040 A | 5/1999 | Mazzara et al. | |
| 5,916,563 A | 6/1999 | Young et al. | |
| 6,013,487 A | 1/2000 | Mitchell | |
| 6,040,183 A | 3/2000 | Ferrari et al. | |
| 6,083,702 A | 7/2000 | Mitchell et al. | |
| 6,093,570 A | 7/2000 | Ferrari et al. | |
| 6,156,303 A | 12/2000 | Russell et al. | |
| 6,468,524 B1 | 10/2002 | Chiorini et al. | |
| 6,822,071 B1 | 11/2004 | Stephens et al. | |
| 7,071,172 B2 | 7/2006 | McCown et al. | |
| 7,201,898 B2 | 4/2007 | Monahan et al. | |
| 7,749,492 B2 | 7/2010 | Bartlett et al. | |
| 9,683,268 B2 * | 6/2017 | Barouch | C12N 7/00 |
| 2003/0017131 A1 | 1/2003 | Park et al. | |
| 2004/0013645 A1 | 1/2004 | Monahan et al. | |

FOREIGN PATENT DOCUMENTS

| | | |
|---|---|---|
| WO | WO 90/05142 A1 | 5/1990 |
| WO | WO 98/11244 A2 | 3/1998 |
| WO | WO 99/61601 A2 | 12/1999 |
| WO | WO 00/02806 A1 | 1/2000 |
| WO | WO 00/17377 A2 | 3/2000 |
| WO | WO 00/28004 A1 | 5/2000 |
| WO | WO 01/92551 A2 | 12/2001 |
| WO | WO 03/095647 A2 | 11/2003 |
| WO | WO 2006/021724 A2 | 3/2006 |
| WO | WO 2006/029319 A2 | 3/2006 |
| WO | WO 2006/066066 A2 | 6/2006 |
| WO | WO 2006/073052 A1 | 7/2006 |
| WO | WO 2006/119137 A1 | 11/2006 |
| WO | WO 2007/100465 A2 | 9/2007 |
| WO | WO 2008/088895 A2 | 7/2008 |
| WO | WO 2013/190059 A1 | 12/2013 |

OTHER PUBLICATIONS

Extended European Search Report corresponding to European Patent Application No. 16737901.5 (6 pages) (dated May 15, 2018).
Huang et al. "Parvovirus glycan interactions" *Current Opinion in Virology* 7:108-118 (2014).
Murlidharan et al. "265. Polysialic Acid as a Novel Regulator of AAV Tropism in the Developing Brain" *Molecular Therapy* 23(Supplement 1):S106 (2015).
Murlidharan et al. "Unique Glycan Signatures Regulate Adeno-Associated Virus Tropism in the Developing Brain" *Journal of Virology* 89(7):3976-3987 (2015).
Agbandje et al. "The Structure of Human Parvovirus B19 at 8 Å; Resolution" *Virology* 203(1):106-115 (1994) (Abstract only).
Altschul et al. "Basic Local Alignment Search Tool" *Journal of Molecular Biology* 215:403-410 (1990).
Altschul et al. "Local Alignment Statistics" *Methods in Enzymology* 266:460-480 (1996).

(Continued)

*Primary Examiner* — James D Schultz
(74) *Attorney, Agent, or Firm* — Myers Bigel, P.A.

(57) ABSTRACT

The present invention provides AAV capsid proteins comprising a modification in the amino acid sequence and virus capsids and virus vectors comprising the modified AAV capsid protein. The invention also provides methods of administering the virus vectors and virus capsids of the invention to a cell or to a subject in vivo.

39 Claims, 5 Drawing Sheets
Specification includes a Sequence Listing.

(56) References Cited

OTHER PUBLICATIONS

Altschul et al. "Gapped BLAST and PSI-BLAST: a new generation of protein database search programs" *Nucleic Acids Research* 25(17):3389-3402 (1997).
Andino et al. "AAV-mediated knockdown of phospholamban leads to improved contractility and calcium handling in cardiomyocytes" *The Journal of Gene Medicine* 10:132-142 (2008).
Bantel-Schaal et al. "Human Adeno-Associated Virus Type 5 Is Only Distantly Related to Other Known Primate Helper-Dependent Parvoviruses" *Journal of Virology* 73(2):939-947 (1999).
Brichard et al. "The Tyrosinase Gene Codes for an Antigen Recognized by Autologour Cytolytic T Lymphocytes on HLA-AZ Melanomas" *Journal of Experimental Medicine* 178:489-495 (1993).
Brown et al. "Erythrocyte P Antigen: Cellular Receptor for B19 Parvovirus" *Science* 262(5130):114-117 (1993).
Brown et al. "Chimeric Parvovirus B19 Capsids for the Presentation of Foreign Epitopes" *Virology* 198(2):477-488 (1994).
Chao et al. "Several Log Increase in Therapeutic Transgene Delivery by Distinct Adeno-Associated Viral Serotype Vectors" *Molecular Therapy* 2(6):619-623 (2000).
Chapman et al. "Structure, Sequence, and Function Correlations among Parvoviruses" *Virology* 194(2):491-508 (1993).
Chiorini et al. "Cloning of Adeno-Associated Virus Type 4 (AAV4) and Generation of Recombinant AAV4 Particles" *Journal of Virology* 71(9):6823-6833 (1997).
Chiorini et al. "Cloning and Characterization of Adeno-Associated Virus Type 5" *Journal of Virology* 73(2):1309-1319 (1999).
Chipman et al. "Cryo-electron microscopy studies of empty capsids of human parvovirus B19 complexed with its cellular receptor" *Proceedings of the National Academy of Sciences* 93:7502-7506 (1996).
Cleves, Ann E. "Protein transport: The nonclassical ins and outs" *Current Biology* 7:R318-R320 (1997).
Conway et al. "High-titer recombinant adeno-associated virus production utilizing a recombinant herpes simplex virus type 1 vector expressing AAV-2 Rep and Cap" *Gene Therapy* 6:986-993 (1999).
Devereux et al. "A comprehensive set of sequence analysis programs for the VAX" *Nucleic Acids Research* 12(1):387-395 (1984).
Fang et al. "Stable antibody expression at therapeutic levels using the 2A peptide" *Nature Biotechnology* 23:584-590 (2005).
Ferrari et al. "New developments in the generation of Ad-free high-titer rAAV gene therapy vectors" *Nature Medicine* 3(11):1295-1297 (1997).
Gao et al. "Novel adeno-associated viruses from rhesus monkeys as vectors for human gene therapy" *Proceedings of the National Academy of Sciences* 99(18):11854-11859 (2002).
Gao et al. "Clades of Adeno-Associated Viruses are Widely Disseminated in Human Tissues" *Journal of Virology* 78(12):6381-6388 (2004).
GenBank Accession No. AF028704 "Adeno-associated virus 6, complete genome" *NCBI* (2 pages) (Jan. 12, 1998).
GenBank Accession No. AF028705 "Adeno-associated virus 3B, complete genome" *NCBI* (2 pages) (Jan. 12, 1998).
GenBank Accession No. AF063497 "Adeno-associated virus 1, complete genome" *NCBI* (2 pages) (Apr. 27, 1999).
GenBank Accession No. AF288061 "Hamster parvovirus 5' terminal hairpin gene sequence" *NCBI* (1 page) (Apr. 13, 2001).
GenBank Accession No. AF513851 "Adeno-associated virus 7 nonstructural protein and capsid protein genes, complete cds." *NCBI* (3 pages) (Sep. 5, 2002).
GenBank Accession No. AF513852 "Adeno-associated virus 8 nonstructural protein and capsid protein genes, complete cds" *NCBI* (2 pages) (Sep. 5, 2002).
GenBank Accession No. AF043303 "Adeno-Associated virus 2, complete genome" *NCBI* (4 pages) (May 20, 2010).
GenBank Accession No. AH009962 "Hamster parvovirus" *NCBI* (1 page) (Aug. 25, 2016).
GenBank Accession No. AY028223 "B19 virus isolate patient_A. 1.1 genomic sequence" *NCBI* (1 page) (Apr. 16, 2001).
GenBank Accession No. AY028226 "B19 virus isolate patient_A. 2.1 genomic sequence" *NCBI* (1 page) (Apr. 16, 2001).
GenBank Accession No. AY530579 "Adeno-associated virus 9 isolate hu.14 capsid protein VP1 (cap) gene, complete cds" *NCBI* (2 pages) (Jun. 24, 2004).
GenBank Accession No. J00306 "Human somatostatin I gene and flanks" *NCBI* (2 pages) (Jan. 13, 1995).
GenBank Accession No. J01901 "Adeno-associated virus 2, complete genome" *NCBI* (3 pages) (Apr. 27, 1993).
GenBank Accession No. J02275 "Minute virus of mice, complete genome" *NCBI* (4 pages) (May 22, 1995).
GenBank Accession No. NC_001862 "Adeno-associated virus 6, complete genome" *NCBI* (3 pages) (Jan. 12, 2004).
GenBank Accession No. NC_001863 "Adeno-associated virus 3B, complete genome" *NCBI* (3 pages) (Jan. 12, 2014).
GenBank Accession No. NC_006152 "Adeno-associated virus 5, complete genome" *NCBI* (3 pages) (Dec. 8, 2008).
GenBank Accession No. NC_001540 "Bovine parvovirus, complete genome" *NCBI* (4 pages) (Nov. 30, 2009).
GenBank Accession No. NC_001358 "Parvovirus H1, complete genome" *NCBI* (3 pages) (Feb. 10, 2015).
GenBank Accession No. NC_001701 "Goose parvovirus, complete genome" *NCBI* (4 pages) (Jan. 28, 2010).
GenBank Accession No. NC_001829 "Adeno-associated virus—4, complete genome" *NCBI* (3 pages) (Jan. 28, 2010).
GenBank Accession No. NC_002077 "Adeno-associated virus—1, complete genome" *NCBI* (3 pages) (Mar. 11, 2010).
GenBank Accession No. NC_006261 "Adeno-associated virus—8, complete genome" *NCBI* (3 pages) (Mar. 11, 2010).
GenBank Accession No. NC_001729 "Adeno-associated virus—3, complete genome" *NCBI* (3 pages) (Jun. 28, 2010).
GenBank Accession No. NC_001401 "Adeno-associated virus—2, complete genome" *NCBI* (5 pages) (Dec. 2, 2014).
GenBank Accession No. NC_000883 "Human parvovirus B19, complete genome" *NCBI* (4 pages) (Feb. 10, 2015).
GenBank Accession No. NC_001510 "Minute virus of mice, complete genome" *NCBI* (5 pages) (Mar. 28, 2016).
GenBank Accession No. NP_044927 "capsid [Adeno-associated virus—4]" *NCBI* (2 pages) (Jan. 28, 2010).
GenBank Accession No. P01166 "Somatostatin precursor [Contains:Somatostatin-28; Somatostatin-14]" *NCBI* (2 pages) (Sep. 15, 2003).
GenBank Accession No. U89790 "Adeno-associated virus 4, complete genome" *NCBI* (2 pages) (Aug. 21, 1997).
GenBank Accession No. X01457 "Parvovirus h-1, complete genome" *NCBI* (3 pages) (Apr. 18, 2005).
Gorman et al. "Stable alteration of pre-mRNA splicing patterns by modified U7 small nuclear RNAs" *Proceedings of the National Academy of Sciences* 95:4929:4934 (1998).
Gregorevic et al. "Systemic Microdystrophin Gene Delivery Improves Skeletal Muscle Structure and Function in Old Dystrophic mdx Mice" *Molecular Therapy* 16(4):657-664 (2008).
Grifman et al. "Incorporation of Tumor-Targeting Peptides into Recombinant Adeno-Associated Virus Capsids" *Molecular Therapy* 3(6):964-975 (2001).
Hauck et al. "Characterization of Tissue Tropism Determinants of Adeno-Associated Virus Type 1" *Journal of Virology* 77(4):2768-2774 (2003).
Hoshijima et al. "Chronic suppression of heart-failure progression by a pseudophosphorylated mutant of phospholamban via in vivo cardiac rAAV gene delivery" *Nature Medicine* 8:864-871 (2002).
International Preliminary Report on Patentability corresponding to International Patent Application No. PCT/US2016/013460 (8 pages) (dated Jul. 18, 2017).
Karlin et al. "Applications and statistics for multiple high-scoring segments in molecular sequences" *Proceedings of National Academy of Sciences* 90:5873-5877 (1993).
Kawakami et al. "Identification of the Immunodominant Peptides of the MART-1 Human Melanoma Antigen Recognized by the Majority of HLA-A2-restricted Tumor Infiltrating Lymphocytes" *The Journal of Experimental Medicine* 180:347-352 (1994).

(56) References Cited

OTHER PUBLICATIONS

Kawakami et al. "Cloning of the gene coding for a shared human melanoma antigen recognized by autologous T cells infiltrating into tumor" *Proceedings of the National Academy of Sciences* 91:3515-3519 (1994).
Levine et al. "The Tumor Suppressor Genes" *Annual Review of Biochemistry* 62:623-651 (1993).
Li et al. "Construction of phospholamban antisense RNA recombinant adeno-associated virus vector and its effects in rat cardiomyocytes" *Acta Pharmalogica Sinica* 26(1)51-55 (2005).
Margolskee, R. F. "Epstein-Barr Virus Based Expression Vectors" *Current Topics in Microbiology and Immunology* 158:67-95 (1992) (Abstract only).
Miyamura et al. "Parvovirus particles at platforms for protein presentation" *Proceedings of National Academy of Sciences* 91:8507-8511 (1995).
Mori et al. "Two novel adeno-associated viruses from cynomolgus monkey:pseudotyping characterization of capsid protein" *Virology* 330:375-383 (2004).
Muramatsu et al. "Nucleotide Sequencing and Generation of an Infectious Clone of Adeno-Associated Virus 3" *Virology* 22(0367):208-217 (1996).
Muzyczka, N. "Use of Adeno-Associated Virus as a General Transduction Vector for Mammalian Cells" *Current Topics in Microbiology and Immunology* 158:97-129 (1992) (Abstract only).
Needleman et al. "A General Method Applicable to the Search for Similarities in the Amino Acid Sequence of Two Proteins" *Journal of Molecular Biology* 48(3):443-453 (1970).
Padron et al. "Structure of Adeno-Associated Virus Type 4" *Journal of Virology* 79(8):5047-5058 (2005).
Palombo et al. "Site-Specific Integration in Mammalian Cells Mediated by a New Hybrid Baculovirus-Adeno-Associated Virus Vector" *Journal of virology* 72(6):5025-5034 (1998).
Pearson et al. "Improved tools for biological sequence comparison" *Proceedings of National Academy Sciences* 85:2444-2448 (1988).
Puttaraju et al. "Spliceosome-mediated RNA trans-splicing as a tool for gene therapy" *Nature Biotechnology* 17:246-252 (1999).
Robbins et al. "Recognition of Tyrosinase by Tumor-infiltrating Lymphocytes from a Patient Responding to Immunotherapy" *Cancer Research* 54:3124-3126 (1994).
Rosenberg "The Immunotherapy of Solid Cancers Based on Cloning the Genes Encoding Tumor-Rejection Antigens" *Annual Review of Medicine* 47:481-491 (1996).
Rosenberg et al. "A New Era for Cancer Immunotherapy Based on the Genes that Encode Cancer Antigens" *Immunity* 10:281-287 (1999).
Shade et al. "Nucleotide Sequence and Genome Organization of Human Parvovirus B19 Isolated from the Serum of a Child during Aplastic Crisis" *Journal of Virology* 28(3):921-936 (1986).
Sharp et al. "RNA Interference" *Science* 287(5462):2431-2433 (2000).
Shi et al. "Insertional Mutagenesis at Positions 520 and 584 of Adeno-Associated Virus Type 2 (AAV2) Capsid Gene and Generation of AAV2 Vectors with Eliminated Heparin-Binding Ability and Introduced Novel Tropism" *Human Gene Therapy* 17:353-361 (2006).
Smith et al. "Comparison of Biosequences" *Advances in Applied Mathematics* 2:482-489 (1981).
Srivastava et al. "Nucleotide Sequence and Organization of the Adeno-Associated Virus 2 Genome" *Journal of Virology* 45(2):555-564 (1983).
Tinsley et al. "Amelioration of the dystrophic phenotype of mdx mice using a truncated utrophin transgene" *Nature* 384(6607):349-353 (1996).
Tsao et al. "The Three-Dimensional Structure of Canine Parvovirus and Its Functional Implications" *Science* 251(5000):1456-1464 (1991).
Urabe et al. "Insect Cells as a Factory to Produce Adeno-Associated Virus Type 2 Vectors" *Human Gene Therapy* 13:1935-1943 (2002).
Vincent et al. "Long-term correction of mouse dystrophic degeneration by adenovirus-mediated transfer of a minidystrophin gene" *Nature Genetics* 5:130-134 (1993).
Walters et al. "Structure of Adeno-Associated Virus Serotype 5" *Journal of Virology* 78(7):3361-3371 (2004).
Wang et al. "Adeno-associated virus vector carrying human minidystrophin genes effectively ameliorates muscular dystrophy in mdx mouse model" *Proceedings of the National Academy of Sciences* 97(25):13714-13719 (2000).
Wang et al. "Expanding the genetic code" *Annual Review of Biophysics and Biomolecular Structure* 35:225-249 (2006).
Xiao et al. "Gene Therapy Vectors Based on Adeno-Associated Virus Type 1" *Journal of Virology* 73(5):3994-4003 (1999).
Xie et al. "Canine Parvovirus Capsid Structure, Analyzed at 2.9 Å Resolution" *Journal of Molecular Biology* 264(3):497-420 (1996) (Abstract only).
Xie et al. "The atomic structure of adeno-associated virus (AAV-2), a vector for human gene therapy" *Proceeding of the National Academy of Sciences* 99(16):10405-10410 (2002).
Zhang et al. "Recombinant adenovirus expressing adeno-associated virus cap and rep proteins supports production of high-titer recombinant adeno-associated virus" *Gene Therapy* 8:704-712 (2001).
Zolotukhin et al. "Recombinant adeno-associated virus purification using novel methods improves infectious titer and yield" *Gene Therapy* 6:973-985 (1999).
International Search Report and the Written Opinion of the International Searching Authority corresponding to International Patent Application No. PCT/US2016/013460 (12 pages) (dated May 12, 2016).
Shen et al. "Multiple Roles for Sialylated Glycans in Determining the Cardiopulmonary Tropism of Adeno-Associated Virus 4" *Journal of Virology* 87(24):13206-13213 (2013).
Examination Report corresponding to European Patent Application No. 16737901.5 (4 pages) (dated Sep. 23, 2019).

* cited by examiner

FIG. 4

US 10,907,176 B2

METHODS AND COMPOSITIONS FOR TARGETED GENE TRANSFER

STATEMENT OF PRIORITY

This application is a 35 U.S.C. § 371 national phase application of International Application Serial No. PCT/US2016/013460, filed Jan. 14, 2016, which claims the benefit, under 35 U.S.C. § 119(e), of U.S. Provisional Application Ser. No. 62/103,462, filed Jan. 14, 2015, the entire contents of each of which are incorporated by reference herein.

STATEMENT OF GOVERNMENT SUPPORT

This invention was made with government support under Grant No. R01-HL089221 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-731_updated_ST25.txt, 242,058 bytes in size, generated on Jul. 15, 2020 and filed via EFS-Web, is provided in lieu of a paper copy. This Sequence Listing is incorporated by reference into the specification for its disclosures.

FIELD OF THE INVENTION

The present invention relates to modified capsid proteins from adeno-associated virus (AAV) and virus capsids and virus vectors comprising the same. In particular, the invention relates to modified AAV capsid proteins and capsids comprising the same that can be incorporated into virus vectors to confer a desirable transduction profile with respect to a target tissue(s) of interest.

BACKGROUND OF THE INVENTION

New adeno-associated virus (AAV) strains isolated from animal tissues and adenoviral stocks have expanded the panel of AAV vectors available for therapeutic gene transfer applications. Comprehensive efforts to map tissue tropisms of these AAV isolates in animal models are currently underway. The ability to direct homing of AAV vectors to selective organs is useful for gene therapy and other therapeutic applications.

The present inventor addresses a need in the art for nucleic acid delivery vectors with desirable targeting features.

SUMMARY OF THE INVENTION

In one aspect, the present invention provides an adeno-associated virus (AAV) serotype 4 (AAV4) capsid protein, wherein the AAV4 capsid protein comprises a modification at amino acid residues K492, K503 and N585 and further comprises a modification at one or more of amino acid residues M523, G580, G581, Q583, S586, N587, L588, T590, D592, R593, L594, T595 and/or A596 in any combination, wherein the numbering of the residues is based on the amino acid sequence of SEQ ID NO:1.

In a further aspect, the present invention provides an adeno-associated virus (AAV) serotype 4 (AAV4) capsid protein, wherein the AAV4 capsid protein comprises a modification at amino acid residues K493, K504 and N586 and further comprises a modification at one or more of amino acid residues M524, G581, G582, Q584, S587, N588, L589, T591, D593, R594, L595, T596 and/or A597 in any combination, wherein the numbering of the residues is based on the amino acid sequence of SEQ ID NO:2. The AAV4 capsid protein of claim 1, comprising a K492E substitution, a K503E substitution and/or a N585S substitution, in any combination.

Further provided herein is an AAV capsid comprising the AAV4 capsid protein of this invention. Additionally provided is a virus vector comprising: (a) the AAV capsid of this invention; and (b) a nucleic acid comprising at least one terminal repeat sequence, wherein the nucleic acid is encapsidated by the AAV capsid. Also provided herein is a composition comprising the virus vector of this invention in a pharmaceutically acceptable carrier.

A further aspect of this invention is a method of introducing a nucleic acid molecule into a cell, comprising contacting the cell with the virus vector of this invention and/or the composition of this invention.

In an additional aspect, the present invention provides a method of delivering a nucleic acid molecule to a subject, comprising administering to the subject the virus vector of this invention and/or the composition of this invention.

Also provided herein is a method of selectively transducing a cell having polysialic acid on the surface, comprising contacting the cell with the virus vector of this invention or the composition of this invention.

An additional aspect of this invention is a method of selectively delivering a nucleic acid molecule of interest to a central nervous system progenitor cell and/or neuroblast, comprising contacting the progenitor cell and/or neuroblast with the virus vector of this invention, wherein the virus vector comprises the nucleic acid molecule of interest.

Furthermore, the present invention provides a method of treating a neurological disorder or defect in a subject, comprising administering to the subject the virus vector of this invention, wherein the virus vector comprises a nucleic acid molecule that encodes a therapeutic protein or therapeutic RNA effective in treating the neurological disorder or defect.

An additional aspect of this invention includes a method of selectively transducing a cell having polysialic acid on the surface, comprising contacting the cell with a virus vector of this invention.

Also provided herein is a method of selectively delivering a nucleic acid molecule of interest to a central nervous system progenitor cell and/or neuroblast, comprising contacting the progenitor cell and/or neuroblast with a virus vector of this invention, wherein the virus vector comprises the nucleic acid molecule of interest.

Another aspect of this invention is a method of treating a neurological disorder or defect in a subject, comprising administering to the subject a virus vector of this invention, wherein the virus vector comprises a nucleic acid molecule that encodes a therapeutic protein or therapeutic RNA effective in treating the neurological disorder or defect.

These and other aspects of the invention are addressed in more detail in the description of the invention set forth below.

DETAILED DESCRIPTION OF THE INVENTION

Figure 1:
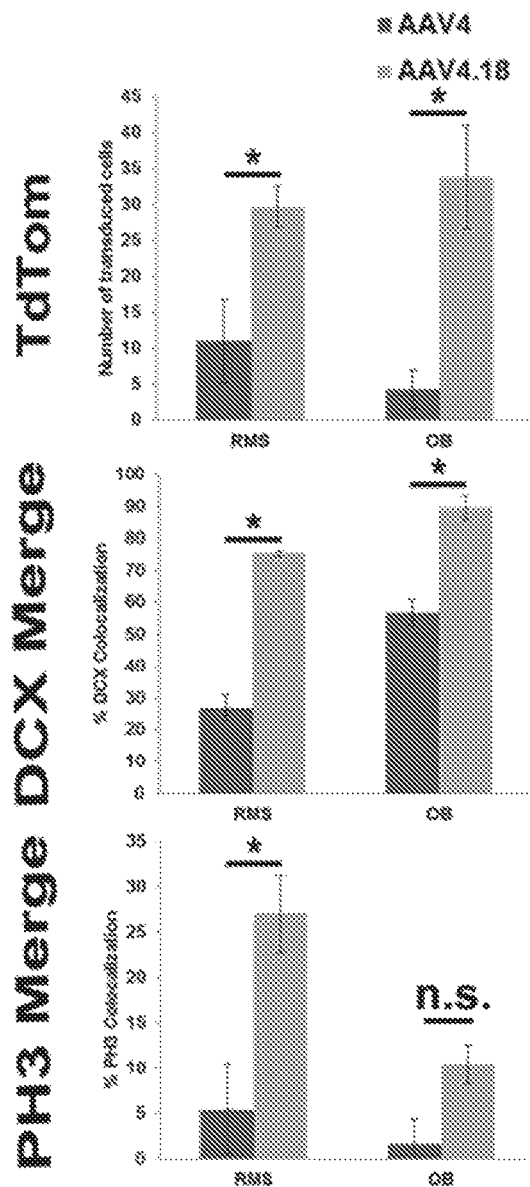
FIG. 1. Quantitative analysis of the number of tdTom+ cells and percentage colocalization with Dcx+ processes and PH3+ cells in the RMS and OB regions of AAV4 (dark grey bars) or 4.18 (light grey bars) treated mice are shown. Error bars indicate standard deviation and statistical significance indicated by n.s., not significant or *p<0.05 as determined by student t-test. All experiments were carried out in quadruplicate.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference herein in their entirety.

Definitions

The following terms are used in the description herein and the appended claims:

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 25%, 35%, 50%, 75%, 80%, 85%, 90%, 95%, 97% or more.

As used herein, the terms "enhance," "enhances," "enhancement" and similar terms indicate an increase of at least about 5%, 10%, 20%, 25%, 50%, 75%, 100%, 150%, 200%, 300%, 400%, 500% or more.

The term "parvovirus" as used herein encompasses the family Parvoviridae, including autonomously replicating parvoviruses and dependoviruses. The autonomous parvoviruses include members of the genera *Parvovirus, Erythrovirus, Densovirus, Iteravirus,* and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, avian AAV, bovine AAV, canine AAV, equine AAV, ovine AAV, and any other AAV now known or later discovered. See, e.g., BERNARD N. FIELDS et al., VIROLOGY, volume 2, chapter 69 (4th ed., Lippincott-Raven Publishers). A number of relatively new AAV serotypes and clades have been identified (see, e.g., Gao et al. (2004) *J. Virology* 78:6381-6388; Moris et al. (2004) *Virology* 33-:375-383; and Table 1).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as the GenBank® Database. See, e.g., GenBank Accession Numbers NC_044927, NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al. (1983) *J. Virology* 45:555; Chiorini et al. (1998) *J. Virology* 71:6823; Chiorini et al. (1999) *J. Virology* 73:1309; Bantel-Schaal et al. (1999) *Virology* 73:939; Xiao et al. (1999) *J. Virology* 73:3994; Muramatsu et al. (1996) *Virology* 221:208; Shade et al. (1986) *J. Virol.* 58:921; Gao et al. (2002) *Proc. Nat. Acad. Sci. USA* 99:11854; Moris et al. (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1.

TABLE 1

|  | GenBank Accession Number |
|---|---|
| Complete Genomes |  |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617, AAR26465 |
| AAV11 | AAT46339, AY631966 |
| AAV12 | ABI16639, DQ813647 |
| Clade A |  |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B |  |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C |  |
| Hu9 | AY530629 |
| Hu10 | AY530576 |
| Hu11 | AY530577 |
| Hu53 | AY530615 |
| Hu55 | AY530617 |
| Hu54 | AY530616 |

TABLE 1-continued

|  | GenBank Accession Number |
|---|---|
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D |  |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E |  |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F |  |
| Hu14 (AAV9) | AY530579 |
| Hu31 | AY530596 |
| Hu32 | AY530597 |
| Clonal Isolate |  |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al. (2002) *Proc. Nat. Acad. Sci.* 99:10405-10), AAV4 (Padron et al. (2005) *J. Virol.* 79: 5047-58), AAV5 (Walters et al. (2004) *J. Virol.* 78: 3361-71) and CPV (Xie et al. (1996) *J. Mol. Biol.* 6:497-520 and Tsao et al. (1991) *Science* 251: 1456-64).

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest. Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form the virus may take within the cell.

As used here, "systemic tropism" and "systemic transduction" (and equivalent terms) indicate that the virus capsid or virus vector of the invention exhibits tropism for or transduces, respectively, tissues throughout the body (e.g., brain, lung, skeletal muscle, heart, liver, kidney and/or pancreas). In embodiments of the invention, systemic transduction of muscle tissues (e.g., skeletal muscle, diaphragm and cardiac muscle) is observed. In other embodiments, systemic transduction of skeletal muscle tissues is achieved. For example, in particular embodiments, essentially all skeletal muscles throughout the body are transduced (although the efficiency of transduction may vary by muscle type). In particular embodiments, systemic transduction of limb muscles, cardiac muscle and diaphragm muscle is achieved. Optionally, the virus capsid or virus vector is administered via a systemic route (e.g., systemic route such as intravenously, intra-articularly or intra-lymphatically). Alternatively, in other embodiments, the capsid or virus vector is delivered locally (e.g., to the footpad, intramuscularly, intradermally, subcutaneously, topically). Examples of modified virus vectors according to the present invention are provided in Table 5.

Unless indicated otherwise, "efficient transduction" or "efficient tropism," or similar terms, can be determined by reference to a suitable control (e.g., at least about 50%, 60%, 70%, 80%, 85%, 90%, 95% or more of the transduction or tropism, respectively, of the control). In particular embodiments, the virus vector efficiently transduces or has efficient tropism for skeletal muscle, cardiac muscle, diaphragm muscle, pancreas (including β-islet cells), spleen, the gastrointestinal tract (e.g., epithelium and/or smooth muscle), cells of the central nervous system, lung, joint cells, and/or kidney. Suitable controls will depend on a variety of factors including the desired tropism profile.

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism) for liver, kidney, gonads and/or germ cells. In particular embodiments, undesirable transduction of tissue(s) (e.g., liver) is 20% or less, 10% or less, 5% or less, 1% or less, 0.1% or less as compared with the level of transduction of the desired target tissue(s) (e.g., skeletal muscle, diaphragm muscle, cardiac muscle and/or cells of the central nervous system).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

As used herein, by "isolate" or "purify" (or grammatical equivalents) a virus vector, it is meant that the virus vector is at least partially separated from at least some of the other components in the starting material. In representative embodiments an "isolated" or "purified" virus vector is enriched by at least about 10-fold, 100-fold, 1000-fold, 10,000-fold or more as compared with the starting material.

A "therapeutic protein" is a protein that can alleviate, reduce, prevent, delay and/or stabilize symptoms that result from an absence or defect in a protein in a cell or subject and/or is a protein that otherwise confers a benefit to a subject.

A "therapeutic RNA molecule" or "functional RNA molecule" as used herein can be an antisense nucleic acid, a ribozyme (e.g., as described in U.S. Pat. No. 5,877,022), an RNA that effects spliceosome-mediated trans-splicing (see, Puttaraju et al. (1999) *Nature Biotech.* 17:246; U.S. Pat. Nos. 6,013,487; 6,083,702), an interfering RNA (RNAi) including siRNA, shRNA or miRNA, which mediate gene silencing (see, Sharp et al., (2000) *Science* 287:2431), and any other non-translated RNA, such as a "guide" RNA (Gorman et al. (1998) *Proc. Nat. Acad. Sci. USA* 95:4929; U.S. Pat. No. 5,869,248 to Yuan et al.) and the like as are known in the art.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid molecule" are used interchangeably herein and refer to a nucleic acid sequence that is not naturally occurring in the virus. Generally, the heterologous nucleic acid comprises an open reading frame that encodes a protein or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka (1992) Curr. Topics Microbiol. Immunol. 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention, the rAAV vector genome comprises at least one terminal repeat (TR) sequence (e.g., AAV TR sequence), optionally two TRs (e.g., two AAV TRs), which typically will be at the 5' and 3' ends of the vector genome and flank the heterologous nucleic acid sequence, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al. (2000) Molecular Therapy 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 2.

Alternatively, the amino acid can be a modified amino acid residue (nonlimiting examples are shown in Table 3) and/or can be an amino acid that is modified by post-translation modification (e.g., acetylation, amidation, formylation, hydroxylation, methylation, phosphorylation or sulfatation).

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 3

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al. *Annu Rev Biophys Biomol Struct.* 35:225-49 (2006)). These unnatural amino acids can advantageously be used to chemically link molecules of interest to the AAV capsid protein.

Modified AAV Capsid Proteins and Virus Capsids and Virus Vectors Comprising the Same.

The present invention provides AAV capsid proteins comprising a mutation (i.e., a modification) in the amino acid sequence and virus capsids and virus vectors comprising the modified AAV capsid protein. The inventors have discovered that modifications at the amino acid positions described herein can confer one or more desirable properties to virus vectors comprising the modified AAV capsid protein including without limitation: (i) selective transduction of cells having polysialic acid on the surface; (ii) a switch in receptor specificity from sialic acid (SA) to polysialic acid (PSA); (iii) enhanced transduction of cells across the brain; and (iii) redirection of AAV vectors to migrating progenitor cells.

In particular embodiments, the modified AAV capsid protein of the invention comprises one or more mutations (i.e., modifications) in the amino acid sequence of the native AAV4 capsid protein or the corresponding region of a capsid protein from another AAV, including but not limited to AAV11, AAV12, bovine AAV, Rh32, Rh33 and Rh34.

As used herein, a "mutation" or "modification" in an amino acid sequence includes substitutions, insertions and/or deletions, each of which can involve one, two, three, four, five, six, seven, eight, nine, ten or more amino acids. In particular embodiments, the modification is a substitution. For example, in particular embodiments, the AAV4 capsid protein sequence is modified at amino acid positions 492, 503, 585, 523, 590, 581, 583, 594 and/or 596, in any combination. Amino acid numbering is based on the amino acid sequence of an AAV4 capsid protein having GenBank Accession No. NP_044927 (SEQ ID NO:1):

```
MTDGYLPDWLEDNLSEGVREWWALQPGAPKPKANQQHQDNARGLVLPGYK

YLGPGNGLDKGEPVNAADAAALEHDKAYDQQLKAGDNPYLKYNHADAEFQ

QRLQGDTSFGGNLGRAVFQAKKRVLEPLGLVEQAGETAPGKKRPLIESPQ

QPDSSTGIGKKGKQPAKKKLVFEDETGAGDGPPEGSTSGAMSDDSEMRAA

AGGAAVEGGQGADGVGNASGDWHCDSTWSEGHVTTTSTRTWVLPTYNNHL

YKRLGESLQSNTYNGFSTPWGYFDFNRFHCHFSPRDWQRLINNNWGMRPK

AMRVKIFNIQVKEVTTSNGETTVANNLTSTVQIFADSSYELPYVMDAGQE

GSLPPFPNDVFMVPQYGYCGLVTGNTSQQQTDRNAFYCLEYFPSQMLRTG

NNFEITYSFEKVPFHSMYAHSQSLDRLMNPLIDQYLWGLQSTTTGTTLNA

GTATTNFTKLRPTNFSNFKKNWLPGPSIKQQGFSKTANQNYKIPATGSDS

LIKYETHSTLDGRWSALTPGPPMATAGPADSKFSNSQLIFAGPKQNGNTA

TVPGTLIFTSEEELAATNATDTDMWGNLPGGDQSNSNLPTVDRLTALGAV

PGMVWQNRDIYYQGPIWAKIPHTDGHFHPSPLIGGFGLKHPPPQIFIKNT

PVPANPATTFSSTPVNSFITQYSTGQVSVQIDWEIQKERSKRWNPEVQFT

SNYGQQNSLLWAPDAAGKYTEPRAIGTRYLTHHL
or
an AAV4 capsid protein having the following amino
acid sequence (SEQ ID NO: 2):
MAADGYLPDWLEDNLSEGVREWWALQPGAPKPKANQQHQDNARGLVLPGY

KYLGPGNGLDKGEPVNAADAAALEHDKAYDQQLKAGDNPYLKYNHADAEF

QQRLQGDTSFGGNLGRAVFQAKKRVLEPLGLVEQAGETAPGKKRPLIESP

QQPDSSTGIGKKGKQPAKKKLVFEDETGAGDGPPEGSTSGAMSDDSEMRA

AAGGAAVEGGQGADGVGNASGDWHCDSTWSEGHVTTTSTRTWVLPTYNNH

LYKRLGESLQSNTYNGFSTPWGYFDFNRFHCHFSPRDWQRLINNNWGMRP

KAMRVKIFNIQVKEVTTSNGETTVANNLTSTVQIFADSSYELPYVMDAGQ

EGSLPPFPNDVFMVPQYGYCGLVTGNTSQQQTDRNAFYCLEYFPSQMLRT

GNNFEITYSFEKVPFHSMYAHSQSLDRLMNPLIDQYLWGLQSTTTGTTLN

AGTATTNFTKLRPTNFSNFKKNWLPGPSIKQQGFSKTANQNYKIPATGSD

SLIKYETHSTLDGRWSALTPGPPMATAGPADSKFSNSQLIFAGPKQNGNT

ATVPGTLIFTSEEELAATNATDTDMWGNLPGGDQSNSNLPTVDRLTALGA

VPGMVWQNRDIYYQGPIWAKIPHTDGHFHPSPLIGGFGLKHPPPQIFIKN

TPVPANPATTFSSTPVNSFITQYSTGQVSVQIDWEIQKERSKRWNPEVQF

TSNYGQQNSLLWAPDAAGKYTEPRAIGTRYLTHHL
```

The modified virus capsid proteins of the invention can be but are not limited to AAV capsid proteins in which amino acids from one AAV capsid protein are substituted into another AAV capsid protein, and the substituted and/or inserted amino acids can be from any source, and can further be naturally occurring or partially or completely synthetic. Furthermore, the AAV capsid proteins of this invention can have a native amino acid sequence or a synthetic amino acid sequence.

Thus, in one embodiment, the present invention provides an adeno-associated virus (AAV) serotype 4 (AAV4) capsid protein, wherein the capsid protein comprises a mutation at K492, K503 and N585 and further comprises a mutation at one or more of the following amino acid residue sites: M523, G580, G581, Q583, S586, N587, L588, T590, D592, R593, L594, T595 and/or A596, in any combination. In some embodiments, the AAV4 capsid protein can comprise a K492E mutation, a K503E mutation and/or a N585S mutation, in any combination. In further embodiments, the AAV capsid protein can comprise a mutation at one or more of the amino acid residue sites: K492, K503, M523, G580, G581, Q583, N585, S586, N587, L588, T590, D592, R593, L594, T595 and/or A596, singly or in any combination, wherein the mutation is a substitution of the native amino acid with any other amino acid that is not the native amino acid at that position. Examples of amino acid residues that can be substituted for the native amino acid at these respective positions are set forth in Tables 2 and 3.

In a further embodiment, the present invention provides an adeno-associated virus (AAV) serotype 4 (AAV4) capsid protein, wherein the AAV4 capsid protein comprises a modification at amino acid residues K492, K503 and N585 and further comprises a modification at one or more of amino acid residues M523, G580, G581, Q583, S586, N587, L588, T590, D592, R593, L594, T595 and/or A596 in any combination, wherein the numbering of the residues is based on the amino acid sequence of SEQ ID NO:1.

In some embodiments, the AAV4 capsid protein referenced above can comprise a K492E substitution, a K503E substitution and/or a N585S substitution, in any combination. In some embodiments, the AAV4 capsid protein referenced above can comprise a N585R substitution.

The present invention further provides an adeno-associated virus (AAV) serotype 4 (AAV4) capsid protein, wherein the AAV4 capsid protein comprises a modification at amino acid residues K493, K504 and N586 and further comprises a modification at one or more of amino acid residues M524, G581, G582, Q584, S587, N588, L589, T591, D593, R594, L595, T596 and/or A597 in any combination, wherein the numbering of the residues is based on the amino acid sequence of SEQ ID NO:2.

In some embodiments, the AAV4 capsid protein referenced above can comprise a K493E substitution, a K504E substitution and/or a N586S substitution, in any combination. In some embodiments, the AAV4 capsid protein referenced above can comprise a N586R substitution In one embodiment, the AAV4 capsid protein of this invention can comprise the amino acid sequence of AAV4.18-6a (SEQ ID NO:29).

In one embodiment, the AAV4 capsid protein of this invention can comprise the amino acid sequence of AAV4.18-6b (SEQ ID NO:30).

In one embodiment, the AAV4 capsid protein of this invention can comprise the amino acid sequence of AAV4.18-6c (SEQ ID NO:31).

In one embodiment, the AAV4 capsid protein of this invention can comprise the amino acid sequence of AAV4.18-5a (SEQ ID NO:32).

In one embodiment, the AAV4 capsid protein of this invention can comprise the amino acid sequence of AAV4.18-5b (SEQ ID NO:33).

In further embodiments, the AAV4 capsid protein of this invention can comprise any of the amino acid sequences set forth herein in the specification and Sequence Listing.

Figure 3:
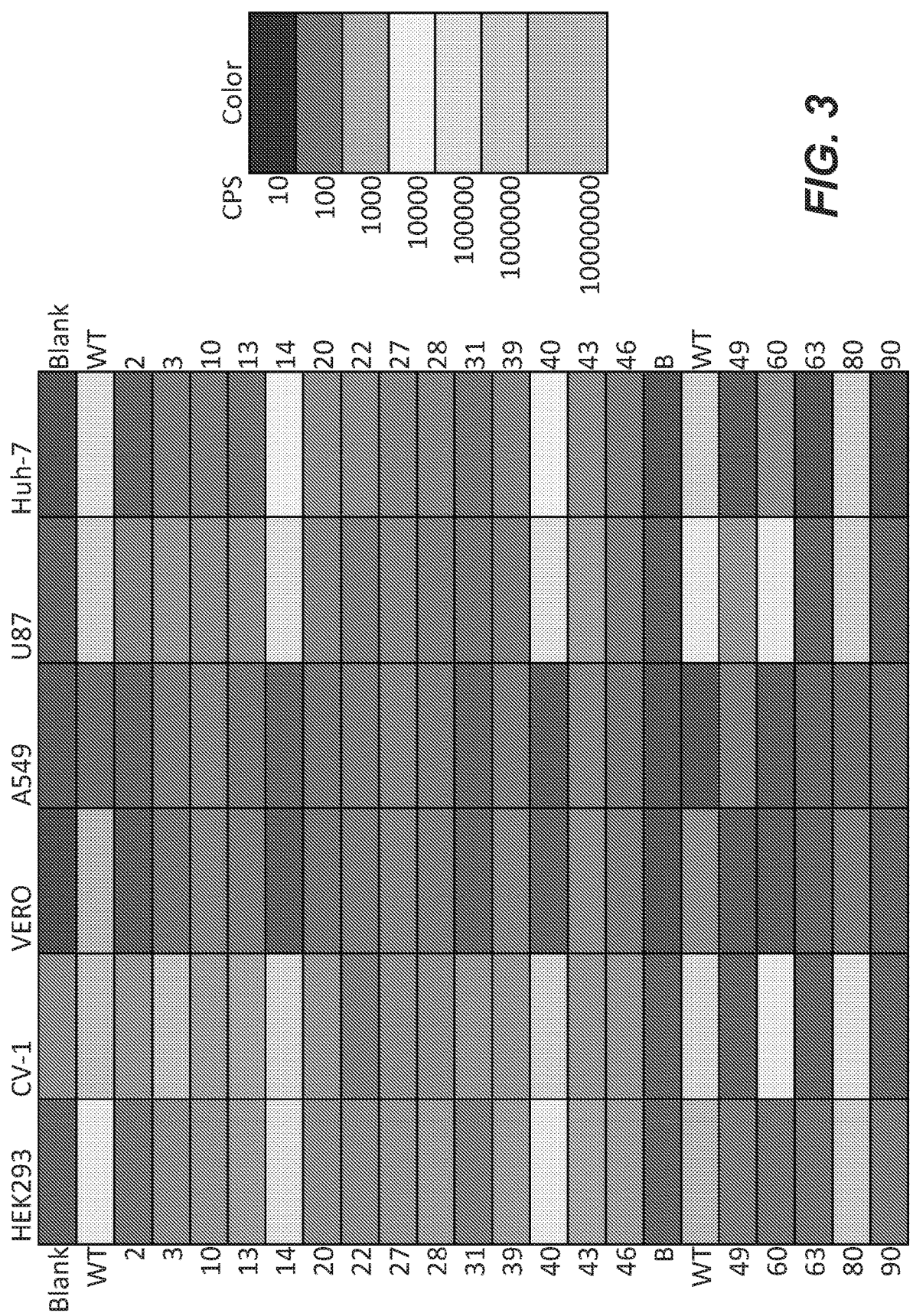
FIG. 3. Graph plot showing relative gene expression efficiency of several AAV4 mutants as described herein.
Figure 4:
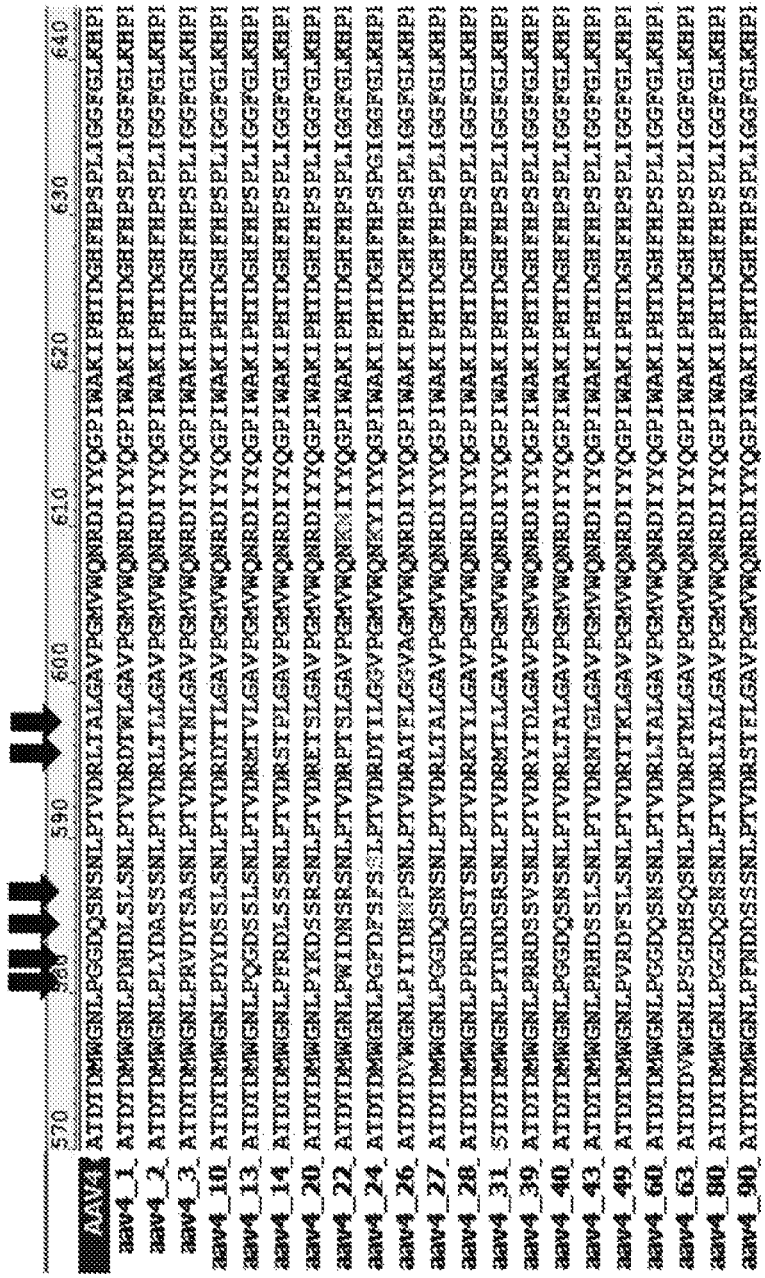
FIG. 4. Alignment of different AAV4 clones showing substitutions. AAV4: SEQ ID NO:36; AAV4_1: SEQ ID NO:37; AAV4_2: SEQ ID NO:38; AAV4_3: SEQ ID NO:39; AAV4_10: SEQ ID NO:40; AAV4_13: SEQ ID NO:41; AAV4_14: SEQ ID NO:42; AAV4_20: SEQ ID NO:43; AAV4_22: SEQ ID NO:44; AAV4_24: SEQ ID NO:45; AAV4_26: SEQ ID NO:46; AAV4_27: SEQ ID NO:47; AAV4_28: SEQ ID NO:48; AAV4_31: SEQ ID NO:49; AAV4_39: SEQ ID NO:50; AAV4_40: SEQ ID NO:51; AAV4_43: SEQ ID NO:52; AAV4_49: SEQ ID NO:53; AAV4_60: SEQ ID NO:54; AAV4_63: SEQ ID NO:55; AAV4_63: SEQ ID NO:55; AAV4_80: SEQ ID NO:56; AAV4_90: SEQ ID NO:57.

Additional nonlimiting examples of AAV4 capsid proteins with substitutions as described herein are provided in FIG. 4 (aav4_1, aav4_2, aav4_3, aav4_10, aav4_13, aav4_14, aav4_20, aav4_22, aav4_24, aav4_26, aav4_27, aav4_28, aav4_31, aav4_39, aav440, aav4_43, aav4_49, aav4_60, aav4_63, aav4_80, and aav4_90), and the relative gene expression efficiency of these clones (X axis) on different transformed cell types (Y axis) is provided in FIG. 3.

Further provided herein is an AAV capsid comprising the AAV4 capsid protein described herein as well as a virus vector comprising the AAV capsid. Also provided herein is a composition comprising the virus vector of this invention in a pharmaceutically acceptable carrier.

As described herein, the nucleic acid and amino acid sequences of the capsid proteins from a number of AAVs are known in the art. Thus, the amino acid(s) "corresponding" to amino acid positions 492, 503, 585, 523, 580, 582, 583, 594 and 596 of the reference AAV4 capsid protein can be readily determined for any other AAV capsid protein, including, for example, AAV11, AAV12, bovine AAV, clonal isolate Rh32, clonal isolate Rh33 or clonal isolate Rh34 (e.g., by using sequence alignments as are well known in the art).

The invention contemplates that the modified capsid proteins of the invention can be produced by modifying the capsid protein of any AAV now known or later discovered. Further, the AAV capsid protein that is to be modified can be a naturally occurring AAV capsid protein (e.g., an AAV2, AAV3a or 3b, AAV4, AAV5, AAV8, AAV9, AAV10 or AAV11 capsid protein or any of the AAV shown in Table 1) but is not so limited. Those skilled in the art will understand that a variety of manipulations to the AAV capsid proteins are known in the art and the invention is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11 and/or AAV12 or any other AAV now known or later discovered). Such AAV capsid proteins are also within the scope of the present invention.

Thus, in particular embodiments, the AAV capsid protein to be modified can be derived from a naturally occurring AAV but further comprise one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10, AAV11 or AAV12 capsid protein or a capsid protein from any of the AAV shown in Table 1, etc.), it is intended to encompass the native capsid protein as well as capsid proteins that have alterations other than the modifications of the invention. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids inserted therein (other than the insertions of the present invention) as compared with the native AAV capsid protein sequence. In embodiments of the invention, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acid substitutions (other than the amino acid substitutions according to the present invention) as compared with the native AAV capsid protein sequence. In embodiments of the invention, the capsid protein comprises a deletion of 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids (other than the amino acid deletions of the invention) as compared with the native AAV capsid protein sequence.

Thus, for example, the term "AAV4 capsid protein" includes AAV capsid proteins having the native AAV4 capsid protein sequence (see GenBank Accession No. NC_044927) as well as those comprising substitutions, insertions and/or deletions (as described herein) in the native AAV4 capsid protein sequence.

In particular embodiments, the AAV capsid protein has the native AAV capsid protein sequence or has an amino acid sequence that is at least about 90%, 95%, 97%, 98% or 99% similar or identical to a native AAV capsid protein sequence. For example, in particular embodiments, an "AAV4" capsid protein encompasses the native AAV4 capsid protein sequence as well as sequences that are at least about 90%, 95%, 97%, 98% or 99% similar or identical to the native AAV4 capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch *J. Mol. Biol.* 48,443 (1970), by the search for similarity method of Pearson & Lipman, *Proc. Natl. Acad. Sci. USA* 85,2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. *Nucl. Acid Res.* 12, 387-395 (1984), or by inspection.

Another suitable algorithm is the BLAST algorithm, described in Altschul et al. *J. Mol. Biol.* 215, 403-410, (1990) and Karlin et al. *Proc. Natl. Acad. Sci. USA* 90, 5873-5787 (1993). A particularly useful BLAST program is the WU-BLAST-2 program which was obtained from Altschul et al. *Methods in Enzymology,* 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

In representative embodiments of the invention, a substitution is made at K492, K503 and N585 of the native AAV4 capsid protein (using VP1 numbering) or the corresponding positions of other AAVs, i.e., at the amino acids corresponding to amino acid positions 492, 503 and 585 of the native AAV4 capsid protein and at least one substitution is made at M523, G580, G581, Q583, L594 and/or A596, singly or in any combination or the corresponding positions of other AAVs, i.e., at the amino acids corresponding to amino acid positions 523, 580, 581, 583, 594 and/or 596 of the native AAV4 capsid protein. The amino acid positions in other AAV serotypes or modified AAV capsids that "correspond to" these positions in the native AAV4 capsid protein will be apparent to those skilled in the art and can be readily determined using sequence alignment techniques (see, e.g., FIG. 7 of WO 2006/066066) and/or crystal structure analysis (Padron et al. (2005) *J. Virol.* 79:5047-58).

The invention also provides a virus capsid comprising, consisting essentially of, or consisting of the modified AAV capsid protein of the invention. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11 or any other AAV shown in Table 1 or is derived from any of the foregoing by one or more insertions, substitutions and/or deletions.

The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In one embodiment of the invention the therapeutically useful molecule is covalently linked (i.e., conjugated or chemically coupled) to the capsid proteins. Methods of covalently linking molecules are known by those skilled in the art.

The modified virus capsids of the invention also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on particular cells and a delivery vector can be administered subsequently or concurrently, which may reduce transduction of the blocked cells, and enhance transduction of other targets (e.g., CNS progenitor cells and/or neuroblasts).

According to representative embodiments, modified virus capsids can be administered to a subject prior to and/or concurrently with a modified virus vector according to the present invention. Further, the invention provides compositions and pharmaceutical formulations comprising the inventive modified virus capsids; optionally, the composition also comprises a modified virus vector of the invention.

The invention also provides nucleic acid molecules (optionally, isolated nucleic acid molecules) encoding the modified virus capsids and capsid proteins of the invention. Further provided are vectors comprising the nucleic acid molecules and cells (in vivo or in culture) comprising the nucleic acid molecules and/or vectors of the invention.

Suitable vectors include without limitation viral vectors (e.g., adenovirus, AAV, herpesvirus, vaccinia, poxviruses, baculoviruses, and the like), plasmids, phage, YACs, BACs, and the like. Such nucleic acid molecules, vectors and cells can be used, for example, as reagents (e.g., helper packaging constructs or packaging cells) for the production of modified virus capsids or virus vectors as described herein.

Virus capsids according to the invention can be produced using any method known in the art, e.g., by expression from a baculovirus (Brown et al. (1994) *Virology* 198:477-488).

The modifications to the AAV capsid protein according to the present invention are "selective" modifications. This approach is in contrast to previous work with whole subunit or large domain swaps between AAV serotypes (see, e.g., international patent publication WO 00/28004 and Hauck et al. (2003) *J. Virology* 77:2768-2774). In particular embodiments, a "selective" modification results in the insertion and/or substitution and/or deletion of less than about 20, 18, 15, 12, 10, 9, 8, 7, 6, 5, 4 or 3 contiguous amino acids.

The modified capsid proteins and capsids of the invention can further comprise any other modification, now known or later identified.

For example, the AAV capsid proteins and virus capsids of the invention can be chimeric in that they can comprise all or a portion of a capsid subunit from another virus, optionally another parvovirus or AAV, e.g., as described in international patent publication WO 00/28004.

The virus capsid can be a targeted virus capsid comprising a targeting sequence (e.g., substituted or inserted in the viral capsid) that directs the virus capsid to interact with cell-surface molecules present on a desired target tissue(s) (see, e.g., international patent publication WO 00/28004 and Hauck et al. (2003) *J. Virology* 77:2768-2774); Shi et al. *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al. *Molecular Therapy* 3:964-975 (2001)).

For example, some of the virus capsids of the invention have relatively inefficient tropism toward most target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another possibility one or more non-naturally occurring amino acids as described by Wang et al. (*Annu Rev Biophys Biomol Struct.* 35:225-49 (2006)) can be incorporated into the AAV capsid subunit at an orthogonal site as a means of redirecting a low-transduction vector to a desired target tissue(s). These unnatural amino acids can advantageously be used to chemically link molecules of interest to the AAV capsid protein including without limitation: glycans (mannose—dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques,* 1st edition, Academic Press, 1996).

In representative embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV 4, AAV5) to confer heparin binding to the resulting mutant.

B19 infects primary erythroid progenitor cells using globoside as its receptor (Brown et al. (1993) *Science* 262:114). The structure of B19 has been determined to 8 Å resolution (Agbandje-McKenna et al. (1994) *Virology* 203:106). The region of the B19 capsid that binds to globoside has been mapped between amino acids 399-406 (Chapman et al. (1993) *Virology* 194:419), a looped out region between β-barrel structures E and F (Chipman et al. (1996) *Proc. Nat. Acad. Sci. USA* 93:7502). Accordingly, the globoside receptor binding domain of the B19 capsid may be substituted into the AAV capsid protein to target a virus capsid or virus vector comprising the same to erythroid cells.

In representative embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein. Also encompassed are peptide motifs that direct uptake by specific cells, e.g., a FVFLP peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties, polysialic acid moieties, glycoproteins, and gangliosides, MHC I glycoproteins, carbohydrate components found on membrane glycoproteins, including, mannose, N-acetyl-galactosamine, N-acetyl-glucosamine, fucose, galactose, and the like.

As yet a further alternative, the targeting sequence may be a peptide that can be used for chemical coupling (e.g., can comprise arginine and/or lysine residues that can be chemically coupled through their R groups) to another molecule that targets entry into a cell.

The foregoing embodiments of the invention can be used to deliver a heterologous nucleic acid to a cell or subject as described herein. Thus, in one embodiment, the present invention provides a method of introducing a nucleic acid molecule into a cell, comprising contacting the cell with the virus vector and/or composition of this invention.

Further provided herein is a method of delivering a nucleic acid molecule to a subject, comprising administering to the subject the virus vector of this invention and/or the composition of this invention. In some embodiments, the virus vector or composition is administered to the central nervous system of the subject.

Additionally provided herein is a method of selectively transducing a cell having polysialic acid on the surface, comprising contacting the cell with the virus vector of this invention and/or the composition of this invention.

The present invention further provides a method of delivering a nucleic acid molecule of interest to a central nervous system progenitor cell and/or neuroblast, comprising contacting the progenitor cell and/or neuroblast with the virus vector of this invention, wherein the virus vector comprises the nucleic acid molecule of interest. In some embodiments of this method, the nucleic acid molecule of interest encodes a therapeutic protein or therapeutic RNA.

In some embodiments of the methods described above, the cell having polysialic acid on the surface, the central nervous system progenitor cell and/or the neuroblast can be in a subject and in some embodiments, the subject can be a human subject.

The present invention further provides a method of treating a neurological disorder or defect in a subject, comprising administering to the subject the virus vector of this invention, wherein the virus vector comprises a nucleic acid molecule that encodes a therapeutic protein or therapeutic RNA effective in treating the neurological disorder or defect. In some embodiments of this method, the virus vector is administered via an intracerebroventrical, intracisternal, intraparenchymal, intracranial and/or intrathecal route.

In further embodiments, the present invention provides a method of selectively transducing a cell having polysialic acid on the surface, comprising contacting the cell with a virus vector comprising an adeno-associated virus (AAV) serotype 4 (AAV4) capsid protein, wherein the capsid protein comprises a mutation at K492, K503 and N585.

Also provided herein is a method of delivering a nucleic acid molecule of interest (NOI) to a central nervous system progenitor cell and/or neuroblast, comprising contacting the progenitor cell and/or neuroblast with a virus vector comprising an adeno-associated virus (AAV) serotype 4 (AAV4) capsid protein, wherein the capsid protein comprises a mutation at K492, K503 and N585, and wherein the virus vector comprises the nucleic acid molecule of interest. In some embodiments of this method, the nucleic acid molecule of interest can encode a therapeutic protein or therapeutic RNA and in some embodiments, the central nervous system progenitor cell and/or neuroblast can be in a subject.

In additional embodiments of this invention, a method is provided of treating a neurological disorder or defect in a subject, comprising administering to the subject a virus vector comprising an adeno-associated virus (AAV) serotype 4 (AAV4) capsid protein, wherein the capsid protein comprises a mutation at K492, K503 and N585, and wherein the virus vector comprises a nucleic acid molecule that encodes a therapeutic protein or therapeutic RNA effective in treating the neurological disorder or defect. In some embodiments of this method, the virus vector is administered via an intracerebroventrical, intracisternal, intraparenchymal, intracranial and/or intrathecal route. In some embodiments of this method, the subject is a human subject.

Those skilled in the art will appreciate that for some AAV capsid proteins the corresponding modification will be an insertion and/or a substitution, depending on whether the corresponding amino acid positions are partially or completely present in the virus or, alternatively, are completely absent. Likewise, when modifying AAV other than AAV4, the specific amino acid position(s) may be different than the position in AAV4 (see, e.g., Table 4, which shows a representative example of amino acid residues corresponding to S257 in AAV4). As discussed elsewhere herein, the corresponding amino acid position(s) will be readily apparent to those skilled in the art using well-known techniques.

The modifications described above can be incorporated into the capsid proteins or capsids of the invention in combination with each other and/or with any other modification now known or later discovered.

TABLE 4

| Serotype | Position 1 | Position 2 |
|---|---|---|
| AAV1 | A263X | T265X |
| AAV2 | Q263X | –265X |
| AAV3a | Q263X | –265X |
| AAV3b | Q263X | –265X |
| AAV4 | S257X | –259X |
| AAV5 | G253X | V255X |
| AAV6 | A263X | T265X |
| AAV7 | E264X | A266X |
| AAV8 | G264X | S266X |
| AAV9 | S263X | S265X |

Where,
(X) → mutation to any amino acid
(–) → insertion of any amino acid
Note:
Position 2 inserts are indicated by the site of insertion The invention also encompasses virus vectors comprising the modified capsid proteins and capsids of the invention. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AAV capsid comprising a modified capsid subunit of the invention and a vector genome.

For example, in representative embodiments, the virus vector comprises: (a) a modified virus capsid (e.g., a modified AAV capsid) comprising a modified capsid protein of the invention; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid molecule encoding a protein or functional RNA of interest. Recombinant virus vectors are described in more detail below.

It will be understood by those skilled in the art that the modified capsid proteins, virus capsids and virus vectors of the invention exclude those capsid proteins, capsids and virus vectors that have the indicated amino acids at the specified positions in their native state (i.e., are not mutants). Methods of Producing Virus Vectors.

The present invention further provides methods of producing the inventive virus vectors. In one representative embodiment, the present invention provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the invention). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski (1992) *Curr. Top. Microbiol. Immun.* 158:67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al. (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al. ((2001) *Gene Ther.* 18:704-12) describes a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al. (1999) *Gene Therapy* 6:986 and WO 00/17377.

As a further alternative, the virus vectors of the invention can be produced in insect cells using baculovirus vectors to deliver the rep/cap genes and rAAV template as described, for example, by Urabe et al. (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors.

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses) or immunogenic (e.g., for vaccines) proteins and/or functional or therapeutic RNA molecules.

Therapeutic polypeptides include, but are not limited to, cystic fibrosis transmembrane regulator protein (CFTR), dystrophin (including mini- and micro-dystrophins, see, e.g, Vincent et al. (1993) *Nature Genetics* 5:130; U.S. Patent Publication No. 2003/017131; International publication WO/2008/088895, Wang et al. *Proc. Natl. Acad. Sci. USA* 97:13714-13719 (2000); and Gregorevic et al. *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al. (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factor α soluble receptor), S100A1, parvalbumin, adenylyl cyclase type 6, a molecule that modulates calcium handling (e.g., $SERCA_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al. *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al. (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al. (2000) *Science* 287:2431), and other non-translated RNAs, such as "guide" RNAs (Gorman et al. (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al. *J. Gene Med.* 10:132-142 (2008) and Li et al. *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al. (1994) Proc. Nat. Acad. Sci USA 91:8507; U.S. Pat. No. 5,916,563 to Young et al. U.S. Pat. No. 5,905,040 to Mazzara et al. U.S. Pat. Nos. 5,882,652, 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al. (1994) *Proc. Natl. Acad. Sci. USA* 91:3515; Kawakami et al., (1994) *J. Exp. Med.*, 180:347; Kawakami et al. (1994) *Cancer Res.* 54:3124), MART-1, gp100 MAGE-1, MAGE-2, MAGE-3, CEA, TRP-1, TRP-2, P-15, tyrosinase (Brichard et al. (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (α1-antitrypsin), Lesch-Nyhan Syndrome (hypoxanthine guanine phosphoribosyl transferase), Niemann-Pick disease (sphingomyelinase), Tay Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barka, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knock-down such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as TRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a virus vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or L1N28.

The invention can also be practiced to treat and/or prevent epilepsy, stroke, traumatic brain injury, cognitive disorders, behavioral disorders, psychiatric disorders, Huntington's disease, Alzheimer's disease, amyotrophic lateral sclerosis (ALS), as well as any other neurodegenerative condition that might benefit from or require axonal/neuronal regeneration or repair.

In particular embodiments, the present invention can be practiced to promote axonal regeneration and neuronal repair, restore circuits and/or replenish lost neurons as a corrective therapy, e.g., by targeted regulation or overexpression of stem cell differentiation and reprogramming factors such as FoxJ1, Fox2, NeuroD2, NG2 or Olig2 and/or microRNAs such as miR-137, MiR124, as well as any other factors or miRNAs implicated in neuronal development and differentiation.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration.

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the invention.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector and/or virus capsid to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^3$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector and/or virus capsid according to the present invention is administered to skeletal muscle, diaphragm muscle and/or cardiac muscle (e.g., to treat and/or prevent muscular dystrophy, heart disease [for example, PAD or congestive heart failure]).

The invention can also be practiced to produce antisense RNA, RNAi or other functional RNA (e.g., a ribozyme) for systemic delivery.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and virus capsids can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors.

Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis (ALS), progressive muscular atrophy, Pick's disease, muscular dystrophy, multiple sclerosis, myasthenia gravis, Binswanger's disease, trauma due to spinal cord and/or head injury (e.g., traumatic brain injury), Tay Sachs disease, Lesch-Nyan disease, epilepsy, stroke, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, any neurodegenerative condition that might benefit from or require axonal/neuronal regeneration and/or repair, cognitive disorders, behavioral disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intracerebroventricular, intracisternal, intraparenchymal, intracranial, intrathecal, intraocular, intracerebral, intraventricular, intravenous (e.g., in the presence of a sugar such as mannitol), intranasal, intraaural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

EXAMPLES

Example 1

Adeno-associated viruses (AAV) are thought to spread through the central nervous system (CNS) by exploiting cerebrospinal fluid (CSF) flux and hijacking axonal transport pathways. The role of host receptors that mediate these processes is not well understood. Here, we report polysialic acid (PSA), an indispensable marker for embryonic neurogenesis, as a novel regulator of AAV serotype 4 transport and tropism in the neonatal brain. Specifically, we describe a lab-derived AAV4 mutant that displays a switch in receptor specificity from sialic acid (SA) to polysialic acid (PSA). Upon intracranial injection into lateral ventricles of the neonatal mouse brain, we observed a striking shift in viral tropism from 2,3-linked SA+ ependymal lining to 2,8-linked PSA+ migrating progenitors in the rostral migratory stream and olfactory bulb. In addition, this gain-of-function phenotype correlates with robust CNS spread of the AAV4 mutant through paravascular transport pathways. Consistent with these observations, altering glycan dynamics within the brain by co-administering substrate-specific neuraminidases resulted in striking changes to the cellular tropisms and transduction efficiencies of both AAV4 as well as mutant virions. These studies indicate that glycan signatures associated with host development can regulate viral transport and tropism in the brain.

Viruses invade the CNS through various mechanisms. In the current study, we utilize AAV as a model to study the dynamics of virus-carbohydrate interactions in the developing brain and its impact on viral tropism. Specifically, we administered different AAV strains into the cerebrospinal fluid space within the brains of newborn mice. A mutant virus that displays a switch in receptor usage not only spreads across the entire brain, but is also redirected from cells lining the cerebrospinal fluid to migrating progenitor cells. Altering the carbohydrate content of the brain using specific enzymes confirms the differential influence of each receptor on viral spread and cellular tropism. These studies support the notion that carbohydrates can regulate viral infection at multiple levels in the brain.

Viruses enter the CNS by exploiting a variety of transport pathways that hinge on preliminary infection of peripheral nerve endings or through the blood by infecting circulating leukocytes or brain endothelial cells. Subsequent spread within the brain is achieved by axonal transport and trans-synaptic spread. A key step in viral entry into the CNS and subsequent directional transport is the recognition of specific cell surface membrane glycoproteins as receptors. For instance, polioviruses utilize CD155 as a receptor, while alpha herpesviruses exploit nectin-1 for CNS entry, both members of the immunoglobulin superfamily. Several membrane-associated components have also been implicated in Rabies virus CNS entry. Prior to engagement of such host membrane proteins, viruses often bind to cell surface glycans for attachment. One of the most versatile host glycans that have been exploited as viral attachment factors are the family of sialic acids (SA). For instance, SA receptors have been implicated in the neurovirulence of reovirus and polyomaviruses. Modulating SA binding affinity has also been shown to influence the pathogenicity of the neurovirulent strain of the minute virus of mice (MVM).

While no natural isolates from brain tissue have been reported thus far, adeno-associated viruses (AAV), which are helper-dependent parvoviruses, display a broad spectrum of CNS tropisms following intracranial or systemic administration in different hosts. The cellular tropisms of different AAV strains observed in these studies were mostly neuronal, with a few exceptions that can transduce astrocytes and glia as well. Similar to their helper viruses such as Adenoviridae or Herpesviridae, AAV strains undergo interstitial as well as axonal transport within the CNS. However, the molecular bases of this diversity in AAV transport mechanisms and CNS tropisms are not well understood. Within this framework, AAV isolates have been shown to utilize three different glycans—SA, galactose (GAL) and heparan sulfate (HS) for cell surface attachment. In addition, several growth factor receptors and integrins have been identified as being essential for AAV cell entry. Our lab and others have recently demonstrated the role of SA and GAL in determining the systemic fate of different AAV serotypes in mouse models.

The African green monkey isolate, AAV serotype 4 is one of the evolutionarily and structurally most distinct serotypes known to date and displays selective tropism for the ependymal lining following intra-cerebroventricular (ICV) administration in neonatal and adult mice. In addition, AAV4 particles directly injected into the sub-ventricular zone can transduce astrocytes forming glial tubes within the RMS. The functional cell surface attachment factor for AAV4 is O-linked $\alpha 2,3$-SA (mucin). We previously identified a novel AAV4 mutant (AAV4.18) that displays decreased affinity towards 2,3-SA and a transduction-deficient phenotype following systemic administration in mice. In the current study, we identify a novel glycan that differentially regulates the CNS transport and cellular tropism of AAV4 and the lab-derived mutant strain. Unlike AAV4, which displays restricted tropism for the ependymal lining, the lab-derived AAV4.18 mutant spreads throughout the brain parenchyma and can selectively infect migrating progenitors in the rostral and caudal directions from a unilateral ICV injection in neonatal mice. Further biochemical characterization of AAV4 and AAV4.18 in the mouse brain confirmed a switch in receptor specificity from $\alpha 2,3$-linked SA to $\alpha 2,8$-linked polysialic acid (PSA), a well-established marker of neurogenesis.

Figure 2:
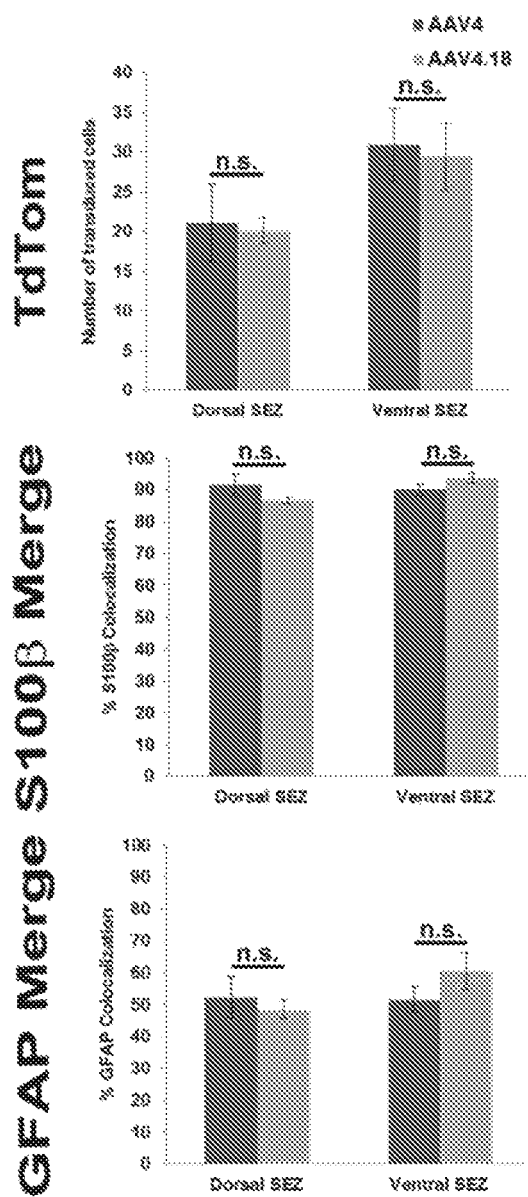
FIG. 2. Similar ependymal tropism of AAV4 and the AAV4.18 mutant.

The AAV4.18 mutant displays expanded tropism for migrating progenitors. Neuronal progenitors in the SEZ are known to migrate via the RMS to the OB, where they differentiate into interneurons of the granular and periglomerular layers in developing and adult rodent brains. Confocal microscopy analysis of sagittal sections of postnatal mouse brains imaged at 2 weeks post-injection revealed strikingly distinct patterns of transduction between AAV4 and AAV4.18 vectors. Notably, AAV4.18 injected mice showed significantly more tdTom expression in the RMS and OB (~3 and 6 fold increase respectively, n=4 mice) regions as compared to AAV4 injected mice. We then performed immunostaining for the migrating neuroblast marker doublecortin (Dcx) and proliferating cell marker phospho-histone H3 (PH3) to assess the cell types associated with the tdTom expression in the RMS and OB. tdTom+ cells within the RMS and the OB in AAV4.18 injected mouse brains show significantly increased colocalization with Dcx+ cells compared to AAV4 injected brains. A similar trend showing increased colocalization of tdTom+ expression with the PH3+ cells was observed in the RMS and to a lesser level in the OB of 4.18 injected brains. These observations were corroborated by quantitative and statistical analyses (FIG. 1; $p<0.05$). Despite these striking differences in the RMS and OB, both parental and mutant strains displayed similar gene expression (tdTom+) profiles in the sub-ependymal zone (SEZ) (FIG. 2). Specifically, immuno-colocalization studies with markers for ependymal cells (S100$\beta$ and astrocytes (GFAP) revealed that both AAV4 and AAV4.18 transduced S100$\beta$+ and GFAP+ cells in the ependymal lining with high, yet similar efficiency (FIG. 2) It is also noteworthy to mention that similar transduction profiles and ependymal tropism were observed in adult mouse brains.

Mutant AAV4.18 virions display enhanced CNS spread. In order to understand the mechanisms underlying the selective tropism of AAV4.18 for progenitors and neuroblasts in the postnatal CNS, we tracked the distribution of each AAV vector in the mouse brain parenchyma following ICV injections. To achieve this, we injected AAV vectors packaging genomes that were labeled with the thymidine analog bromodeoxyuridine (BrdU) through ICV injections in neonatal mice. Brains were harvested as early as 2 hours post vector administration and immunostained with an anti-BrdU antibody to visualize the biodistribution of AAV genomes in the brain parenchyma. AAV4 injected mice exhibit robust BrdU staining in the immediate vicinity of the site of injection in the SEZ and the outer meninges of the neonatal brain, presumably due to CSF transport. In contrast, the AAV4.18 vector shows a remarkably diffuse distribution pattern of BrdU-labeled viral particles not only in the SEZ but also through the brain parenchyma and particularly in the cortical regions. Immunostaining analysis of brain sections with the endothelial cell marker CD31 revealed BrdU+ AAV4.18 genomes arranged alongside CD31+ processes in the cortical regions of the mouse brain. In contrast, AAV4 genomes did not show this phenotype in the cortex. It should be noted that despite the expanded spread of the AAV4.18 genomes, complete colocalization with endothelial cells was not observed. This suggests that the selective tropism for migrating progenitors can, in part, be attributed to the ability of AAV4.18 to spread across the neonatal brain parenchyma.

Ependymal transduction by the AAV4.18 mutant is only partially dependent on sialic acid (SA). In order to dissect capsid-receptor interactions that mediate the differential transduction profiles of AAV4 and 4.18 strains, we enzymatically removed terminal SA from cell surface sialoglycans in P0 mouse brains. Specifically, the enzyme neuraminidase III cleaves terminal 2,3- and 2,6-linked SA, the former being the cognate cell attachment factor for the parental AAV4 strain. In order to assess the impact of this treatment on the cell-surface glycan architecture of the mouse brain, we immunostained the sagittal sections with fluorescein isothiocyanate (FITC)-labeled jacalin, which binds O-linked sialic acid moieties. At 2 weeks post ICV administration, neuraminidase co-injection completely abrogates tdTom expression in ependymal cells and choroid plexus of AAV4 injected mice, which correlates with the loss of jacalin staining in these brains. This result suggests that AAV4 utilizes alpha2,3-linked and/or alpha2,6-linked sialic acids for transduction in the neonatal mouse brain. In contrast, AAV4.18-mediated tdTom expression of the ependymal lining is only partially abrogated by this selective enzymatic treatment. We further observed that AAV4.18 transduces ependymal cells in the absence of jacalin+ staining. These results indicate that the AAV4.18 mutant has potentially acquired a sialic acid-independent mechanism to transduce the ependymal lining and choroid plexus in the neonatal mouse brain.

The mutant AAV4.18 strain displays a switch in receptor specificity to the neurogenesis biomarker, polysialic acid (PSA). The polysialylated form (PSA, alpha2,8-linked sialic acids) of neural cell adhesion molecule (NCAM) is expressed in migrating progenitor cells of the RMS during OB neurogenesis. PSA-NCAM plays a pivotal role in mediating rostral migration of olfactory bulb precursor cells whereas deficiencies in either PSA or NCAM cause accumulation of progenitor cells in the SEZ and RMS resulting in aberrant olfactory histogenesis. In order to dissect the possible mechanism underlying this switch in viral tropism from ependymal cells to migrating neuroblasts, we selectively modulated the sialoglycan composition of the neonatal mouse brain. We compared the effects of two different enzymes—neuraminidase III (described earlier) or endoneuraminidase-N, which selectively cleaves 2,8-linked polysialic acid (PSA). In a manner similar to untreated controls, co-injection of neuraminidase III did not alter the extent of co-localization between tdTom+ and PSA-NCAM+ cells in the RMS or the OB in the AAV4.18 injected mouse brain. In contrast, co-administration of endoneuraminidase-N, which cleaves 2,8-linked PSA resulted in a complete loss of tdTom reporter gene expression in AAV4.18 injected mouse brains. This observation was further corroborated by the loss of PSA-NCAM staining along the migrating progenitor continuum in these mice. Taken together, these results support the notion that the AAV4.18 has undergone a switch in glycan receptor specificity from 2,3-linked SA to 2,8-linked PSA and requires the latter glycan for transducing neuroblasts in the developing brain.

Further characterization of the cellular tropism of AAV4.18 vectors revealed a clear correlation between tdTom+ cells and PSA-NCAM immunostaining along the progenitor migration continuum in the RMS and OB. No apparent colocalization was observed with the mature neuronal marker, NeuN in the PSA-NCAM labeled region, but several tdTom+ cells along the migratory pathway co-localized with the astrocyte marker, GFAP in the RMS and OB and were closely associated with RC2/Nestin immunostained processes. Characterization of tdTom+ migratory progenitors in the caudal direction yielded similar results. Thus, AAV4.18 has clearly acquired the capacity to potentially transduce PSA-NCAM+ migrating neuroblasts as well as the cells within the surrounding GFAP+ meshwork of glial tubes in the SEZ-RMS-OB continuum.

Similar assessment of the parental AAV4 strain in the RMS and OB revealed minimal transduction of migrating progenitors with or without neuraminidase III treatment. In contrast, while endoneuraminidase-N treatment completely abrogated AAV4.18 transduction in the RMS and OB, parental AAV4 virions displayed an expanded ability to transduce cells in the OB, but not the RMS. Immunocolocalization studies performed on sagittal sections from these mice showed significant transgene expression (td-Tom+) in NeuN+ cells in the OB. These results indirectly support the notion that 2,8-linked PSA negatively regulates AAV4 spread and blocks transduction by competing for 2,3-linked SA binding sites on the AAV4 capsid.

Successful infection by parvoviruses such as AAV involves a series of carefully orchestrated events including cell surface receptor binding, endocytic uptake, capsid uncoating, nuclear entry and genome release followed by second strand synthesis and subsequent transcription. The first step, i.e., parvoviral attachment to the host cell surface is mediated by different glycans. In the brain, AAV capsid interactions with heparan sulfate (HS) have been particularly well-studied. Direct parenchymal injection of AAV serotype 2, which utilizes HS as a primary receptor, results in a prominently neuronal transduction profile. Co-injection of soluble heparin has been shown to improve the CNS spread and consequently transduction efficiency of AAV2 following intracranial injections in rodent models. The ability to bind HS also appears to restrict the CNS transduction profile of AAV serotype 6. However, this effect can be reversed in part by mutating a lysine residue (K531) on the capsid surface, which abolishes HS binding. These earlier studies highlight the potential for glycan expression patterns to regulate viral spread and tropism in the brain.

In the current study, we have characterized a novel AAV mutant that selectively transduces migrating progenitors in the neonatal mouse brain. This mutant was originally discovered from a randomly mutated AAV4 capsid library and characterized as an SA-binding deficient mutant. When administered systemically, the AAV4.18 mutant displays attenuated cardiopulmonary tropism in mice due to the low binding affinity towards O-linked 2,3-SA, the cognate receptor for the parental AAV4 serotype. In the neonatal mouse brain, the natural isolate AAV4 exclusively transduces ependymal cells following ventricular injection. Interestingly, when injected directly into the SEZ, AAV4 can transduce type B astrocytes in the SVZ and glia overlying the RMS. Our results now show that this dichotomy potentially arises from the high SA binding affinity of AAV4 capsids, which likely restricts transduction to the ependymal lining following ICV administration. In contrast, the low affinity AAV4.18 mutant can penetrate the ependymal barrier into the brain parenchyma following a single ICV injection and selectively transduce migrating neuroblasts and proliferating cells. It is noteworthy that the enhanced spread of AAV4.18 particles to distal regions of the mouse brain does not result in successful transduction of mature neurons within these regions. Rather, immunohistochemical analysis suggests that AAV4.18 particles that reach the cortex are closely associated with the brain microvasculature without actually transducing endothelial cells. This observation suggests that interstitial solutes such as viral particles might exploit paravenous efflux or the ‘glymphatic’ clearance pathway. Correspondingly, we postulate that AAV4.18 particles, loosely bound to SA are more likely to be affected by interstitial fluid transport through white matter tracts and perivascular spaces leading to enhanced penetration of brain parenchyma. We further expanded these findings by evaluating the effect of selective enzymatic removal of 2,3- or 2,8-linked SA from the murine brain by ICV injection of substrate-specific neuraminidases. While AAV4 transduction is completely abrogated by the earlier treatment, AAV4.18 transduction of a subset of cells in the ependymal wall, the choroid plexus and migrating progenitors that stain positive for polysialylated NCAM remains unaffected. This switch in glycan receptor usage by AAV4.18 was clearly demonstrated when selective cleavage of 2,8-linked SA led to a complete loss of AAV4.18 transduction in the mouse brain. Taken together, these results support the notion that AAV4.18 can not only spread throughout the brain parenchyma, but also selectively exploit PSA (2,8-linked SA) to transduce postnatal migrating progenitors in the mouse forebrain.

The expanded receptor usage and selective cellular tropism displayed by AAV4.18 particles are not a mere coincidence. It is well known that the linear homopolymer of alpha 2,8-linked sialic acid (polysialic acid/PSA) plays an indispensable role in embryonic and adult neurogenesis. Two regions of the brain, namely OB and hippocampal dentate gyrus are persistently neurogenic and undergo constant progenitor chain migration into adulthood in rodents. Despite multiple differences between adult and embryonic neurogeneses, consistent PSA-NCAM expression is a feature observed in both of these regions through adulthood. The biochemical properties of PSA make it a potent negative regulator of cell-cell adhesion. This is important for successful migration of precursor cells during neurogenesis. This is potentially the reason PSA-NCAM is highly expressed in the neuronal precursor cells during olfactory neurogenesis. Furthermore, the enzymatic removal of PSA using endoneuraminidase-N treatment disrupts the RMS leading to neuroblast dispersion to unspecific regions like cortex and striatum. Thus, the selective transduction of migrating progenitors by AAV4.18 can be directly attributed to the expression patterns of this unique glycan attachment factor that can vary with the developmental stage of the host organism.

PSA does not appear to functionally influence the tropism or transduction efficiency of AV4 or related mutants in physiological settings other than the CNS, such as in cell culture or systemic organs such as the heart and lung following intravenous administration. It is likely that the developing brain provides a unique setting for this novel virus-glycan interaction. Secondly, the structural coordinates that mediate PSA recognition by AAV4 and the mutant virion remain to be determined. Preliminary structural modeling revealed altered surface electrostatics for the AAV4.18 mutant in comparison with the parental AAV4 strain. It is tempting to speculate that manipulation of capsid surface charge density might decrease affinity for branched or linear 2,3-linked SA glycans, while simultaneously imparting the expanded potential to recognize the negatively charged PSA glycopolymer. Our overall approach helps understand the functional implications of altering virus-glycan interactions in the CNS, impact of developmentally regulated glycan expression profiles on virus neurotropism and simultaneously provides a roadmap for engineering viruses to favor certain glycan architectures for gene transfer applications in the brain.

Recombinant AAV vector production. Recombinant AAV4 and mutant AAV4.18 vectors were generated using an updated triple plasmid transfection method. Briefly, this involved transfection of (a) the pXR4 helper plasmid or the mutant pXR4.18 helper plasmid; (b) the adenoviral helper plasmid pXX6-80; and (c) the pTR-CBA-tdTom plasmid encoding the tdTomato (tdTom) reporter gene driven by the chicken beta actin (CBA) promoter and flanked by inverted terminal repeats (ITRs) derived from the AAV2 genome. Vector purification was carried out using cesium gradient ultracentrifugation and viral titers obtained by quantitative PCR using a Roche Lightcycler® 480 (Roche Applied Sciences, Pleasanton, Calif.) with primers (IDT Technologies, Ames, Iowa) designed for the CBA promoter (forward, 5'-CGT CAA TGG GTG GAG TAT TT-3' (SEQ ID NO:34); reverse, 5'-GCG ATG ACT AAT ACG TAG ATG-3' (SEQ ID NO:35)).

In order to generate AAV particles packaging thymidine analog 5-bromo-2'-deoxyuridine (BrdU) labeled genomes, we adapted a modified vector production protocol. Briefly, at 1 hr post triple plasmid transfection, HEK293 producer cells were treated with a 10:1 molar mixture of BrdU and 5-fluoro-2'-deoxyuridine at a final concentration of 10 μg BrdU/ml of media (Invitrogen, Camarillo, Calif.). Vectors packaging BrdU-labeled genomes were purified and quantified as described above.

Intracerebroventricular (ICV) injections. All animal experiments were carried out with Balb/c mice bred and maintained in accordance to NIH guidelines and as approved by the UNC Institutional Animal Care and Use Committee (IACUC). Neonatal P0 pups were rapidly anesthetized by hypothermia by placing on ice for 1 min followed by stereotaxic intraventricular cerebral injections. A Hamilton 700 series syringe with a 26s gauge needle (Sigma-Aldrich, St. Louis, Mo.) was attached to a KOPF-900 small animal stereotaxic instrument (KOPF instruments, Tujunga, Calif.) and the mice injected unilaterally in their left lateral ventricle with a dose of 1×10⁹ particles (volume 3 µl) of AAV4 or AAV4.18 vectors packaging the CBA-tdTom reporter cassette. Developing mouse brains (P14) were harvested, post-fixed and immunostained as described below. For tracking bromodeoxyuridine (BrdU)-labeled viruses, 7.4×10⁸ vector genome-containing particles in a volume of 5 µL were injected into the left lateral ventricle of P0 mice. Neonatal brains were harvested 2 hours post-injection, post-fixed in paraformaldehyde, sectioned and immunostained as described below. For recombinant sialidase co-injection experiments, the vectors were mixed with either 5.2 mU of Neuraminidase type III (Sialidase, Sigma-Aldrich, St. Louis, Mo.) or 1.45 U of Endoneuraminidase-N (ABC Scientific, Los Angeles, Calif.) to a total injection volume of 4.3 µl. All neonatal injections were performed 0.5 mm relative to the sagittal sinus, 2 mm rostral to transverse sinus and 1.5 mm deep. Following vector administration, mice were revived under a heat lamp and rubbed in the bedding before being placed back with the dam.

Tissue processing, confocal microscopy and immunofluorescence analysis. Two week old mice were sacrificed with an overdose of tribromoethanol (avertin) (0.2 ml/10 g of 1.25% solution) followed by transcardial perfusion of 4% paraformaldehyde in PBS. The brains were removed and post-fixed for 24 hr and 50 µm thick sections obtained using a Leica VT 1000S vibrating blade microtome (Leica VT 1000S, Leica Biosystems, IL). Free floating brain sections were blocked in 10% goat serum and 1% Triton X (Sigma-Aldrich, St. Louis, Mo.) in PBS for 1 hr prior to overnight incubation with primary monoclonal antibodies at 4° C. The following primary antibodies were utilized: rabbit anti-S100β (Sigma, 1:1000), mouse anti-GFAP (Abcam, 1:1000), guinea pig anti-Dcx (Abcam, 1:1000), goat anti-phospho-histone H3 (Millipore, 1:1000), mouse anti-BrdU (Invitrogen-033900, 1:2500), rabbit anti-NeuN (Abcam, 1:750), mouse anti PSA-NCAM (DSHB, 1:750) and mouse anti-Rc2/Nestin (DSHB, 1:750). Secondary antibodies were raised in goats and conjugated to Alexa 488 or Alexa 647 (Abcam, 1:500). For jacalin staining, we followed the blocking step with 1.5 hour incubation of free floating mouse brain sections in FITC-Jacalin at room temperature (Vector-labs, Burlingame, Calif., 1:40). Jacalin was diluted to a working concentration of 20 µg/ml in 3% goat serum in PBS-T. Immunostained brain sections were visualized using a Zeiss CLSM 700 confocal laser scanning microscope and analyzed with Zen® Black software. Colocalization (%) of tdTomato reporter expression with different cell type specific markers were derived from the ratio of the number of transduced cells (tdTom+) that were S100β/GFAP/Dcx/PH3+ and the total number of transduced cells (tdTom+). Cells were counted in non-overlapping fields of view of 200 µm² area in the subependymal zone, rostral migratory stream, olfactory bulb or other pertinent regions in the P14 mouse brain.

Example 2

Surface loop domains on the AAV4 capsid were selected for further iterative modification through a process of random mutagenesis and selection in the brain following intracerebroventricular injections. These $2^{nd}$ generation mutants were generated using AAV4.18 as the original template capsid. Thus, these mutants contain at least the mutations K492E and K503E. In some embodiments, these mutants contain different amino acid substitutions at the N585 residue including N585S or N585R. A total of few new, $2^{nd}$ generation mutants were identified through this process. These clones displayed cellular tropisms that can be categorized as (i) similar to AAV4.18 (mutants 6a, 5a, 5b) or (ii) expanded progenitor cell tropism with higher transduction efficiency (mutants 6b, 6c).

This panel of mutants provides reagents for high efficiency gene transfer in the CNS selectively to ependymal cells, choroid plexus, migrating progenitors in the rostral and caudal migratory streams, olfactory bulb, cortex and hippocampal regions. They expand the $1^{st}$ generation mutant, AAV4.18 to a panel of reagents available for gene therapy of various CNS indications including stroke, epilepsy, neurodegeneration, brain arterio-venous malformations, lysosomal storage disorders and other diseases. Table 5 summarizes the results of different mutants following CNS injection. Green fluorescence protein (GFP) expression is indicated by a scoring system as described in the table.

The foregoing is illustrative of the present invention, and is not to be construed as limiting thereof. The invention is defined by the following claims, with equivalents of the claims to be included therein.

---

SEQUENCES

AAV4 capside protein (GenBank Accession No. NP_044927, SEQ ID NO: 1)
MTDGLYPDWLEDNLSEGVREWWALQPGAPKPKANQQHQDNARGLVLPGYKYLGPGNGLDKGE
PVNAADAAALEHDKAYDQQLKAGDNPYLKYNHADAEFQQRLQGDTSFGGNLGRAVFQAKKRV
LEPLGLVEQAGETAPGKKRPLIESPQQPDSSTGIGKKGKQPAKKKLVFEDETGAGDGPPEGS
TSGAMSDDSEMRAAAGGAAVEGGQGADGVGNASGDWHCDSTWSEGHVTTTSTRTWVLPTYNN
HLYKRLGESLQSNTYNGFSTPWGYFDFNRFHCHFSPRDWQRLINNNWGMRPKAMRVKIFNIQ
VKEVTTSNGETTVANNLTSTVQIFADSSYELPYVMDAGQEGSLPPFPNDVFMVPQYGYCGLV
TGNTSQQQTDRNAFYCLEYFPSQMLRTGNNFEITYSFEKVPFHSMYAHSQSLDRLMNPLIDQ

YLWGLQSTTTGTTLNAGTATTNFTKLRPTNFSNFKKNWLPGPSIKQQGFSKTANQNYKIPAT

GSDSLIKYETHSTLDGRWSALTPGPPMATAGPADSKFSNSQLIFAGPKQNGNTATVPGTLIF

TSEEELAATNATDTDMQGNLPGGDQSNSNLPTVDRETALGAVPGMVWQNRDIYYQGPIWAKI

PHTDGHFPSPLIGGFGLKHPPPQIFIKNTPVPANPATTFSSTPVNSFITQYSTGQVSVQID
WEIQKERSKRWNPEVQFTSNYGQQNSLLWAPDAAGKYTEPRAIGTRYLTHHL

-continued

SEQUENCES

AAV4 Protein Sequence (SEQ ID NO: 2):
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNYKIPA
TGSDSLIKYETHSTLDGRWSALTPGPPMATAGPADSKFSNSQLIFAGPKQNGNTATVPGTLI
FTSEEELAATNATDTDMWGNLPGGDQSNSNLPTVDRLTALGAVPGMVWQNRDIYYQGPIWAK
IPHTDGHFHPSPLIGGFGLKHPPPQIFIKNTPVPANPATTFSSTPVNSFITQYSTGQVSVQI
DWEIQKERSKRWNPEVQFTSNYGQQNSLLWAPDAAGKYTEPRAIGTRYLTHHL Aav4_14 (SEQ ID NO: 3)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID QYLWGLQSTTTGTTLNAGTATTNFTKLRPTNFSNFKKNWLPGPSIKQQGFSKTANQNyiipa tgsdslixyethstldgrwsaltpgppmatagpadskfsnsqlifagpkqngntatvpgtli ftseeelaatnatdtdmwgnlpggdsssnlptvdrtplgavpgmvwqnrdiyypgpiwak iphtdghfhpspliggfglkhpppqifikntpvpanpattfsstpvnsfitqystgqvsvqi
dweiqkerskrwnpevqftsnygqqnsllwapdaagkytepraigtrylthhl Aav4_40 (SEQ ID NO: 4)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID QYLWGLQSTTTGTTLNAGTATTNFTKLRPTNFSNFKKNWLPGPSIKQQGFSKTANQNyyipa tgsdsliiyethstldgrwsaltpgppmatagpadskfsnsqlifagpkqngntatvpgtli ftseeelaatnatdtdmwgnlpggdqssnlptvdrtalgavpgmvwqnrdiyyqgpiwak iphtdghfhpspliggfglkhpppqifikntpvpanpattfsstpvnsfitqystgqvsvqi
dweiqkerskrwnpevqftsnygqqnsllwapdaagkytepraigtrylthhl
same as wt downstream of matag Aav4_2 (SEQ ID NO: 5)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNygipa
tgsdslikyethstldgrwsaltpgppiatagpadskfsnsqlifagpkqngntatvpgtli
ftseeelaatnatdtdmwgnlplydassnlptvdrltllgavpgmvwqnrdiyyqgpiwak
iphtdghfhpspliggfglkhpppqifikntpvpanpattfsstpvnsfitqystgqvsvqi
dweiqkerskrwnpevqftsnygqqnsllwapdaagkytepraigtrylthhl Aav4_3 (SEQ ID NO: 6)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID

| SEQUENCES |
| --- |

QYLWGLQSTTTGTTLNAGTATTNFTKLRPTNFSNFKKNWLPGPSIKQQGFSKTANQNytipa
tgsdslityethstldgrwsaltpgppgatagpadskfsnsqlifagpkqngntatvpgtli
ftseeelaatnatdtdmwgnlprvdtsasnlptvdrytnlgavpgmvwqnrdiyyqgpiwak
iphtdghfpspliggfglkhpppqifikntpvpanpattfsstpvnsfitqystgqvsvqi
dweiqkerskrwnpevqftsnygqqnsllwapdaagkytepraigtrylthhl Aav4_10 (SEQ ID NO: 7)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNysipa
tgsdslikyethstldgrwsaltpgppfatagpadskfsnsqlifagpkqngntatvpgtli
ftseeekaatbatdtdmwgnlpdydsslsnlptvdrdttlgavpgmvwqnrdiyyqgpiwak
iphtdghfpspliggfglkhpppqifikntpvpanpattfsstpvnsfitqystgqvsvqi
dweiqkerskrwnpevqftsnygqqnsllwapdaagkytepraigtrylthhl Aav4_13 (SEQ ID NO: 8)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNysipa
tgsdsliwyethstldgrwsaltpgppcatagpadskfsnsqlifagpkqngntatvpgtli
ftseeelaatnatdtdmwgnlpqgdsslsnlptvdrmtvlgavpgmvwqnrdiyyqgpiwak
iphtdghfpspliggfglkhpppqifikntpvpanpattfsstpvnsfitqystgqvsvqi
dweiqkerskrwnpevqftsnygqqnsllwapdaagkytepraigtrylthhl Aav4_14 (SEQ ID NO: 3)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID QYLWGLQSTTTGTTLNAGTATTNFTKLRPTNFSNFKKNWLPGPSIKQQGFSKTANQNyiipa tgsdsliryethstldgrwsaltpgppmatagpadskfsnsqlifagpkqngntatvpgtli
ftseeelaatnatdtdmwgnlpfrdlsssnlptvdrstplgavpgmvwqnrdiyyqgpiwak
iphtdghfpspliggfglkhpppqifikntpvpanpattfsstpvnsfitqystgqvsvqi
dweiqkerskrwnpevqftsnygqqnsllwapdaagkytepraigtrylthhl Aav4_20 (SEQ ID NO: 9)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNycipa
tgsdsliryethstldgrwsaltpgpplatagpadskfsnsqlifagpkqngntatvpgtli
ftseeelaatnatdtdmwgnlpykdssrsnlptvdretslgavpgmvwqnrdiyyqgpiwak
iphtdghfpspliggfglkhpppqifikntpvpanpattfsstpvnsfitqystgqvsvqi
dweiqkerskrwnpevqftsnygqqnsllwapdaagkytepraigtrylthhl Aav4_22 (SEQ ID NO: 10)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNyiipa
tgsdsliyyethstldgrwsaltpgppratagpadskfsnsqlifagpkqngntatvpgtli
ftseeelaatnatdtdmwgnlpwidnsrsnlptvdrptslgavpgmvwqnkniyyqgpiwak
iphtdghfpspliggfglkhpppqifikntpvpanpattfstpvnsfitqystgqvsvqi
dweiqkerskrwnpevqftsnygqqnsllwapdaagkytepraigtrylthhl

SEQUENCES

Aav4_27 (SEQ ID NO: 11)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNygipa
tgsdsliiyethstldgrwsaltpgppratagpadskfsnsqlifagpkqngntatvpgtli
ftseeelaatnatdtdmwgnlpggdqsnsnlptvdrltalgavpgmvwqnrdiyyqgpiwak
iphtdghfhpspliggfglkhpppqifikntpvpanpattfsstpvnsfitqystgqvsvqi
dweiqkerskrwnpevqftsnygqqnsllwapdaagkytepraigtrylthhl Aav4_28 (SEQ ID NO: 12)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNyvipa
tesdsliyyethstldgrwsaltpgppyatagpadskfsnsqlifagpkqngntatvpgtli
ftseeelaatnatdtdmwgnlpprddstsnlptvdrktylgavpgmvwqnrdiyyqgpiwak
iphtdghfhpspliggfglkhpppqifikntpvpanpattfsstpvnsfitqystgqvsvqi
dweiqkerskrwnpevqftsnygqqnsllwapdaagkytepraigtrylthhl Aav4_31 (SEQ ID NO: 13)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNyyipa
tgsdsliiyethstldgrwsaltpgppiatagpadskfsnsqlifagpkqngntatvpgtli
ftseeelaatnstdtdmwgnlptdddsrsnlptvdrmtllgavpgmvwqnrdiyyqgpiwak
iphtdghfhpspliggfglkhpppqifikntpvpanpattfsstpvnsfitqystgqvsvqi
dweiqkerskrwnpevqftsnygqqnsllwapdaagkytepraigtrylthhl Aav4_39 (SEQ ID NO: 14)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNyhipa
tgsdsliyyethstldgrwsaltpgppsatagpadskfsnsqlifagpkqngntatvpgtli
ftseeelaatnatdtdmwgnlprrdssvsnlptvdrytdlgavpgmvwqnrdiyyqgpiwak
iphtdghfhpspliggfglkhpppqifikntpvpanpattfsstpvnsfitqystgqvsvqi
dweiqkerskrwnpevqftsnygqqnsllwapdaagkytepraigtrylthhl Aav4_40 (SEQ ID NO: 4)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNyyipa
tgsdslilyethstldgrwsaltpgppmatagpadskfsnsqlifagpkqngntatvpgtli
ftseeelaatnatdtdmwgnlpggdqsnsnlptvdrltalgavpgmvwqnrdiyyqgpiwak
iphtdghfhpspliggfglkhpppqifikntpvpanpattfsstpvnsfitqystgqvsvqi
dweiqkerskrwnpevqftsnygqqnsllwapdaagkytepraigtrylthhl Aav4_43 (SEQ ID NO: 15)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI

| SEQUENCES |
|---|
| QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br>QYLWGLQSTTTGTTLNAGTATTNFTKLRPTNFSNFKKNWLPGPSIKQQGFSKTANQNysipa<br>tgsdslisyethstldgrwsaltpgppratagpadskfsnsqlifagpkqngntatvpgtli<br>ftseeelaatnatdtdmwgnlprhdsslsnlptvdrntglgavpgmvwqnrdiyyqgpiwak<br>iphtdghfhpspliggfglkhpppqifikntpvpanpattfsstpvnsfitqystgqvsvqi<br>dweiqkerskrwnpevqftsnygqqnsllwapdaagkytepraigtrylthhl<br><br>Aav4_46 (SEQ ID NO: 16)<br>MAADGYLPDWLEDNLSEGVREWWALQPGAPKPKANQQHQDNARGLVLPGYKYLGPGNGLDKG<br>EPVNAADAAALEHDKAYDQQLKAGDNPYLKYNHADAEFQQRLQGDTSFGGNLGRAVFQAKKR<br>VLEPLGLVEQAGETAPGKKRPLIESPQQPDSSTGIGKKGKQPAKKKLVFEDETGAGDGPPEG<br>STSGAMSDDSEMRAAAGGAAVEGGQGADGVGNASGDWHCDSTWSEGHVTTTSTRTWVLPTYN<br>NHLYKRLGESLQSNTYNGFSTPWGYFDFNRFHCHFSPRDWQRLINNNWGMRPKAMRVKIFNI<br>QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br>QYLWGLQSTTTGTTLNAGTATTNFTKLRPTNFSNFKKNWLPGPSIKQQGFSKTANQNyfipa<br>tgsdsliryethstldgrwsaltpgpplatagpadskfsnsqlifagpkqngntatvpgtli<br>ftseeelaatnatdtdmwgnlpvidfsksnlptvdrlthlgavpgmvwqnrdiyyqgpiwak<br>iphtdghfhpspliggfglkhpppqifikntpvpanpattfsstpvnsfitqystgqvsvqi<br>dweiqkerskrwnpevqftsnygqqnsllwapdaagkytepraigtrylthhl<br><br>Aav4_49 (SEQ ID NO: 17)<br>MAADGYLPDWLEDNLSEGVREWWALQPGAPKPKANQQHQDNARGLVLPGYKYLGPGNGLDKG<br>EPVNAADAAALEHDKAYDQQLKAGDNPYLKYNHADAEFQQRLQGDTSFGGNLGRAVFQAKKR<br>VLEPLGLVEQAGETAPGKKRPLIESPQQPDSSTGIGKKGKQPAKKKLVFEDETGAGDGPPEG<br>STSGAMSDDSEMRAAAGGAAVEGGQGADGVGNASGDWHCDSTWSEGHVTTTSTRTWVLPTYN<br>NHLYKRLGESLQSNTYNGFSTPWGYFDFNRFHCHFSPRDWQRLINNNWGMRPKAMRVKIFNI<br>QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br>QYLWGLQSTTTGTTLNAGTATTNFTKLRPTNFSNFKKNWLPGPSIKQQGFSKTANQNykipa<br>tgsdslikyethstldgrwsaltpgppmatagpadskfsnsqlifagpkqngntatvpgtli<br>ftseeelaatnatdtdmwgnlpvrdfslsnlptvdrttklgavpgmvwqnrdiyyqgpiwak<br>iphtdghfhpspliggfglkhpppqifikntpvpanpattfsstpvnsfitqystgqvsvqi<br>dweiqkerskrwnpevqftsnygqqnsllwapdaagkytepraigtrylthhl<br><br>Aav4_60 (SEQ ID NO: 18)<br>MAADGYLPDWLEDNLSEGVREWWALQPGAPKPKANQQHQDNARGLVLPGYKYLGPGNGLDKG<br>EPVNAADAAALEHDKAYDQQLKAGDNPYLKYNHADAEFQQRLQGDTSFGGNLGRAVFQAKKR<br>VLEPLGLVEQAGETAPGKKRPLIESPQQPDSSTGIGKKGKQPAKKKLVFEDETGAGDGPPEG<br>STSGAMSDDSEMRAAAGGAAVEGGQGADGVGNASGDWHCDSTWSEGHVTTTSTRTWVLPTYN<br>NHLYKRLGESLQSNTYNGFSTPWGYFDFNRFHCHFSPRDWQRLINNNWGMRPKAMRVKIFNI<br>QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br>QYLWGLQSTTTGTTLNAGTATTNFTKLRPTNFSNFKKNWLPGPSIKQQGFSKTANQNyfipa<br>tgsdsliqyethstldgrwsaltpgppmatagpadskfsnsqlifagpkqngntatvpgtli<br>ftseeelaatnatdtdmwgnlpggdqsnsnlptvdrltalgavpgmvwqnrdiyyqgpiwak<br>iphtdghfhpspliggfglkhpppqifikntpvpanpattfsstpvnsfitqystgqvsvqi<br>dweiqkerskrwnpevqftsnyqqnsllwapdaagkytepraigtrylthhl<br><br>Aav4_63 (SEQ ID NO: 19)<br>MAADGYLPDWLEDNLSEGVREWWALQPGAPKPKANQQHQDNARGLVLPGYKYLGPGNGLDKG<br>EPVNAADAAALEHDKAYDQQLKAGDNPYLKYNHADAEFQQRLQGDTSFGGNLGRAVFQAKKR<br>VLEPLGLVEQAGETAPGKKRPLIESPQQPDSSTGIGKKGKQPAKKKLVFEDETGAGDGPPEG<br>STSGAMSDDSEMRAAAGGAAVEGGQGADGVGNASGDWHCDSTWSEGHVTTTSTRTWVLPTYN<br>NHLYKRLGESLQSNTYNGFSTPWGYFDFNRFHCHFSPRDWQRLINNNWGMRPKAMRVKIFNI<br>QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br>QYLWGLQSTTTGTTLNAGTATTNFTKLRPTNFSNFKKNWLPGPSIKQQGFSKTANQNyempa<br>tgsdsliiyethstldgrwsaltpgppfatagpadskfsnsqlifagpkqngntatvpgtli<br>ftseeelaatnatdtdvwgnlpsgdhsqsnlptvdrptmlgavpgmvwqnrdiyyqgpiwak<br>iphtdghfhpspliggfglkhpppqifikntpvpanpattfistpvnsfitqystgqvsvhi<br>dweiqkerskrwnpevqftsdygqhssllwapdaagkyteptaigtrylthhl<br><br>Aav4_80 (SEQ ID NO: 20)<br>MAADGYLPDWLEDNLSEGVREWWALQPGAPKPKANQQHQDNARGLVLPGYKYLGPGNGLDKG<br>EPVNAADAAALEHDKAYDQQLKAGDNPYLKYNHADAEFQQRLQGDTSFGGNLGRAVFQAKKR<br>VLEPLGLVEQAGETAPGKKRPLIESPQQPDSSTGIGKKGKQPAKKKLVFEDETGAGDGPPEG<br>STSGAMSDDSEMRAAAGGAAVEGGQGADGVGNASGDWHCDSTWSEGHVTTTSTRTWVLPTYN<br>NHLYKRLGESLQSNTYNGFSTPWGYFDFNRFHCHFSPRDWQRLINNNWGMRPKAMRVKIFNI<br>QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br>QYLWGLQSTTTGTTLNAGTATTNFTKLRPTNFSNFKKNWLPGPSIKQQGFSKTANQNdipat<br>gsdslikyethstldgrwsaltpgppmatagpadskfsnsqlifagpkqngntatvpgtlif<br>tseeelaatnatdtdmwgnlpggdqsnsnlptvdrltalgavpgmvwqnrdiyyqgpiwaki<br>phtdghfhpspliggfglkhpppqifikntpvpanpattfsstpvnsfitqystgqvsvqid<br>weiqkerskrwnpevqftsnygqqnsllwapdaagkytepraigtrylthhl |

-continued

| SEQUENCES |
|---|

Aav4_90 (SEQ ID NO: 21)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID
QYLWGLQSTTTGTTLNAGTATTNFTKLRPTNFSNFKKNWLPGPSIKQQGFSKTANQNyiipa
tdsdslityethstldgrwsaltpgppvatagpadskfsnsqlifagpkqngntatvpgtli
ftseeelaatnatdtdmwgnlpfnddsssnlptvdrstflgavpgmvwqnrdiyyqgpiwak
iphtdghfhpspliggfglkhpppqifikntpvpanpattfsstpvnsfitqystgqvsvqi
dweiqkerskrwnpevqftsnygqqnsllwapdaagkytepraigtrylthhl AAV11 capsid protein sequence (GenBank Accession No. AAT46339, SEQ ID NO: 22)
MAADGYLPDWLEDNLSEGIREWWDLKPGAPKPKANQQKQDDGRGLVLPGYKYLGPFNGLDKG
EPVNAADAAALEHDKAYDQQLKAGDNPYLRYNHADAEFQERLQEDTSFGGNLGRAVFQAKKR
VLEPLGLVEEGAKTAPGKKRPLESPQEPDSSSGIGKKGKQPARKRLNFEEDTGAGDGPPEGS
DTSAMSSDIEMRAAPGGNAVDAGQGSDGVGNASGDWHCDSTWSEGKVTTTSTRTWVLPTYNN
HLYLRLGTTSSSNTYNGFSTPWGYFDFNRFHCHFSPRDWQRLINNNWGLRPKAMRVKIFNIQ
VKEVTTSNGETTVANNLTSTVQIFAGSSYELPYVMDAGQEGSLPPFPNDVFMVPQYGYCGIV
TGENQNQTDRNAFYCLEYFPSQMLRTGNNFEMAYNFEKVPFHSMYAHSQSLDRLMNPLLDQY
LWHLQSTTSGETLNQGNAATTFGKIRSGDFAFYRKNWLPGPCVKQQRFSKTASQNYKIPASG
GNALLKYDTHYTLNNRWSNIAPGPPMATAGPSDGDFSNAQLIFPGPSVTGNTTTSANNLLFT
SEEEIAATNPRDTDMFGQIADNNQNATTAPITGNVTAMGVLPGMVWQNRDIYYQGPIWAKIP
HADGHFHPSPLIGGFGLKHPPPQIFIKNTPVPANPATTFTAARVDSFITQYSTGQVAVQIEW
EIEKERSKRWNPEVQFTSNYGNQSSMLWAPDTTGKYTEPRVIGSRYLTNHL AAV12 capsid preotein sequence (GenBank Accession No. ABI16639, SEQ ID NO: 23)
MAADGYLPDWLEDNLSEGIREWWALKPGAPQPKANQQHQDNGRGLVLPGYKYLGPFNGLDKG
EPVNEADAAALEHDKAYDKQLEQGDNPYLKYNHADAEFQQRLATDTSFGGNLGRAVFQAKKR
ILEPLGLVEEGVKTAPGKKRPLEKTPNRPTNPDSGKAPAKKKQKDGEPADSARRTLDFEDSG
AGDGPPEGSSSGEMSHDAEMRAAPGGNAVEAGQGADGVGNASGDWHCDSTWSEGRVTTTSTR
TWVLPTYNNHLYLRIGTTANSNTYNGFSTPWGYFDFNRFHCHFSPRDWQRLINNNWGLRPKS
MRVKIFNIQVKEVTTSNGETTVANNLTSTVQIFAGSTYELPYVMDAGQEGSFPPFPNDVFMV
PQYGYCGVVTGKNQNQTDRNAFYCLEYFPSQMLRTGNNFEVSYQFEKVPFHSMYAHSQSLDR
MMNPLLDQYLWHLQSTTTGNSLNQGTATTTYGKITTGDFAYYRKNWLPGACIKQQKFSKNAN
QNYKIPASGGDALLKYDTHTTLNGRWSNMAPGPPMATAGAGDSDFSNSQLIFAGPNPSGNTT
TSSNNLLFTSEEEIATTNPRDTDMFGQIADNNQNATTAPHIANLDAMGIVPGMVWQNRDIYY
QGPIWAKVPHTDGHFHPSPLMGGFGLKHPPPQIFIKNTPVPANPNTTFSAARINSFLTQYST
GQVAVQIDWEIQKEHSKRWNPEVQFTSNYGTQNSMLWAPDNAGNYHELRAIGSRFLTHHL Bovine AAV capsid protein (GenBank Accession No. AAR26465, SEQ ID NO: 24)
MSFVDHPPDWLESIGDGFREFLGLEAGPPKPKANQQKQDNARGLVLPGYKYLGPGNGLDKGD
PVNFADEVAREHDLSYQKQLEAGDNPYLKYNHADAEFQEKLASDTSFGGNLGKAVFQAKKRI
LEPLGLVETPDKTAPAAKKRPLEQSPQEPDSSSGVGKKGKQPARKRLNFDDEPGAGDGPPPE
GPSSGAMSTETEMRAAAGGNGGDAGQGAEGVGNASGDWHCDSTWSESHVTTTSTRTWVLPTY
NNHLYLRLGSSNASDTFNGFSTPWGYFDFNRFHCHFSPRDWQRLINNNWGLRPKSMQVRIFN
IQVKEVTTSNGETTVSNNLTSTVQIFADSTYELPYVMDAGQEGSLPPFPNDVFMVPQYGYCG
LVTGGSSQNQTDRNAFYCLEYFPSQMLRTGNNFEMVYKFENVPFHSMYAHSQSLDRLMNPLL
DQYLWELQSTTSGGTLNQGNSATNFAKLTKTNFSGYRKNWLPGPMMKQQRFSKTASQNYKIP
QGRNNSLLHYETRTTLDGRWSNFAPGTAMATAANDATDFSQAQLIFAGPNITGNTTTDANNL
MFTSEDELRATNPRDTDLFGHLATNQQNATTVPTVDDVDGVGVYPGMVWQDRDIYYQGPIWA
KIPHTDGHFHPSPLIGGFGLKSPPPQIFIKNTPVPANPATTFSPARINSFITQYSTGQVAVK
IEWEIQKERSKRWNPEVQFTSNYGAQDSLLWAPDNAGAYKEPRAIGSRYLTNHL AAVrh32 capsid protein (GenBank Accession No. AY243003, SEQ ID NO: 25)
MAADGYLPDWLEDNLSEGIREWWDLKPGAPKPKANQQKQDDGRGLVLPGYKYLGPFNGLDKG
EPVNAADAAALEHDKAYDQQLKAGDNPYLRYNHADAEFQERLQEDTSFGGNLGRAVFQAKKR
VLEPLGLVEEGAKTAPGKKRPLESPQEPDSSSGIGKKGKQPAKKRLNFEEDTGAGDGPPEGS
DTSAMSSDIEMRAAPGGNAVDAGQGSDGVGNASGDWHCDSTWSEGKVTTTSTRTWVLPTYNN
HLYLRLGTTSNSNTYNGFSTPWGYFDFNRFHCHFSPRDWQRLINNNWGLRPKAMRVKIFNIQ
VKEVTTSNGETTVANNLTSTVQIFADSSYELPYVMDAGQEGSLPPFPNDVFMVPQYGYCGIV
TGENQNQTDRNAFYCLEYFPSQMLRTGNNFEMAYNFGKVPFHSMYAYSQSPDRLMNPLLDQY
LWHLQSTTSGETLNQGNAATTFGKIRSGDFAFYRKNWLPGPCVKQQRLSKTASQNYKIPASG
GNALLKYDTHYTLNNRWSNIAPGPPMATAGPSDGDFSNAQLIFPGPSVTGNTTTSANNLLFT
SEEEIAATNPRDTDMFGQIADNNQNATTAPITGNVTAMGVLPGMVWQNRDIYYQGPIWAKIP
HADGHFHPSPLIGGFGLKHPPPQIFIKNTPVPANPATTFTAARVDSFITQYSTGQVAVQIEW
EIEKERSKRWNPEVQFTSNYGNQSSMLWAPDTTGKYTEPRVIGSRYLTNHL AAVrh33 capsid protein (GenBank Accession No. AY243002, SEQ ID NO: 26)
MAADGYLPDWLEDNLSEGIREWWDLKPGAPKLKANQQKQDDGRGLVLPGYKYLGPFHGLDKG
EGVNAADAAALEHDKAYDQQLKAGDNPYLRYNHADAEFQERLQEDTSFGGNLGRAVFQAKKR
VLEPLGLVEEGAKTAPGKKRPLESPQEPDSSSGIGKKGKQPAKKRLNFEEDTGAGDGPPEGS
DTSAMSSDIEMRAAPGGNAVDAGQGSDGVGNASGDWHCDSTWSEGKVTTTSTRTWVLPTYNN
HLYLRLGTTSNSNTYNGFSTPWGYFDFNRFHCHFSPRDWQRLINNNWGLRPKAMRVKIFNIQ

| SEQUENCES |
|---|
| VKEVTTSNGETTVANNLTSTVQIFADSSYELPYVMDAGQEGSLPPFPNDVFMVPQYGYCGIV<br>TGENQNQTDRNAFYCLEYFPSQMLRTGNNFEMAYNFEKVPFHSMYAHSQSLDRLMNPLLDQY<br>LWHLQSTTSGETLNQGNAATTFGKIRSGDFAFYRKNWLPGPCVKQQRFSKTASQNYKIPASG<br>GNALLKYDTHYTLNNRWSNIAPGPPMATAGPSDGDFSNAQLIFPGPSVTGNTTTSANNLLFT<br>SEGEIAATNPRDTDMFGQIADNNQNATTAPITGNVTAMGVLPGMVWQNRDIYYQGPIWAKIP<br>HADGHFHPSPLIGGFGLKHPPPQIFIKNTPVPANPATTFTAARVDSFITQYSTGQVAVQIEW<br>EIEKERSKRRNPEVQFTSNYGNQSSMLWAPDTTGKYTEPRVIGSRYLTNHL<br><br>AAVrh34 capsid protein (GenBank Accession No. AY243001, SEQ ID NO: 27)<br>MAADGYLPDWLEDNLSEGIREWWDLKPGAPKPKANQQKQDDGRGLVLPGYEYLGPFNGLDKG<br>EPVNAADAAALEHDKAYDQQLKAGDNPYLRYNHADAEFQERLQEDTSFGGNLGRAVFQAKKR<br>VLEPLGLVEEGAKTAPGKKRPLESPQEPDSSSGIGKKGKQPAKKRLNFEEDTGAGDGPPEGS<br>DTSAMSSDIEMRAAPGGNAVDAGQGSDGVGNASGDWHCDSTWSEGKVTTTSTRTWVLPTYNN<br>HLYLRLGTTSNSNTYNGFSTPWGYFDFNRFHCHFSPRDWQRLINNNWGLRPKAMRVKIFNIQ<br>VKEVTTSNGETTVANNLTSTVQIFADSSYELPYVMDAGQEGSLPPFPNDVFMVPQYGYCGIV<br>TGENQNQTDRNAFYCLEYFPSQMLRTGNNFETAYNFEKVPFHSMYAHSQSLDGLMNPLLDQY<br>LWHLQSTTSGETLNQGNAATTFGKIRSGDFAFYRKNWLPGPCVKQQRFSKTASQNYKIPASG<br>GNALLKYDTHYTLNNRWSNIAPGPPMATAGPSDGDFSNAQLIFPGPSVTGNTTTSANNLLFT<br>SEEEIAATNPRDTDMFGQIADNNQNATTAPITGNVTAMGVLPGMVWQNRDIYYQGPIWAKIP<br>HADGHFHPSPLIGGFGLKHPPPQIFIKNTPVPAYPATTFTAARVDSFITQYSTGQVAVQIEW<br>EIEKERSKRWNPEVQFTSNCGNQSSMLWAPDTTGKYTEPRVIGSRYLTNHL<br><br>AAV4.18 (SEQ ID NO: 28)<br>MAADGYLPDWLEDNLSEGVREWWALQPGAPKPKANQQHQDNARGLVLPGYKYLGPGNGLDKG<br>EPVNAADAAALEHDKAYDQQLKAGDNPYLKYNHADAEFQQRLQGDTSFGGNLGRAVFQAKKR<br>VLEPLGLVEQAGETAPGKKRPLIESPQQPDSSTGIGKKGKQPAKKKLVFEDETGAGDGPPEG<br>STSGAMSDDSEMRAAAGGAAVEGGQGADGVGNASGDWHCDSTWSEGHVTTTSTRTWVLPTYN<br>NHLYKRLGESLQSNTYNGFSTPWGYFDFNRFHCHFSPRDWQRLINNNWGMRPKAMRVKIFNI<br>QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br><br>QYLWGLQSTTTGTTLNAGTATTNFTKLRPTNFSNFKKNWLPGPSIKQQGFSKTANQNYXIPA<br><br>TGSDSLIXYETHSTLDGRWSALTPGPPMATAGPADSKFSNSQLIFAGPKQNGNTATVPGTLI<br><br>FTSEEELAATNATDTDMWGNLPGGDQSXSNLPTVDRLTALGAVPGMVWQNRDIYYQGPIWAK<br><br>IPHTDGHFHPSPLIGGFGLKHPPPQIFIKNTPVPANPATTFSSTPVNSFITQYSTGQVSVQI<br>DWEIQKERSKRWNPEVQFTSNYGQQNSLLWAPDAAGKYTEPRAIGTRYTHHL<br><br>AAV4.18-6a (SEQ ID NO: 29)<br>MAADGYLPDWLEDNLSEGVREWWALQPGAPKPKANQQHQDNARGLVLPGYKYLGPGNGLDKG<br>EPVNAADAAALEHDKAYDQQLKAGDNPYLKYNHADAEFQQRLQGDTSFGGNLGRAVFQAKKR<br>VLEPLGLVEQAGETAPGKKRPLIESPQQPDSSTGIGKKGKQPAKKKLVFEDETGAGDGPPEG<br>STSGAMSDDSEMRAAAGGAAVEGGQGADGVGNASGDWHCDSTWSEGHVTTTSTRTWVLPTYN<br>NHLYKRLGESLQSNTYNGFSTPWGYFDFNRFHCHFSPRDWQRLINNNWGMRPKAMRVKIFNI<br>QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br><br>QYLWGLQSTTTGTTLNAGTATTNFTKLRPTNFSNFKKNWLPGPSIKQQGFSKTANQNYXIPA<br><br>TGSDSLIXYETHSTLDGRWSALTPGPPMATAGPADSKFSNSQLIFAGPKQNGNTATVPGTLI<br><br>FTSEEELAATNATDTDMWGNLPGGDQSXSNLPVVRGLRALGAVPGMVWQNRDIYYQGPIWAK<br><br>IPHTDGHFHPSPLIGGFGLKHPPPQIFIKNTPVPANPATTFSSTPVNSFITQYSTGQVSVQI<br>DWEIQKERSKRWNPEVQFTSNYGQQNSLLWAPDAAGKYTEPRAIGTRYTHHL<br><br>AAV4.18-6b (SEQ ID NO: 30)<br>MAADGYLPDWLEDNLSEGVREWWALQPGAPKPKANQQHQDNARGLVLPGYKYLGPGNGLDKG<br>EPVNAADAAALEHDKAYDQQLKAGDNPYLKYNHADAEFQQRLQGDTSFGGNLGRAVFQAKKR<br>VLEPLGLVEQAGETAPGKKRPLIESPQQPDSSTGIGKKGKQPAKKKLVFEDETGAGDGPPEG<br>STSGAMSDDSEMRAAAGGAAVEGGQGADGVGNASGDWHCDSTWSEGHVTTTSTRTWVLPTYN<br>NHLYKRLGESLQSNTYNGFSTPWGYFDFNRFHCHFSPRDWQRLINNNWGMRPKAMRVKIFNI<br>QVKEVTTSNGETTVANNLTSTVQIFADSSYELPYVMDAGQEGSLPPFPNDVFMVPQYGYCGL<br>VTGNTSQQQTDRNAFYCLEYFPSQMLRTGNNFEITYSFEKVPFHSMYAHSQSLDRLMNPLID<br><br>QYLWGLQSTTTGTTLNAGTATTNFTKLRPTNFSNFKKNWLPGPSIKQQGFSKTANQNYXIPA<br><br>TGSDSLIXYETHSTLDGRWSALTPGPPMATAGPADSKFSNSQLIFAGPKQNGNTATVPGTLI |

SEQUENCES

FTSEEEELAATNATDTMWGNLPGGDQS*SNLPVVNRLS**ALGAVPGMVWQNRDIYYQGPIWAK

IPHTDGHFHPSPLIGGFGLKHPPPQIFIKNTPVPANPATTFSSTPVNSFITQYSTGQVSVQI
DWEIQKERSKRWNPEVQFTSNYGQQNSLLWAPDAAGKYTEPRAIGTRYTHHL

AAV4.18-6c (SEQ ID NO: 31)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID

QYLWGLQSTTTGTTLNAGTATTNFTKLRPTNFSNFKKNWLPGPSIKQQGFSKTANQNY*IPA

TGSDSLI*YETHSTLDGRWSALTPGPPMATAGPADSKFSNSQLIFAGPKQNGNTATVPGTLI

FTSEEEELAATNATDTMWGNLPGGDQS*SNLPPVMGLGGALAVPGMVWQNRDIYYQGPIWAK

IPHTDGHFHPSPLIGGFGLKHPPPQIFIKNTPVPANPATTFSSTPVNSFITQYSTGQVSVQI
DWEIQKERSKRWNPEVQFTSNYGQQNSLLWAPDAAGKYTEPRAIGTRYTHHL

AAV4.18-5a (SEQ ID NO: 32)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID

QYLWGLQSTTTGTTLNAGTATTNFTKLRPTNFSNFKKNWLPGPSIKQQGFSKTANQNY*IPA

TGSDSLI*YETHSTLDGRWSALTPGPPMATAGPADSKFSNSQLIFAGPKQNGNTATVPGTLI

FTSEEEELAATNATDTMWGNLPGGDQSRVDRLPTVDRLTALGAVPGMVWQNRDIYYQGPIWA
KIPHTDGHFHPSPLIGGFGLKHPPPQIFIKNTPVPANPATTFSSTPVNSFITQYSTGQVSVQ
IDWEIQKERSKRWNPEVQFTSNYGQQNSLLWAPDAAGKYTEPRAIGTRYLTHHL

AAV4.18-5b (SEQ ID NO: 33)
MAADGYLPDWLEDNLSEGVREWWALQPGAPKPKANQQHQDNARGLVLPGYKYLGPGNGLDKG
EPVNAADAAALEHDKAYDQQLKAGDNPYLKYNHADAEFQQRLQGDTSFGGNLGRAVFQAKKR
VLEPLGLVEQAGETAPGKKRPLIESPQQPDSSTGIGKKGKQPAKKKLVFEDETGAGDGPPEG
STSGAMSDDSEMRAAAGGAAVEGGQGADGVGNASGDWHCDSTWSEGHVTTTSTRTWVLPTYN
NHLYKRLGESLQSNTYNGFSTPWGYFDFNRFHCHFSPRDWQRLINNNWGMRPKAMRVKIFNI
QVKEVTTSNGETTVANNLTSTVQIFADSSYELPYVMDAGQEGSLPPFPNDVFMVPQYGYCGL
VTGNTSQQQTDRNAFYCLEYFPSQMLRTGNNFEITYSFEKVPFHSMYAHSQSLDRLMNPLID

QYLWGLQSTTTGTTLNAGTATTNFTKLRPTNFSNFKKNWLPGPSIKQQGFSKTANQNY*IPA

TGSDSLI*YETHSTLDGRWSALTPGPPMATAGPADSKFSNSQLIFAGPKQNGNTATVPGTLI

FTSEEEELAATNATDTMWGNLPGGDQSRALRLPTVDRLTALGAVPGMVWQNRDIYYQGPIWA
KIPHTDGHFHPSPLIGGFGLKHPPPQIFIKNTPVPANPATTFSSTPVNSFITQYSTGQVSVQ
IDWEIQKERSKRWNPEVQFTSNYGQQNSLLWAPDAAGKYTEPRAIGTRYLTHHL

TABLE 5

| Engineered AAV Strain | Amino Acid Changes | SEZ | CP | RMS | CMS | OB | CT | HC | Tropism/ Efficiency relative to AAV4 |
| --- | --- | --- | --- | --- | --- | --- | --- | --- | --- |
| AAV4.18 | K492E, K503E, N585S | ++ | ++ | ++ | + | ++ | ++ | + | 1st generation - Expanded/Similar |

TABLE 5-continued

| Engineered AAV Strain | Amino Acid Changes | SEZ | CP | RMS | CMS | OB | CT | HC | Tropism/ Efficiency relative to AAV4 |
|---|---|---|---|---|---|---|---|---|---|
| AAV4.18-6a | T590V, D592R, R593G, T595R* | + | ++ | + | − | − | − | + | 2$^{nd}$ generation - Expanded/Similar |
| AAV4.18-6b | T590V, D592N, T595S* | +++ | +++ | ++ | ++ | + | ++ | + | 2$^{nd}$ generation - Expanded/High |
| AAV4.18-6c | T590P, D592M, R593G, T595G* | ++ | ++ | +++ | ++ | +++ | +++ | +++ | 2$^{nd}$ generation - Expanded/High |
| AAV4.18-5a | N585R, S586V, N587D, L588R* | ++ | ++ | ++ | ++ | + | − | + | 2$^{nd}$ generation - Expanded/Similar |
| AAV4.18-5b | N585R, S586A, N587L, L588R* | ++ | ++ | ++ | + | ++ | − | + | 2$^{nd}$ generation - Expanded/Similar |

*Amino acid changes in addition to those listed for AAV4.18;
SEZ—Sub Ependymal Zone;
CP—Choroid Plexus;
R/CMS—Rostral/Caudal Migration Stream;
OB—Olfactory Bulb;
CT—Cortex;
HC—Hippocampus (+), (++) and (+++) represent Low, Moderate and High number of GFP+ cells, respectively (−) represents No GFP+ cells

That which is claimed is:

1. An adeno-associated virus (AAV) serotype 4 (AAV4) capsid protein, wherein the AAV4 capsid protein comprises (a) a K493E substitution, (b) a K504E substitution; and/or (c) a N586S or a N586R substitution, and further comprises a modification at one or more of amino acid residues M524, G581, G582, Q584, 5587, N588, L589, T591, D593, R594, L595, T596 and/or A597 in any combination, wherein the numbering of the residues is based on the amino acid sequence of SEQ ID NO:2.

2. The AAV4 capsid protein of claim 1, comprising the amino acid sequence of SEQ ID NO:29.

3. The AAV4 capsid protein of claim 1, comprising the amino acid sequence of SEQ ID NO:30.

4. The AAV4 capsid protein of claim 1, comprising the amino acid sequence of SEQ ID NO:31.

5. The AAV4 capsid protein of claim 1, comprising the amino acid sequence of SEQ ID NO:32.

6. The AAV4 capsid protein of claim 1, comprising the amino acid sequence of SEQ ID NO:33.

7. An AAV capsid comprising the AAV4 capsid protein of claim 1.

8. A virus vector comprising: the AAV capsid of claim 7; and a nucleic acid comprising at least one terminal repeat sequence, wherein the nucleic acid is encapsidated by the AAV capsid.

9. A composition comprising the virus vector of claim 8 in a pharmaceutically acceptable carrier.

10. A method of introducing a nucleic acid molecule into a cell, comprising contacting the cell with the virus vector of claim 8.

11. A method of introducing a nucleic acid molecule into a cell, comprising contacting the cell with the virus vector of claim 8.

12. A method of delivering a nucleic acid molecule to a subject, comprising administering to the subject the virus vector of claim 8.

13. The method of claim 11, wherein the virus vector or composition is administered to the central nervous system of the subject.

14. A method of selectively transducing a cell having polysialic acid on the surface, comprising contacting the cell with the virus vector of claim 8.

15. A method of selectively delivering a nucleic acid molecule of interest to a central nervous system progenitor cell and/or neuroblast, comprising contacting the progenitor cell and/or neuroblast with the virus vector of claim 8, wherein the virus vector comprises the nucleic acid molecule of interest.

16. The method of claim 15, wherein the nucleic acid molecule of interest encodes a therapeutic protein or therapeutic RNA.

17. The method of claim 10, wherein the cell and/or neuroblast is in a subject.

18. The method of claim 17, wherein the subject is a human subject.

19. A method of treating a neurological disorder or defect in a subject, comprising administering to the subject the virus vector of claim 8, wherein the virus vector comprises a nucleic acid molecule that encodes a therapeutic protein or therapeutic RNA effective in treating the neurological disorder or defect.

20. The method of claim 12, wherein the virus vector or composition is administered via an intracerebroventrical, intracisternal, intraparenchymal, intracranial and/or intrathecal route.

21. A method of selectively transducing a cell having polysialic acid on the surface, comprising contacting the cell with the virus vector of claim 8.

22. A method of selectively delivering a nucleic acid molecule of interest to a central nervous system progenitor cell and/or neuroblast, comprising contacting the progenitor cell and/or neuroblast with the virus vector of claim 8, wherein the virus vector comprises the nucleic acid molecule of interest.

23. The method of claim 22, wherein the nucleic acid molecule of interest encodes a therapeutic protein or therapeutic RNA.

24. The method of claim 21, wherein the cell and/or neuroblast is in a subject.

25. A method of treating a neurological disorder or defect in a subject, comprising administering to the subject the virus vector of claim 8, wherein the virus vector comprises a nucleic acid molecule that encodes a therapeutic protein or therapeutic RNA effective in treating the neurological disorder or defect.

26. The method of claim 24, wherein the virus vector or composition is administered via an intracerebroventrical, intracisternal, intraparenchymal, intracranial and/or intrathecal route.

27. The method of claim 24, wherein the subject is a human subject.

28. The AAV4 capsid protein of claim 1, wherein the AAV4 capsid protein comprises one or more additional amino acid insertions, substitutions and/or deletions as compared with the amino acid sequence of SEQ ID NO:2.

29. The AAV4 capsid protein of claim 28, wherein the AAV4 capsid protein comprises less than 70 additional amino acid insertions, substitutions and/or deletions as compared with the amino acid sequence of SEQ ID NO:2.

30. The AAV4 capsid protein of claim 28, wherein the AAV4 capsid protein comprises less than 50 additional amino acid insertions, substitutions and/or deletions as compared with the amino acid sequence of SEQ ID NO:2.

31. The AAV4 capsid protein of claim 28, wherein the AAV4 capsid protein comprises less than 20 additional amino acid insertions, substitutions and/or deletions as compared with the amino acid sequence of SEQ ID NO:2.

32. The AAV4 capsid protein of claim 1, wherein the AAV4 capsid protein comprises one or more of the following substitutions: S587V or S587A; N588D or N588L; L589R; T591V or T591P; D593R or D593N or D593M; R594G; and/or T596R, T596G, or T596S.

33. The AAV4 capsid protein of claim 32, wherein the AAV4 capsid protein comprises one of the following substitutions: S587V or S587A.

34. The AAV4 capsid protein of claim 32, wherein the AAV4 capsid protein comprises one of the following substitutions: N588D or N588L.

35. The AAV4 capsid protein of claim 32, wherein the AAV4 capsid protein comprises the following substitution: L589R.

36. The AAV4 capsid protein of claim 32, wherein the AAV4 capsid protein comprises one of the following substitutions: T591V or T591P.

37. The AAV4 capsid protein of claim 32, wherein the AAV4 capsid protein comprises one of the following substitution: D593R or D593N or D593M.

38. The AAV4 capsid protein of claim 32, wherein the AAV4 capsid protein comprises the following substitution: R594G.

39. The AAV4 capsid protein of claim 32, wherein the AAV4 capsid protein comprises one of the following substitution: T596R, T596G, or T596S.

* * * * *

UNITED STATES PATENT AND TRADEMARK OFFICE
CERTIFICATE OF CORRECTION

PATENT NO. : 10,907,176 B2
APPLICATION NO. : 15/543536
DATED : February 2, 2021
INVENTOR(S) : Asokan et al.

Page 1 of 1

It is certified that error appears in the above-identified patent and that said Letters Patent is hereby corrected as shown below:

In the Specification

Column 14, Line 8: Please correct "aav440" to read -- aav4_40 --

In the Claims

Column 207, Line 7, Claim 1: Please correct "5587" to read -- S587 --

Signed and Sealed this
First Day of June, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 57

<210> SEQ ID NO 1
<211> LENGTH: 734
<212> TYPE: PRT
<213> ORGANISM: adeno-associated virus 4

<400> SEQUENCE: 1

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175
```

Gly Ala Gly Asp Gly Pro Pro Glu Gly Ser Thr Ser Gly Ala Met Ser
            180                 185                 190

Asp Asp Ser Glu Met Arg Ala Ala Gly Gly Ala Ala Val Glu Gly
        195                 200                 205

Gly Gln Gly Ala Asp Gly Val Gly Asn Ala Ser Gly Asp Trp His Cys
        210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
        290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg

```
                    595                 600                 605

Asp Ile Tyr Tyr Gln Gly Pro Ile Trp Ala Lys Ile Pro His Thr Asp
    610                 615                 620

Gly His Phe His Pro Ser Pro Leu Ile Gly Phe Gly Leu Lys His
625                 630                 635                 640

Pro Pro Pro Gln Ile Phe Ile Lys Asn Thr Pro Val Pro Ala Asn Pro
                    645                 650                 655

Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
                675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                    725                 730

<210> SEQ ID NO 2
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 2

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220
```

-continued

```
Cys Asp Ser Thr Trp Ser Glu Gly His Val Thr Thr Ser Thr Arg
225                 230                 235                 240

Thr Trp Val Leu Pro Thr Tyr Asn Asn His Leu Tyr Lys Arg Leu Gly
            245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
            355                 360                 365

Tyr Cys Gly Leu Val Thr Gly Asn Thr Ser Gln Gln Gln Thr Asp Arg
370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
            435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Lys Ile Pro Ala
                485                 490                 495

Thr Gly Ser Asp Ser Leu Ile Lys Tyr Glu Thr His Ser Thr Leu Asp
            500                 505                 510

Gly Arg Trp Ser Ala Leu Thr Pro Gly Pro Met Ala Thr Ala Gly
            515                 520                 525

Pro Ala Asp Ser Lys Phe Ser Asn Ser Gln Leu Ile Phe Ala Gly Pro
            530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Gly Gly Asp Gln Ser Asn Ser Asn Leu Pro Thr Val
            580                 585                 590

Asp Arg Leu Thr Ala Leu Gly Ala Val Pro Gly Met Val Trp Gln Asn
            595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
```

```
                      645                 650                 655

Pro Ala Thr Thr Phe Ser Ser Thr Pro Val Asn Ser Phe Ile Thr Gln
                660                 665                 670

Tyr Ser Thr Gly Gln Val Ser Val Gln Ile Asp Trp Glu Ile Gln Lys
            675                 680                 685

Glu Arg Ser Lys Arg Trp Asn Pro Glu Val Gln Phe Thr Ser Asn Tyr
690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 3
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 3

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270
```

-continued

```
Tyr Phe Asp Phe Asn Arg Phe His Cys His Phe Ser Pro Arg Asp Trp
            275                 280                 285

Gln Arg Leu Ile Asn Asn Asn Trp Gly Met Arg Pro Lys Ala Met Arg
290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
        435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Leu Ile Pro Ala
                485                 490                 495

Thr Gly Ser Asp Ser Leu Ile Arg Tyr Glu Thr His Ser Thr Leu Asp
            500                 505                 510

Gly Arg Trp Ser Ala Leu Thr Pro Gly Pro Met Ala Thr Ala Gly
        515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Phe Arg Asp Leu Ser Ser Asn Leu Pro Thr Val
            580                 585                 590

Asp Arg Ser Thr Pro Leu Gly Ala Val Pro Gly Met Val Trp Gln Asn
        595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
        675                 680                 685

Glu Arg Ser Lys Arg Trp Asn Pro Glu Val Gln Phe Thr Ser Asn Tyr
```

```
                690               695                 700
Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735
```

<210> SEQ ID NO 4
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 4

```
Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
290                 295                 300

Val Lys Ile Phe Asn Ile Gln Val Lys Glu Val Thr Thr Ser Asn Gly
305                 310                 315                 320
```

```
Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
    370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
            405                 410                 415

Ser Met Tyr Ala His Ser Gln Ser Leu Asp Arg Leu Met Asn Pro Leu
        420                 425                 430

Ile Asp Gln Tyr Leu Trp Gly Leu Gln Ser Thr Thr Thr Gly Thr Thr
    435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Tyr Ile Pro Ala
            485                 490                 495

Thr Gly Ser Asp Ser Leu Ile Leu Tyr Glu Thr His Ser Thr Leu Asp
        500                 505                 510

Gly Arg Trp Ser Ala Leu Thr Pro Gly Pro Pro Met Ala Thr Ala Gly
    515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
            565                 570                 575

Gly Asn Leu Pro Gly Gly Asp Gln Ser Asn Ser Asn Leu Pro Thr Val
        580                 585                 590

Asp Arg Leu Thr Ala Leu Gly Ala Val Pro Gly Met Val Trp Gln Asn
    595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
            645                 650                 655

Pro Ala Thr Thr Phe Ser Ser Thr Pro Val Asn Ser Phe Ile Thr Gln
        660                 665                 670

Tyr Ser Thr Gly Gln Val Ser Val Gln Ile Asp Trp Glu Ile Gln Lys
    675                 680                 685

Glu Arg Ser Lys Arg Trp Asn Pro Glu Val Gln Phe Thr Ser Asn Tyr
690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
            725                 730                 735
```

```
<210> SEQ ID NO 5
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 5
```

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
    290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
            405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
            435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Gly Ile Pro Ala
                485                 490                 495

Thr Gly Ser Asp Ser Leu Ile Lys Tyr Glu Thr His Ser Thr Leu Asp
            500                 505                 510

Gly Arg Trp Ser Ala Leu Thr Pro Gly Pro Pro Ile Ala Thr Ala Gly
            515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Leu Tyr Asp Ala Ser Ser Ser Asn Leu Pro Thr Val
            580                 585                 590

Asp Arg Leu Thr Leu Leu Gly Ala Val Pro Gly Met Val Trp Gln Asn
            595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
            675                 680                 685

Glu Arg Ser Lys Arg Trp Asn Pro Glu Val Gln Phe Thr Ser Asn Tyr
690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 6
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 6

```
Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65              70              75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
    130                 135                 140

Pro Leu Ile Glu Ser Pro Gln Pro Asp Ser Ser Thr Gly Ile Gly
145                 150                 155                 160

Lys Lys Gly Lys Gln Pro Ala Lys Lys Lys Leu Val Phe Glu Asp Glu
            165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
            195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
    275                 280                 285

Gln Arg Leu Ile Asn Asn Asn Trp Gly Met Arg Pro Lys Ala Met Arg
    290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
            325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
            355                 360                 365

Tyr Cys Gly Leu Val Thr Gly Asn Thr Ser Gln Gln Thr Asp Arg
370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415
```

```
Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
    435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Thr Ile Pro Ala
                485                 490                 495

Thr Gly Ser Asp Ser Leu Ile Thr Tyr Glu Thr His Ser Thr Leu Asp
            500                 505                 510

Gly Arg Trp Ser Ala Leu Thr Pro Gly Pro Pro Gly Ala Thr Ala Gly
    515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Arg Val Asp Thr Ser Ala Ser Asn Leu Pro Thr Val
            580                 585                 590

Asp Arg Tyr Thr Asn Leu Gly Ala Val Pro Gly Met Val Trp Gln Asn
    595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
    675                 680                 685

Glu Arg Ser Lys Arg Trp Asn Pro Glu Val Gln Phe Thr Ser Asn Tyr
690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 7
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 7

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45
```

```
Gly Tyr Lys Tyr Leu Gly Pro Gly Asn Gly Leu Asp Lys Gly Glu Pro
     50                  55                  60

Val Asn Ala Ala Asp Ala Ala Leu Glu His Asp Lys Ala Tyr Asp
 65              70                  75                  80

Gln Gln Leu Lys Ala Gly Asp Pro Tyr Leu Lys Tyr Asn His Ala
             85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
            130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Gly Gly Ala Ala Val Glu
            195                 200                 205

Gly Gly Gln Gly Ala Asp Gly Val Gly Asn Ala Ser Gly Asp Trp His
            210                 215                 220

Cys Asp Ser Thr Trp Ser Glu Gly His Val Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
            275                 280                 285

Gln Arg Leu Ile Asn Asn Asn Trp Gly Met Arg Pro Lys Ala Met Arg
            290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
            355                 360                 365

Tyr Cys Gly Leu Val Thr Gly Asn Thr Ser Gln Gln Gln Thr Asp Arg
            370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
            435                 440                 445

Leu Asn Ala Gly Thr Ala Thr Thr Asn Phe Thr Lys Leu Arg Pro Thr
450                 455                 460
```

```
Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Ser Ile Pro Ala
            485                 490                 495

Thr Gly Ser Asp Ser Leu Ile Lys Tyr Glu Thr His Ser Thr Leu Asp
                500                 505                 510

Gly Arg Trp Ser Ala Leu Thr Pro Gly Pro Pro Phe Ala Thr Ala Gly
            515                 520                 525

Pro Ala Asp Ser Lys Phe Ser Asn Ser Gln Leu Ile Phe Ala Gly Pro
        530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Asp Tyr Asp Ser Ser Leu Ser Asn Leu Pro Thr Val
                580                 585                 590

Asp Arg Asp Thr Thr Leu Gly Ala Val Pro Gly Met Val Trp Gln Asn
        595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
                660                 665                 670

Tyr Ser Thr Gly Gln Val Ser Val Gln Ile Asp Trp Glu Ile Gln Lys
            675                 680                 685

Glu Arg Ser Lys Arg Trp Asn Pro Glu Val Gln Phe Thr Ser Asn Tyr
690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735
```

<210> SEQ ID NO 8
<211> LENGTH: 735
<212> TYPE: PRT
<213> ORGANISM: Artificial
<220> FEATURE:
<223> OTHER INFORMATION: Recombinant adeno-associated virus 4 capsid protein sequence

<400> SEQUENCE: 8

```
Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95
```

-continued

Asp Ala Glu Phe Gln Gln Arg Leu Gln Gly Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
        130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Gly Gly Ala Ala Val Glu
        195                 200                 205

Gly Gly Gln Gly Ala Asp Gly Val Gly Asn Ala Ser Gly Asp Trp His
210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Trp Gly Met Arg Pro Lys Ala Met Arg
        290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Gly Thr Thr
        435                 440                 445

Leu Asn Ala Gly Thr Ala Thr Thr Asn Phe Thr Lys Leu Arg Pro Thr
        450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Ser Ile Pro Ala
                485                 490                 495

Thr Gly Ser Asp Ser Leu Ile Trp Tyr Glu Thr His Ser Thr Leu Asp
            500                 505                 510

Gly Arg Trp Ser Ala Leu Thr Pro Gly Pro Cys Ala Thr Ala Gly
            515                 520                 525

Pro Ala Asp Ser Lys Phe Ser Asn Ser Gln Leu Ile Phe Ala Gly Pro
    530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Gln Gly Asp Ser Ser Leu Ser Asn Leu Pro Thr Val
            580                 585                 590

Asp Arg Met Thr Val Leu Gly Ala Val Pro Gly Met Val Trp Gln Asn
        595                 600                 605

Arg Asp Ile Tyr Tyr Gln Gly Pro Ile Trp Ala Lys Ile Pro His Thr
    610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
        675                 680                 685

Glu Arg Ser Lys Arg Trp Asn Pro Glu Val Gln Phe Thr Ser Asn Tyr
    690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 9
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 9

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

```
Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
            165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Gly Gly Ala Ala Val Glu
    195                 200                 205

Gly Gly Gln Gly Ala Asp Gly Val Gly Asn Ala Ser Gly Asp Trp His
        210                 215                 220

Cys Asp Ser Thr Trp Ser Glu Gly His Val Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
            355                 360                 365

Tyr Cys Gly Leu Val Thr Gly Asn Thr Ser Gln Gln Gln Thr Asp Arg
        370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Gly Thr Thr
        435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Cys Ile Pro Ala
                485                 490                 495

Thr Gly Ser Asp Ser Leu Ile Arg Tyr Glu Thr His Ser Thr Leu Asp
            500                 505                 510

Gly Arg Trp Ser Ala Leu Thr Pro Gly Pro Pro Leu Ala Thr Ala Gly
        515                 520                 525

Pro Ala Asp Ser Lys Phe Ser Asn Ser Gln Leu Ile Phe Ala Gly Pro
    530                 535                 540

Lys Gln Asn Gly Asn Thr Ala Thr Val Pro Gly Thr Leu Ile Phe Thr
545                 550                 555                 560
```

```
Ser Glu Glu Glu Leu Ala Ala Thr Asn Ala Thr Asp Thr Asp Met Trp
            565                 570                 575

Gly Asn Leu Pro Tyr Lys Asp Ser Ser Arg Ser Asn Leu Pro Thr Val
        580                 585                 590

Asp Arg Glu Thr Ser Leu Gly Ala Val Pro Gly Met Val Trp Gln Asn
    595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
                660                 665                 670

Tyr Ser Thr Gly Gln Val Ser Val Gln Ile Asp Trp Glu Ile Gln Lys
                675                 680                 685

Glu Arg Ser Lys Arg Trp Asn Pro Glu Val Gln Phe Thr Ser Asn Tyr
            690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 10
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 10

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190
```

```
Ser Asp Asp Ser Glu Met Arg Ala Ala Gly Gly Ala Val Glu
        195                 200                 205

Gly Gly Gln Gly Ala Asp Val Gly Asn Ala Ser Gly Asp Trp His
    210                 215                 220

Cys Asp Ser Thr Trp Ser Glu Gly His Val Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
                260                 265                 270

Tyr Phe Asp Phe Asn Arg Phe His Cys His Phe Ser Pro Arg Asp Trp
                275                 280                 285

Gln Arg Leu Ile Asn Asn Asn Trp Gly Met Arg Pro Lys Ala Met Arg
            290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
                340                 345                 350

Ser Leu Pro Pro Phe Pro Asn Asp Val Phe Met Val Pro Gln Tyr Gly
                355                 360                 365

Tyr Cys Gly Leu Val Thr Gly Asn Thr Ser Gln Gln Gln Thr Asp Arg
                370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
                420                 425                 430

Ile Asp Gln Tyr Leu Trp Gly Leu Gln Ser Thr Thr Thr Gly Thr Thr
            435                 440                 445

Leu Asn Ala Gly Thr Ala Thr Thr Asn Phe Thr Lys Leu Arg Pro Thr
    450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Ile Ile Pro Ala
                485                 490                 495

Thr Gly Ser Asp Ser Leu Ile Tyr Tyr Glu Thr His Ser Thr Leu Asp
                500                 505                 510

Gly Arg Trp Ser Ala Leu Thr Pro Gly Pro Pro Arg Ala Thr Ala Gly
            515                 520                 525

Pro Ala Asp Ser Lys Phe Ser Asn Ser Gln Leu Ile Phe Ala Gly Pro
    530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Trp Ile Asp Asn Ser Arg Ser Asn Leu Pro Thr Val
            580                 585                 590

Asp Arg Pro Thr Ser Leu Gly Ala Val Pro Gly Met Val Trp Gln Asn
            595                 600                 605
```

```
Lys Asn Ile Tyr Tyr Gln Gly Pro Ile Trp Ala Lys Ile Pro His Thr
    610                 615                 620
Asp Gly His Phe His Pro Ser Pro Leu Ile Gly Gly Phe Gly Leu Lys
625                 630                 635                 640
His Pro Pro Pro Gln Ile Phe Ile Lys Asn Thr Pro Val Pro Ala Asn
                645                 650                 655
Pro Ala Thr Thr Phe Thr Ser Thr Pro Val Asn Ser Phe Ile Thr Gln
                660                 665                 670
Tyr Ser Thr Gly Gln Val Ser Val Gln Ile Asp Trp Glu Ile Gln Lys
                675                 680                 685
Glu Arg Ser Lys Arg Trp Asn Pro Glu Val Gln Phe Thr Ser Asn Tyr
690                 695                 700
Gly Gln Gln Asn Ser Leu Leu Trp Ala Pro Asp Ala Ala Gly Lys Tyr
705                 710                 715                 720
Thr Glu Pro Arg Ala Ile Gly Thr Arg Tyr Leu Thr His His Leu
                725                 730                 735
```

<210> SEQ ID NO 11
<211> LENGTH: 735
<212> TYPE: PRT
<213> ORGANISM: Artificial
<220> FEATURE:
<223> OTHER INFORMATION: Recombinant adeno-associated virus 4 capsid protein sequence

<400> SEQUENCE: 11

```
Met Ala Ala Asp Gly Tyr Leu Pro Asp Trp Leu Glu Asp Asn Leu Ser
1               5                   10                  15
Glu Gly Val Arg Glu Trp Trp Ala Leu Gln Pro Gly Ala Pro Lys Pro
                20                  25                  30
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Gln Arg Leu Gln Gly Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Gln Ala Gly Glu Thr Ala Pro Gly Lys Lys Arg
        130                 135                 140
Pro Leu Ile Glu Ser Pro Gln Gln Pro Asp Ser Ser Thr Gly Ile Gly
145                 150                 155                 160
Lys Lys Gly Lys Gln Pro Ala Lys Lys Leu Val Phe Glu Asp Glu
                165                 170                 175
Thr Gly Ala Gly Asp Gly Pro Pro Glu Gly Ser Thr Ser Gly Ala Met
                180                 185                 190
Ser Asp Asp Ser Glu Met Arg Ala Ala Ala Gly Gly Ala Ala Val Glu
            195                 200                 205
Gly Gly Gln Gly Ala Asp Gly Val Gly Asn Ala Ser Gly Asp Trp His
        210                 215                 220
Cys Asp Ser Thr Trp Ser Glu Gly His Val Thr Thr Thr Ser Thr Arg
225                 230                 235                 240
```

```
Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
    290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
    370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
        435                 440                 445

Leu Asn Ala Gly Thr Ala Thr Thr Asn Phe Thr Lys Leu Arg Pro Thr
    450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Gly Ile Pro Ala
                485                 490                 495

Thr Gly Ser Asp Ser Leu Ile Ile Tyr Glu Thr His Ser Thr Leu Asp
            500                 505                 510

Gly Arg Trp Ser Ala Leu Thr Pro Gly Pro Pro Arg Ala Thr Ala Gly
        515                 520                 525

Pro Ala Asp Ser Lys Phe Ser Asn Ser Gln Leu Ile Phe Ala Gly Pro
    530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Gly Gly Asp Gln Ser Asn Ser Asn Leu Pro Thr Val
            580                 585                 590

Asp Arg Leu Thr Ala Leu Gly Ala Val Pro Gly Met Val Trp Gln Asn
        595                 600                 605

Arg Asp Ile Tyr Tyr Gln Gly Pro Ile Trp Ala Lys Ile Pro His Thr
    610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655
```

```
Pro Ala Thr Thr Phe Ser Ser Thr Pro Val Asn Ser Phe Ile Thr Gln
              660                 665                 670

Tyr Ser Thr Gly Gln Val Ser Val Gln Ile Asp Trp Glu Ile Gln Lys
        675                 680                 685

Glu Arg Ser Lys Arg Trp Asn Pro Glu Val Gln Phe Thr Ser Asn Tyr
    690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 12
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 12

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285
```

-continued

```
Gln Arg Leu Ile Asn Asn Trp Gly Met Arg Pro Lys Ala Met Arg
    290                 295                 300
Val Lys Ile Phe Asn Ile Gln Val Lys Glu Val Thr Thr Ser Asn Gly
305                 310                 315                 320
Glu Thr Thr Val Ala Asn Asn Leu Thr Ser Thr Val Gln Ile Phe Ala
                325                 330                 335
Asp Ser Ser Tyr Glu Leu Pro Tyr Val Met Asp Ala Gly Gln Glu Gly
                340                 345                 350
Ser Leu Pro Pro Phe Pro Asn Asp Val Phe Met Val Pro Gln Tyr Gly
            355                 360                 365
Tyr Cys Gly Leu Val Thr Gly Asn Thr Ser Gln Gln Gln Thr Asp Arg
    370                 375                 380
Asn Ala Phe Tyr Cys Leu Glu Tyr Phe Pro Ser Gln Met Leu Arg Thr
385                 390                 395                 400
Gly Asn Asn Phe Glu Ile Thr Tyr Ser Phe Glu Lys Val Pro Phe His
                405                 410                 415
Ser Met Tyr Ala His Ser Gln Ser Leu Asp Arg Leu Met Asn Pro Leu
                420                 425                 430
Ile Asp Gln Tyr Leu Trp Gly Leu Gln Ser Thr Thr Thr Gly Thr Thr
            435                 440                 445
Leu Asn Ala Gly Thr Ala Thr Thr Asn Phe Thr Lys Leu Arg Pro Thr
450                 455                 460
Asn Phe Ser Asn Phe Lys Lys Asn Trp Leu Pro Gly Pro Ser Ile Lys
465                 470                 475                 480
Gln Gln Gly Phe Ser Lys Thr Ala Asn Gln Asn Tyr Val Ile Pro Ala
                485                 490                 495
Thr Glu Ser Asp Ser Leu Ile Tyr Tyr Glu Thr His Ser Thr Leu Asp
                500                 505                 510
Gly Arg Trp Ser Ala Leu Thr Pro Gly Pro Pro Tyr Ala Thr Ala Gly
            515                 520                 525
Pro Ala Asp Ser Lys Phe Ser Asn Ser Gln Leu Ile Phe Ala Gly Pro
530                 535                 540
Lys Gln Asn Gly Asn Thr Ala Thr Val Pro Gly Thr Leu Ile Phe Thr
545                 550                 555                 560
Ser Glu Glu Glu Leu Ala Ala Thr Asn Ala Thr Asp Thr Asp Met Trp
                565                 570                 575
Gly Asn Leu Pro Pro Arg Asp Asp Ser Thr Ser Asn Leu Pro Thr Val
            580                 585                 590
Asp Arg Lys Thr Tyr Leu Gly Ala Val Pro Gly Met Val Trp Gln Asn
        595                 600                 605
Arg Asp Ile Tyr Tyr Gln Gly Pro Ile Trp Ala Lys Ile Pro His Thr
    610                 615                 620
Asp Gly His Phe His Pro Ser Pro Leu Ile Gly Gly Phe Gly Leu Lys
625                 630                 635                 640
His Pro Pro Pro Gln Ile Phe Ile Lys Asn Thr Pro Val Pro Ala Asn
                645                 650                 655
Pro Ala Thr Thr Phe Ser Ser Thr Pro Val Asn Ser Phe Ile Thr Gln
                660                 665                 670
Tyr Ser Thr Gly Gln Val Ser Val Gln Ile Asp Trp Glu Ile Gln Lys
            675                 680                 685
Glu Arg Ser Lys Arg Trp Asn Pro Glu Val Gln Phe Thr Ser Asn Tyr
    690                 695                 700
```

```
Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
            725                 730                 735

<210> SEQ ID NO 13
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 13

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
    290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335
```

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
            355                 360                 365

Tyr Cys Gly Leu Val Thr Gly Asn Thr Ser Gln Gln Gln Thr Asp Arg
370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
            435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Tyr Ile Pro Ala
                485                 490                 495

Thr Gly Ser Asp Ser Leu Ile Ile Tyr Glu Thr His Ser Thr Leu Asp
            500                 505                 510

Gly Arg Trp Ser Ala Leu Thr Pro Gly Pro Pro Ile Ala Thr Ala Gly
            515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ser Thr Asp Thr Asp Met Trp
                565                 570                 575

Gly Asn Leu Pro Thr Asp Asp Ser Arg Ser Asn Leu Pro Thr Val
            580                 585                 590

Asp Arg Met Thr Leu Leu Gly Ala Val Pro Gly Met Val Trp Gln Asn
            595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
            675                 680                 685

Glu Arg Ser Lys Arg Trp Asn Pro Glu Val Gln Phe Thr Ser Asn Tyr
690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 14
<211> LENGTH: 735

<212> TYPE: PRT
<213> ORGANISM: Artificial
<220> FEATURE:
<223> OTHER INFORMATION: Recombinant adeno-associated virus 4 capsid protein sequence

<400> SEQUENCE: 14

```
Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Trp Gly Met Arg Pro Lys Ala Met Arg
    290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
    370                 375                 380
```

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
            405                 410                 415

Ser Met Tyr Ala His Ser Gln Ser Leu Asp Arg Leu Met Asn Pro Leu
        420                 425                 430

Ile Asp Gln Tyr Leu Trp Gly Leu Gln Ser Thr Thr Thr Gly Thr Thr
    435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr His Ile Pro Ala
                485                 490                 495

Thr Gly Ser Asp Ser Leu Ile Tyr Tyr Glu Thr His Ser Thr Leu Asp
            500                 505                 510

Gly Arg Trp Ser Ala Leu Thr Pro Gly Pro Pro Ser Ala Thr Ala Gly
        515                 520                 525

Pro Ala Asp Ser Lys Phe Ser Asn Ser Gln Leu Ile Phe Ala Gly Pro
    530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Arg Arg Asp Ser Ser Val Ser Asn Leu Pro Thr Val
            580                 585                 590

Asp Arg Tyr Thr Asp Leu Gly Ala Val Pro Gly Met Val Trp Gln Asn
        595                 600                 605

Arg Asp Ile Tyr Tyr Gln Gly Pro Ile Trp Ala Lys Ile Pro His Thr
    610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
        675                 680                 685

Glu Arg Ser Lys Arg Trp Asn Pro Glu Val Gln Phe Thr Ser Asn Tyr
    690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 15
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 15

Met Ala Ala Asp Gly Tyr Leu Pro Asp Trp Leu Glu Asp Asn Leu Ser

-continued

| 1 | | | | 5 | | | | | 10 | | | | | 15 | |
|---|---|---|---|---|---|---|---|---|---|---|---|---|---|---|---|

Glu Gly Val Arg Glu Trp Trp Ala Leu Gln Pro Gly Ala Pro Lys Pro
                    20                      25                      30

Lys Ala Asn Gln Gln His Gln Asp Asn Ala Arg Gly Leu Val Leu Pro
              35                      40                      45

Gly Tyr Lys Tyr Leu Gly Pro Gly Asn Gly Leu Asp Lys Gly Glu Pro
        50                      55                      60

Val Asn Ala Ala Asp Ala Ala Ala Leu Glu His Asp Lys Ala Tyr Asp
65                      70                      75                      80

Gln Gln Leu Lys Ala Gly Asp Asn Pro Tyr Leu Lys Tyr Asn His Ala
                    85                      90                      95

Asp Ala Glu Phe Gln Gln Arg Leu Gln Gly Asp Thr Ser Phe Gly Gly
              100                     105                     110

Asn Leu Gly Arg Ala Val Phe Gln Ala Lys Lys Arg Val Leu Glu Pro
        115                     120                     125

Leu Gly Leu Val Glu Gln Ala Gly Glu Thr Ala Pro Gly Lys Lys Arg
130                     135                     140

Pro Leu Ile Glu Ser Pro Gln Gln Pro Asp Ser Ser Thr Gly Ile Gly
145                     150                     155                     160

Lys Lys Gly Lys Gln Pro Ala Lys Lys Lys Leu Val Phe Glu Asp Glu
                    165                     170                     175

Thr Gly Ala Gly Asp Gly Pro Pro Glu Gly Ser Thr Ser Gly Ala Met
              180                     185                     190

Ser Asp Asp Ser Glu Met Arg Ala Ala Gly Gly Ala Ala Val Glu
        195                     200                     205

Gly Gly Gln Gly Ala Asp Gly Val Gly Asn Ala Ser Gly Asp Trp His
        210                     215                     220

Cys Asp Ser Thr Trp Ser Glu Gly His Val Thr Thr Ser Thr Arg
225                     230                     235                     240

Thr Trp Val Leu Pro Thr Tyr Asn Asn His Leu Tyr Lys Arg Leu Gly
                    245                     250                     255

Glu Ser Leu Gln Ser Asn Thr Tyr Asn Gly Phe Ser Thr Pro Trp Gly
              260                     265                     270

Tyr Phe Asp Phe Asn Arg Phe His Cys His Phe Ser Pro Arg Asp Trp
        275                     280                     285

Gln Arg Leu Ile Asn Asn Asn Trp Gly Met Arg Pro Lys Ala Met Arg
        290                     295                     300

Val Lys Ile Phe Asn Ile Gln Val Lys Glu Val Thr Thr Ser Asn Gly
305                     310                     315                     320

Glu Thr Thr Val Ala Asn Asn Leu Thr Ser Thr Val Gln Ile Phe Ala
                    325                     330                     335

Asp Ser Ser Tyr Glu Leu Pro Tyr Val Met Asp Ala Gly Gln Glu Gly
              340                     345                     350

Ser Leu Pro Pro Phe Pro Asn Asp Val Phe Met Val Pro Gln Tyr Gly
        355                     360                     365

Tyr Cys Gly Leu Val Thr Gly Asn Thr Ser Gln Gln Gln Thr Asp Arg
        370                     375                     380

Asn Ala Phe Tyr Cys Leu Glu Tyr Phe Pro Ser Gln Met Leu Arg Thr
385                     390                     395                     400

Gly Asn Asn Phe Glu Ile Thr Tyr Ser Phe Glu Lys Val Pro Phe His
                    405                     410                     415

Ser Met Tyr Ala His Ser Gln Ser Leu Asp Arg Leu Met Asn Pro Leu
              420                     425                     430

```
Ile Asp Gln Tyr Leu Trp Gly Leu Gln Ser Thr Thr Thr Gly Thr Thr
            435                 440                 445
Leu Asn Ala Gly Thr Ala Thr Thr Asn Phe Thr Lys Leu Arg Pro Thr
450                 455                 460
Asn Phe Ser Asn Phe Lys Lys Asn Trp Leu Pro Gly Pro Ser Ile Lys
465                 470                 475                 480
Gln Gln Gly Phe Ser Lys Thr Ala Asn Gln Asn Tyr Ser Ile Pro Ala
            485                 490                 495
Thr Gly Ser Asp Ser Leu Ile Ser Tyr Glu Thr His Ser Thr Leu Asp
            500                 505                 510
Gly Arg Trp Ser Ala Leu Thr Pro Gly Pro Pro Arg Ala Thr Ala Gly
            515                 520                 525
Pro Ala Asp Ser Lys Phe Ser Asn Ser Gln Leu Ile Phe Ala Gly Pro
530                 535                 540
Lys Gln Asn Gly Asn Thr Ala Thr Val Pro Gly Thr Leu Ile Phe Thr
545                 550                 555                 560
Ser Glu Glu Glu Leu Ala Ala Thr Asn Ala Thr Asp Thr Asp Met Trp
            565                 570                 575
Gly Asn Leu Pro Arg His Asp Ser Ser Leu Ser Asn Leu Pro Thr Val
            580                 585                 590
Asp Arg Asn Thr Gly Leu Gly Ala Val Pro Gly Met Val Trp Gln Asn
            595                 600                 605
Arg Asp Ile Tyr Tyr Gln Gly Pro Ile Trp Ala Lys Ile Pro His Thr
            610                 615                 620
Asp Gly His Phe His Pro Ser Pro Leu Ile Gly Phe Gly Leu Lys
625                 630                 635                 640
His Pro Pro Pro Gln Ile Phe Ile Lys Asn Thr Pro Val Pro Ala Asn
            645                 650                 655
Pro Ala Thr Thr Phe Ser Ser Thr Pro Val Asn Ser Phe Ile Thr Gln
            660                 665                 670
Tyr Ser Thr Gly Gln Val Ser Val Gln Ile Asp Trp Glu Ile Gln Lys
            675                 680                 685
Glu Arg Ser Lys Arg Trp Asn Pro Glu Val Gln Phe Thr Ser Asn Tyr
            690                 695                 700
Gly Gln Gln Asn Ser Leu Leu Trp Ala Pro Asp Ala Ala Gly Lys Tyr
705                 710                 715                 720
Thr Glu Pro Arg Ala Ile Gly Thr Arg Tyr Leu Thr His His Leu
            725                 730                 735

<210> SEQ ID NO 16
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 16

Met Ala Ala Asp Gly Tyr Leu Pro Asp Trp Leu Glu Asp Asn Leu Ser
1               5                   10                  15
Glu Gly Val Arg Glu Trp Trp Ala Leu Gln Pro Gly Ala Pro Lys Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
```

```
                50                  55                  60
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                     85                  90                  95

Asp Ala Glu Phe Gln Gln Arg Leu Gln Gly Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Gln Ala Gly Glu Thr Ala Pro Gly Lys Lys Arg
            130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
                180                 185                 190

Ser Asp Asp Ser Glu Met Arg Ala Ala Gly Gly Ala Ala Val Glu
            195                 200                 205

Gly Gly Gln Gly Ala Asp Gly Val Gly Asn Ala Ser Gly Asp Trp His
210                 215                 220

Cys Asp Ser Thr Trp Ser Glu Gly His Val Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
                260                 265                 270

Tyr Phe Asp Phe Asn Arg Phe His Cys His Phe Ser Pro Arg Asp Trp
                275                 280                 285

Gln Arg Leu Ile Asn Asn Asn Trp Gly Met Arg Pro Lys Ala Met Arg
            290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
                340                 345                 350

Ser Leu Pro Pro Phe Pro Asn Asp Val Phe Met Val Pro Gln Tyr Gly
                355                 360                 365

Tyr Cys Gly Leu Val Thr Gly Asn Thr Ser Gln Gln Gln Thr Asp Arg
                370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
                420                 425                 430

Ile Asp Gln Tyr Leu Trp Gly Leu Gln Ser Thr Thr Gly Thr Thr
                435                 440                 445

Leu Asn Ala Gly Thr Ala Thr Thr Asn Phe Thr Lys Leu Arg Pro Thr
                450                 455                 460

Asn Phe Ser Asn Phe Lys Lys Asn Trp Leu Pro Gly Pro Ser Ile Lys
465                 470                 475                 480
```

```
Gln Gln Gly Phe Ser Lys Thr Ala Asn Gln Asn Tyr Phe Ile Pro Ala
            485                 490                 495

Thr Gly Ser Asp Ser Leu Ile Arg Tyr Glu Thr His Ser Thr Leu Asp
        500                 505                 510

Gly Arg Trp Ser Ala Leu Thr Pro Gly Pro Pro Leu Ala Thr Ala Gly
    515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Val Ile Asp Phe Ser Lys Ser Asn Leu Pro Thr Val
            580                 585                 590

Asp Arg Leu Thr His Leu Gly Ala Val Pro Gly Met Val Trp Gln Asn
        595                 600                 605

Arg Asp Ile Tyr Tyr Gln Gly Pro Ile Trp Ala Lys Ile Pro His Thr
    610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
        675                 680                 685

Glu Arg Ser Lys Arg Trp Asn Pro Glu Val Gln Phe Thr Ser Asn Tyr
    690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 17
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 17

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
```

```
                100                 105                 110
Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
            130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Gly Gly Ala Ala Val Glu
            195                 200                 205

Gly Gly Gln Gly Ala Asp Gly Val Gly Asn Ala Ser Gly Asp Trp His
            210                 215                 220

Cys Asp Ser Thr Trp Ser Glu Gly His Val Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
            275                 280                 285

Gln Arg Leu Ile Asn Asn Asn Trp Gly Met Arg Pro Lys Ala Met Arg
            290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
            355                 360                 365

Tyr Cys Gly Leu Val Thr Gly Asn Thr Ser Gln Gln Gln Thr Asp Arg
            370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
            435                 440                 445

Leu Asn Ala Gly Thr Ala Thr Thr Asn Phe Thr Lys Leu Arg Pro Thr
            450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Lys Ile Pro Ala
                485                 490                 495

Thr Gly Ser Asp Ser Leu Ile Lys Tyr Glu Thr His Ser Thr Leu Asp
            500                 505                 510

Gly Arg Trp Ser Ala Leu Thr Pro Gly Pro Pro Met Ala Thr Ala Gly
            515                 520                 525
```

-continued

```
Pro Ala Asp Ser Lys Phe Ser Asn Ser Gln Leu Ile Phe Ala Gly Pro
    530                 535                 540
Lys Gln Asn Gly Asn Thr Ala Thr Val Pro Gly Thr Leu Ile Phe Thr
545                 550                 555                 560
Ser Glu Glu Leu Ala Ala Thr Asn Ala Thr Asp Thr Asp Met Trp
                565                 570                 575
Gly Asn Leu Pro Val Arg Asp Phe Ser Leu Ser Asn Leu Pro Thr Val
                580                 585                 590
Asp Arg Thr Thr Lys Leu Gly Ala Val Pro Gly Met Val Trp Gln Asn
                595                 600                 605
Arg Asp Ile Tyr Tyr Gln Gly Pro Ile Trp Ala Lys Ile Pro His Thr
    610                 615                 620
Asp Gly His Phe His Pro Ser Pro Leu Ile Gly Gly Phe Gly Leu Lys
625                 630                 635                 640
His Pro Pro Pro Gln Ile Phe Ile Lys Asn Thr Pro Val Pro Ala Asn
                645                 650                 655
Pro Ala Thr Thr Phe Ser Ser Thr Pro Val Asn Ser Phe Ile Thr Gln
                660                 665                 670
Tyr Ser Thr Gly Gln Val Ser Val Gln Ile Asp Trp Glu Ile Gln Lys
    675                 680                 685
Glu Arg Ser Lys Arg Trp Asn Pro Glu Val Gln Phe Thr Ser Asn Tyr
690                 695                 700
Gly Gln Gln Asn Ser Leu Leu Trp Ala Pro Asp Ala Ala Gly Lys Tyr
705                 710                 715                 720
Thr Glu Pro Arg Ala Ile Gly Thr Arg Tyr Leu Thr His His Leu
                725                 730                 735
```

<210> SEQ ID NO 18
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 18

```
Met Ala Ala Asp Gly Tyr Leu Pro Asp Trp Leu Glu Asp Asn Leu Ser
1               5                   10                  15
Glu Gly Val Arg Glu Trp Trp Ala Leu Gln Pro Gly Ala Pro Lys Pro
                20                  25                  30
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
        50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Gln Arg Leu Gln Gly Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Gln Ala Gly Glu Thr Ala Pro Gly Lys Lys Arg
    130                 135                 140
Pro Leu Ile Glu Ser Pro Gln Gln Pro Asp Ser Ser Thr Gly Ile Gly
```

-continued

```
                145                 150                 155                 160
        Lys Lys Gly Lys Gln Pro Ala Lys Lys Leu Val Phe Glu Asp Glu
                        165                 170                 175
        Thr Gly Ala Gly Asp Gly Pro Pro Glu Gly Ser Thr Ser Gly Ala Met
                        180                 185                 190
        Ser Asp Asp Ser Glu Met Arg Ala Ala Gly Gly Ala Ala Val Glu
                        195                 200                 205
        Gly Gly Gln Gly Ala Asp Gly Val Gly Asn Ala Ser Gly Asp Trp His
                210                 215                 220
        Cys Asp Ser Thr Trp Ser Glu Gly His Val Thr Thr Ser Thr Arg
        225                 230                 235                 240
        Thr Trp Val Leu Pro Thr Tyr Asn Asn His Leu Tyr Lys Arg Leu Gly
                        245                 250                 255
        Glu Ser Leu Gln Ser Asn Thr Tyr Asn Gly Phe Ser Pro Trp Gly
                        260                 265                 270
        Tyr Phe Asp Phe Asn Arg Phe His Cys His Phe Ser Pro Arg Asp Trp
                        275                 280                 285
        Gln Arg Leu Ile Asn Asn Asn Trp Gly Met Arg Pro Lys Ala Met Arg
                290                 295                 300
        Val Lys Ile Phe Asn Ile Gln Val Lys Glu Val Thr Thr Ser Asn Gly
        305                 310                 315                 320
        Glu Thr Thr Val Ala Asn Asn Leu Thr Ser Thr Val Gln Ile Phe Ala
                        325                 330                 335
        Asp Ser Ser Tyr Glu Leu Pro Tyr Val Met Asp Ala Gly Gln Glu Gly
                        340                 345                 350
        Ser Leu Pro Pro Phe Pro Asn Asp Val Phe Met Val Pro Gln Tyr Gly
                        355                 360                 365
        Tyr Cys Gly Leu Val Thr Gly Asn Thr Ser Gln Gln Gln Thr Asp Arg
                        370                 375                 380
        Asn Ala Phe Tyr Cys Leu Glu Tyr Phe Pro Ser Gln Met Leu Arg Thr
        385                 390                 395                 400
        Gly Asn Asn Phe Glu Ile Thr Tyr Ser Phe Glu Lys Val Pro Phe His
                        405                 410                 415
        Ser Met Tyr Ala His Ser Gln Ser Leu Asp Arg Leu Met Asn Pro Leu
                        420                 425                 430
        Ile Asp Gln Tyr Leu Trp Gly Leu Gln Ser Thr Thr Thr Gly Thr Thr
                        435                 440                 445
        Leu Asn Ala Gly Thr Ala Thr Thr Asn Phe Thr Lys Leu Arg Pro Thr
                450                 455                 460
        Asn Phe Ser Asn Phe Lys Lys Asn Trp Leu Pro Gly Pro Ser Ile Lys
        465                 470                 475                 480
        Gln Gln Gly Phe Ser Lys Thr Ala Asn Gln Asn Tyr Phe Ile Pro Ala
                        485                 490                 495
        Thr Gly Ser Asp Ser Leu Ile Gln Tyr Glu Thr His Ser Thr Leu Asp
                        500                 505                 510
        Gly Arg Trp Ser Ala Leu Thr Pro Gly Pro Met Ala Thr Ala Gly
                        515                 520                 525
        Pro Ala Asp Ser Lys Phe Ser Asn Ser Gln Leu Ile Phe Ala Gly Pro
                        530                 535                 540
        Lys Gln Asn Gly Asn Thr Ala Thr Val Pro Gly Thr Leu Ile Phe Thr
        545                 550                 555                 560
        Ser Glu Glu Glu Leu Ala Ala Thr Asn Ala Thr Asp Thr Asp Met Trp
                        565                 570                 575
```

```
Gly Asn Leu Pro Gly Gly Asp Gln Ser Asn Ser Asn Leu Pro Thr Val
            580                 585                 590

Asp Arg Leu Thr Ala Leu Gly Ala Val Pro Gly Met Val Trp Gln Asn
        595                 600                 605

Arg Asp Ile Tyr Tyr Gln Gly Pro Ile Trp Ala Lys Ile Pro His Thr
    610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
        675                 680                 685

Glu Arg Ser Lys Arg Trp Asn Pro Glu Val Gln Phe Thr Ser Asn Tyr
    690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735
```

<210> SEQ ID NO 19
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 19

```
Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
```

-continued

```
                195                 200                 205
Gly Gly Gln Gly Ala Asp Gly Val Gly Asn Ala Ser Gly Asp Trp His
210                 215                 220
Cys Asp Ser Thr Trp Ser Glu Gly His Val Thr Thr Ser Thr Arg
225                 230                 235                 240
Thr Trp Val Leu Pro Thr Tyr Asn Asn His Leu Tyr Lys Arg Leu Gly
                245                 250                 255
Glu Ser Leu Gln Ser Asn Thr Tyr Asn Gly Phe Ser Thr Pro Trp Gly
                260                 265                 270
Tyr Phe Asp Phe Asn Arg Phe His Cys His Phe Ser Pro Arg Asp Trp
                275                 280                 285
Gln Arg Leu Ile Asn Asn Asn Trp Gly Met Arg Pro Lys Ala Met Arg
                290                 295                 300
Val Lys Ile Phe Asn Ile Gln Val Lys Glu Val Thr Thr Ser Asn Gly
305                 310                 315                 320
Glu Thr Thr Val Ala Asn Asn Leu Thr Ser Thr Val Gln Ile Phe Ala
                325                 330                 335
Asp Ser Ser Tyr Glu Leu Pro Tyr Val Met Asp Ala Gly Gln Glu Gly
                340                 345                 350
Ser Leu Pro Pro Phe Pro Asn Asp Val Phe Met Val Pro Gln Tyr Gly
                355                 360                 365
Tyr Cys Gly Leu Val Thr Gly Asn Thr Ser Gln Gln Thr Asp Arg
370                 375                 380
Asn Ala Phe Tyr Cys Leu Glu Tyr Phe Pro Ser Gln Met Leu Arg Thr
385                 390                 395                 400
Gly Asn Asn Phe Glu Ile Thr Tyr Ser Phe Glu Lys Val Pro Phe His
                405                 410                 415
Ser Met Tyr Ala His Ser Gln Ser Leu Asp Arg Leu Met Asn Pro Leu
                420                 425                 430
Ile Asp Gln Tyr Leu Trp Gly Leu Gln Ser Thr Thr Thr Gly Thr Thr
                435                 440                 445
Leu Asn Ala Gly Thr Ala Thr Thr Asn Phe Thr Lys Leu Arg Pro Thr
450                 455                 460
Asn Phe Ser Asn Phe Lys Lys Asn Trp Leu Pro Gly Pro Ser Ile Lys
465                 470                 475                 480
Gln Gln Gly Phe Ser Lys Thr Ala Asn Gln Asn Tyr Glu Met Pro Ala
                485                 490                 495
Thr Gly Ser Asp Ser Leu Ile Ile Tyr Glu Thr His Ser Thr Leu Asp
                500                 505                 510
Gly Arg Trp Ser Ala Leu Thr Pro Gly Pro Pro Phe Ala Thr Ala Gly
                515                 520                 525
Pro Ala Asp Ser Lys Phe Ser Asn Ser Gln Leu Ile Phe Ala Gly Pro
                530                 535                 540
Lys Gln Asn Gly Asn Thr Ala Thr Val Pro Gly Thr Leu Ile Phe Thr
545                 550                 555                 560
Ser Glu Glu Glu Leu Ala Ala Thr Asn Ala Thr Asp Thr Asp Val Trp
                565                 570                 575
Gly Asn Leu Pro Ser Gly Asp His Ser Gln Ser Asn Leu Pro Thr Val
                580                 585                 590
Asp Arg Pro Thr Met Leu Gly Ala Val Pro Gly Met Val Trp Gln Asn
                595                 600                 605
Arg Asp Ile Tyr Tyr Gln Gly Pro Ile Trp Ala Lys Ile Pro His Thr
                610                 615                 620
```

```
Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
            645                 650                 655

Pro Ala Thr Thr Phe Ile Ser Thr Pro Val Asn Ser Phe Ile Thr Gln
            660                 665                 670

Tyr Ser Thr Gly Gln Val Ser Val His Ile Asp Trp Glu Ile Gln Lys
        675                 680                 685

Glu Arg Ser Lys Arg Trp Asn Pro Glu Val Gln Phe Thr Ser Asp Tyr
    690                 695                 700

Gly Gln His Ser Ser Leu Leu Trp Ala Pro Asp Ala Ala Gly Lys Tyr
705                 710                 715                 720

Thr Glu Pro Thr Ala Ile Gly Thr Arg Tyr Leu Thr His His Leu
                725                 730                 735
```

<210> SEQ ID NO 20
<211> LENGTH: 734
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 20

```
Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
```

```
                     245                 250                 255
Glu Ser Leu Gln Ser Asn Thr Tyr Asn Gly Phe Ser Thr Pro Trp Gly
                260                 265                 270

Tyr Phe Asp Phe Asn Arg Phe His Cys His Phe Ser Pro Arg Asp Trp
            275                 280                 285

Gln Arg Leu Ile Asn Asn Asn Trp Gly Met Arg Pro Lys Ala Met Arg
        290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
        435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Asp Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
            530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
        610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670
```

```
Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
        690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 21
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 21

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
```

```
            290                 295                 300
Val Lys Ile Phe Asn Ile Gln Val Lys Glu Val Thr Thr Ser Asn Gly
305                 310                 315                 320
Glu Thr Thr Val Ala Asn Asn Leu Thr Ser Thr Val Gln Ile Phe Ala
                    325                 330                 335
Asp Ser Ser Tyr Glu Leu Pro Tyr Val Met Asp Ala Gly Gln Glu Gly
                340                 345                 350
Ser Leu Pro Pro Phe Pro Asn Asp Val Phe Met Val Pro Gln Tyr Gly
            355                 360                 365
Tyr Cys Gly Leu Val Thr Gly Asn Thr Ser Gln Gln Gln Thr Asp Arg
        370                 375                 380
Asn Ala Phe Tyr Cys Leu Glu Tyr Phe Pro Ser Gln Met Leu Arg Thr
385                 390                 395                 400
Gly Asn Asn Phe Glu Ile Thr Tyr Ser Phe Glu Lys Val Pro Phe His
                    405                 410                 415
Ser Met Tyr Ala His Ser Gln Ser Leu Asp Arg Leu Met Asn Pro Leu
                420                 425                 430
Ile Asp Gln Tyr Leu Trp Gly Leu Gln Ser Thr Thr Thr Gly Thr Thr
            435                 440                 445
Leu Asn Ala Gly Thr Ala Thr Thr Asn Phe Thr Lys Leu Arg Pro Thr
        450                 455                 460
Asn Phe Ser Asn Phe Lys Lys Asn Trp Leu Pro Gly Pro Ser Ile Lys
465                 470                 475                 480
Gln Gln Gly Phe Ser Lys Thr Ala Asn Gln Asn Tyr Ile Ile Pro Ala
                    485                 490                 495
Thr Gly Ser Asp Ser Leu Ile Thr Tyr Glu Thr His Ser Thr Leu Asp
                500                 505                 510
Gly Arg Trp Ser Ala Leu Thr Pro Gly Pro Val Ala Thr Ala Gly
            515                 520                 525
Pro Ala Asp Ser Lys Phe Ser Asn Ser Gln Leu Ile Phe Ala Gly Pro
        530                 535                 540
Lys Gln Asn Gly Asn Thr Ala Thr Val Pro Gly Thr Leu Ile Phe Thr
545                 550                 555                 560
Ser Glu Glu Glu Leu Ala Ala Thr Asn Ala Thr Asp Thr Asp Met Trp
                    565                 570                 575
Gly Asn Leu Pro Phe Asn Asp Asp Ser Ser Asn Leu Pro Thr Val
                580                 585                 590
Asp Arg Ser Thr Phe Leu Gly Ala Val Pro Gly Met Val Trp Gln Asn
            595                 600                 605
Arg Asp Ile Tyr Tyr Gln Gly Pro Ile Trp Ala Lys Ile Pro His Thr
        610                 615                 620
Asp Gly His Phe His Pro Ser Pro Leu Ile Gly Gly Phe Gly Leu Lys
625                 630                 635                 640
His Pro Pro Pro Gln Ile Phe Ile Lys Asn Thr Pro Val Pro Ala Asn
                    645                 650                 655
Pro Ala Thr Thr Phe Ser Ser Thr Pro Val Asn Ser Phe Ile Thr Gln
                660                 665                 670
Tyr Ser Thr Gly Gln Val Ser Val Gln Ile Asp Trp Glu Ile Gln Lys
            675                 680                 685
Glu Arg Ser Lys Arg Trp Asn Pro Glu Val Gln Phe Thr Ser Asn Tyr
        690                 695                 700
Gly Gln Gln Asn Ser Leu Leu Trp Ala Pro Asp Ala Ala Gly Lys Tyr
705                 710                 715                 720
```

Thr Glu Pro Arg Ala Ile Gly Thr Arg Tyr Leu Thr His His Leu
            725                 730                 735

<210> SEQ ID NO 22
<211> LENGTH: 733
<212> TYPE: PRT
<213> ORGANISM: adeno-associated virus 11

<400> SEQUENCE: 22

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp Gln
65                  70                  75                  80

Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Gly Ile Gly Lys
145                 150                 155                 160

Lys Gly Lys Gln Pro Ala Arg Lys Arg Leu Asn Phe Glu Glu Asp Thr
            165                 170                 175

Gly Ala Gly Asp Gly Pro Pro Glu Gly Ser Asp Thr Ser Ala Met Ser
        180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
            245                 250                 255

Thr Ser Ser Ser Asn Thr Tyr Asn Gly Phe Ser Thr Pro Trp Gly Tyr
        260                 265                 270

Phe Asp Phe Asn Arg Phe His Cys His Phe Ser Pro Arg Asp Trp Gln
    275                 280                 285

Arg Leu Ile Asn Asn Asn Trp Gly Leu Arg Pro Lys Ala Met Arg Val
        290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr

```
                355                 360                 365
Cys Gly Ile Val Thr Gly Glu Asn Gln Asn Gln Thr Asp Arg Asn Ala
            370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 23
<211> LENGTH: 742
<212> TYPE: PRT
<213> ORGANISM: adeno-associated virus 12

<400> SEQUENCE: 23
```

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Gly Arg Gly Leu Val Leu Pro
            35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65              70                  75                  80
Lys Gln Leu Glu Gln Gly Asp Asn Pro Tyr Leu Lys Tyr Asn His Ala
            85                  90                  95
Asp Ala Glu Phe Gln Gln Arg Leu Ala Thr Asp Thr Ser Phe Gly Gly
            100                 105                 110
Asn Leu Gly Arg Ala Val Phe Gln Ala Lys Lys Arg Ile Leu Glu Pro
        115                 120                 125
Leu Gly Leu Val Glu Glu Gly Val Lys Thr Ala Pro Gly Lys Lys Arg
    130                 135                 140
Pro Leu Glu Lys Thr Pro Asn Arg Pro Thr Asn Pro Asp Ser Gly Lys
145                 150                 155                 160
Ala Pro Ala Lys Lys Lys Gln Lys Asp Gly Glu Pro Ala Asp Ser Ala
            165                 170                 175
Arg Arg Thr Leu Asp Phe Glu Asp Ser Gly Ala Gly Asp Gly Pro Pro
            180                 185                 190
Glu Gly Ser Ser Ser Gly Glu Met Ser His Asp Ala Glu Met Arg Ala
        195                 200                 205
Ala Pro Gly Gly Asn Ala Val Glu Ala Gly Gln Gly Ala Asp Gly Val
    210                 215                 220
Gly Asn Ala Ser Gly Asp Trp His Cys Asp Ser Thr Trp Ser Glu Gly
225                 230                 235                 240
Arg Val Thr Thr Thr Ser Thr Arg Thr Trp Val Leu Pro Thr Tyr Asn
            245                 250                 255
Asn His Leu Tyr Leu Arg Ile Gly Thr Thr Ala Asn Ser Asn Thr Tyr
            260                 265                 270
Asn Gly Phe Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Leu Arg Pro Lys Ser Met Arg Val Lys Ile Phe Asn Ile Gln Val
305                 310                 315                 320
Lys Glu Val Thr Thr Ser Asn Gly Glu Thr Thr Val Ala Asn Asn Leu
            325                 330                 335
Thr Ser Thr Val Gln Ile Phe Ala Asp Ser Thr Tyr Glu Leu Pro Tyr
            340                 345                 350
Val Met Asp Ala Gly Gln Glu Gly Ser Phe Pro Pro Phe Pro Asn Asp
        355                 360                 365
Val Phe Met Val Pro Gln Tyr Gly Tyr Cys Gly Val Val Thr Gly Lys
    370                 375                 380
Asn Gln Asn Gln Thr Asp Arg Asn Ala Phe Tyr Cys Leu Glu Tyr Phe
385                 390                 395                 400
Pro Ser Gln Met Leu Arg Thr Gly Asn Asn Phe Glu Val Ser Tyr Gln
            405                 410                 415
Phe Glu Lys Val Pro Phe His Ser Met Tyr Ala His Ser Gln Ser Leu
```

```
            420                 425                 430
Asp Arg Met Met Asn Pro Leu Leu Asp Gln Tyr Leu Trp His Leu Gln
            435                 440                 445

Ser Thr Thr Thr Gly Asn Ser Leu Asn Gln Gly Thr Ala Thr Thr Thr
            450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
            485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
            515                 520                 525

Pro Pro Met Ala Thr Ala Gly Ala Gly Asp Ser Asp Phe Ser Asn Ser
            530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Glu Ile Ala Thr Thr Asn
            565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
            595                 600                 605

Pro Gly Met Val Trp Gln Asn Arg Asp Ile Tyr Tyr Gln Gly Pro Ile
            610                 615                 620

Trp Ala Lys Val Pro His Thr Asp Gly His Phe His Pro Ser Pro Leu
625                 630                 635                 640

Met Gly Gly Phe Gly Leu Lys His Pro Pro Pro Gln Ile Phe Ile Lys
            645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
            675                 680                 685

Ile Asp Trp Glu Ile Gln Lys Glu His Ser Lys Arg Trp Asn Pro Glu
            690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
            725                 730                 735

Phe Leu Thr His His Leu
            740

<210> SEQ ID NO 24
<211> LENGTH: 736
<212> TYPE: PRT
<213> ORGANISM: Bovine adeno-associated virus

<400> SEQUENCE: 24

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
            20                  25                  30

Ala Asn Gln Gln Lys Gln Asp Asn Ala Arg Gly Leu Val Leu Pro Gly
            35                  40                  45
```

```
Tyr Lys Tyr Leu Gly Pro Gly Asn Gly Leu Asp Lys Gly Asp Pro Val
     50              55                  60

Asn Phe Ala Asp Glu Val Ala Arg Glu His Asp Leu Ser Tyr Gln Lys
 65              70                  75                      80

Gln Leu Glu Ala Gly Asp Asn Pro Tyr Leu Lys Tyr Asn His Ala Asp
                 85                  90                  95

Ala Glu Phe Gln Glu Lys Leu Ala Ser Asp Thr Ser Phe Gly Gly Asn
                100                 105             110

Leu Gly Lys Ala Val Phe Gln Ala Lys Lys Arg Ile Leu Glu Pro Leu
            115                 120             125

Gly Leu Val Glu Thr Pro Asp Lys Thr Ala Pro Ala Ala Lys Lys Arg
130                 135                 140

Pro Leu Glu Gln Ser Pro Gln Glu Pro Asp Ser Ser Gly Val Gly
145                 150                 155             160

Lys Lys Gly Lys Gln Pro Ala Arg Lys Arg Leu Asn Phe Asp Asp Glu
                165                 170             175

Pro Gly Ala Gly Asp Gly Pro Pro Glu Gly Pro Ser Ser Gly Ala
                180                 185             190

Met Ser Thr Glu Thr Glu Met Arg Ala Ala Gly Gly Asn Gly Gly
                195                 200             205

Asp Ala Gly Gln Gly Ala Glu Gly Val Gly Asn Ala Ser Gly Asp Trp
210                 215                 220

His Cys Asp Ser Thr Trp Ser Glu Ser His Val Thr Thr Ser Thr
225                 230                 235             240

Arg Thr Trp Val Leu Pro Thr Tyr Asn Asn His Leu Tyr Leu Arg Leu
                245                 250                 255

Gly Ser Ser Asn Ala Ser Asp Thr Phe Asn Gly Phe Ser Thr Pro Trp
            260                 265                 270

Gly Tyr Phe Asp Phe Asn Arg Phe His Cys His Phe Ser Pro Arg Asp
            275                 280                 285

Trp Gln Arg Leu Ile Asn Asn His Trp Gly Leu Arg Pro Lys Ser Met
290                 295                 300

Gln Val Arg Ile Phe Asn Ile Gln Val Lys Glu Val Thr Thr Ser Asn
305                 310                 315                 320

Gly Glu Thr Thr Val Ser Asn Asn Leu Thr Ser Thr Val Gln Ile Phe
                325                 330                 335

Ala Asp Ser Thr Tyr Glu Leu Pro Tyr Val Met Asp Ala Gly Gln Glu
                340                 345                 350

Gly Ser Leu Pro Pro Phe Pro Asn Asp Val Phe Met Val Pro Gln Tyr
            355                 360                 365

Gly Tyr Cys Gly Leu Val Thr Gly Gly Ser Ser Gln Asn Gln Thr Asp
            370                 375                 380

Arg Asn Ala Phe Tyr Cys Leu Glu Tyr Phe Pro Ser Gln Met Leu Arg
385                 390                 395                 400

Thr Gly Asn Asn Phe Glu Met Val Tyr Lys Phe Glu Asn Val Pro Phe
                405                 410                 415

His Ser Met Tyr Ala His Ser Gln Ser Leu Asp Arg Leu Met Asn Pro
                420                 425                 430

Leu Leu Asp Gln Tyr Leu Trp Glu Leu Gln Ser Thr Thr Ser Gly Gly
            435                 440                 445

Thr Leu Asn Gln Gly Asn Ser Ala Thr Asn Phe Ala Lys Leu Thr Lys
450                 455                 460

Thr Asn Phe Ser Gly Tyr Arg Lys Asn Trp Leu Pro Gly Pro Met Met
```

```
                465                 470                 475                 480
Lys Gln Gln Arg Phe Ser Lys Thr Ala Ser Gln Asn Tyr Lys Ile Pro
                    485                 490                 495

Gln Gly Arg Asn Asn Ser Leu Leu His Tyr Glu Thr Arg Thr Thr Leu
                500                 505                 510

Asp Gly Arg Trp Ser Asn Phe Ala Pro Gly Thr Ala Met Ala Thr Ala
            515                 520                 525

Ala Asn Asp Ala Thr Asp Phe Ser Gln Ala Gln Leu Ile Phe Ala Gly
        530                 535                 540

Pro Asn Ile Thr Gly Asn Thr Thr Asp Ala Asn Asn Leu Met Phe
545                 550                 555                 560

Thr Ser Glu Asp Glu Leu Arg Ala Thr Asn Pro Arg Asp Thr Asp Leu
                565                 570                 575

Phe Gly His Leu Ala Thr Asn Gln Gln Asn Ala Thr Thr Val Pro Thr
                580                 585                 590

Val Asp Asp Val Asp Gly Val Gly Val Tyr Pro Gly Met Val Trp Gln
            595                 600                 605

Asp Arg Asp Ile Tyr Tyr Gln Gly Pro Ile Trp Ala Lys Ile Pro His
        610                 615                 620

Thr Asp Gly His Phe His Pro Ser Pro Leu Ile Gly Gly Phe Gly Leu
625                 630                 635                 640

Lys Ser Pro Pro Gln Ile Phe Ile Lys Asn Thr Pro Val Pro Ala
                645                 650                 655

Asn Pro Ala Thr Thr Phe Ser Pro Ala Arg Ile Asn Ser Phe Ile Thr
                660                 665                 670

Gln Tyr Ser Thr Gly Gln Val Ala Val Lys Ile Glu Trp Glu Ile Gln
            675                 680                 685

Lys Glu Arg Ser Lys Arg Trp Asn Pro Glu Val Gln Phe Thr Ser Asn
        690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735

<210> SEQ ID NO 25
<211> LENGTH: 733
<212> TYPE: PRT
<213> ORGANISM: adeno-associated virus rh32

<400> SEQUENCE: 25

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

```
Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Leu Glu Ser Pro Gln Glu Pro Asp Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Ser Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Gly Lys Val Pro Phe His Ser Met
                405                 410                 415

Tyr Ala Tyr Ser Gln Ser Pro Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Leu Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
```

```
                530                535                540
Thr Gly Asn Thr Thr Thr Ser Ala Asn Asn Leu Leu Phe Thr Ser Glu
545                550                555                560

Glu Glu Ile Ala Ala Thr Asn Pro Arg Asp Thr Asp Met Phe Gly Gln
                565                570                575

Ile Ala Asp Asn Asn Gln Asn Ala Thr Thr Ala Pro Ile Thr Gly Asn
                580                585                590

Val Thr Ala Met Gly Val Leu Pro Gly Met Val Trp Gln Asn Arg Asp
                595                600                605

Ile Tyr Tyr Gln Gly Pro Ile Trp Ala Lys Ile Pro His Ala Asp Gly
610                615                620

His Phe His Pro Ser Pro Leu Ile Gly Gly Phe Gly Leu Lys His Pro
625                630                635                640

Pro Pro Gln Ile Phe Ile Lys Asn Thr Pro Val Pro Ala Asn Pro Ala
                645                650                655

Thr Thr Phe Thr Ala Ala Arg Val Asp Ser Phe Ile Thr Gln Tyr Ser
                660                665                670

Thr Gly Gln Val Ala Val Gln Ile Glu Trp Glu Ile Glu Lys Glu Arg
                675                680                685

Ser Lys Arg Trp Asn Pro Glu Val Gln Phe Thr Ser Asn Tyr Gly Asn
690                695                700

Gln Ser Ser Met Leu Trp Ala Pro Asp Thr Thr Gly Lys Tyr Thr Glu
705                710                715                720

Pro Arg Val Ile Gly Ser Arg Tyr Leu Thr Asn His Leu
                725                730

<210> SEQ ID NO 26
<211> LENGTH: 733
<212> TYPE: PRT
<213> ORGANISM: adeno-associated virus rh33

<400> SEQUENCE: 26

Met Ala Ala Asp Gly Tyr Leu Pro Asp Trp Leu Glu Asp Asn Leu Ser
1               5                  10                 15

Glu Gly Ile Arg Glu Trp Trp Asp Leu Lys Pro Gly Ala Pro Lys Leu
                20                 25                 30

Lys Ala Asn Gln Gln Lys Gln Asp Asp Gly Arg Gly Leu Val Leu Pro
                35                 40                 45

Gly Tyr Lys Tyr Leu Gly Pro Phe His Gly Leu Asp Lys Gly Glu Pro
50                 55                 60

Val Asn Ala Ala Asp Ala Ala Ala Leu Glu His Asp Lys Ala Tyr Asp
65                 70                 75                 80

Gln Gln Leu Lys Ala Gly Asp Asn Pro Tyr Leu Arg Tyr Asn His Ala
                85                 90                 95

Asp Ala Glu Phe Gln Glu Arg Leu Gln Glu Asp Thr Ser Phe Gly Gly
                100                105                110

Asn Leu Gly Arg Ala Val Phe Gln Ala Lys Lys Arg Val Leu Glu Pro
                115                120                125

Leu Gly Leu Val Glu Glu Gly Ala Lys Thr Ala Pro Gly Lys Lys Arg
130                135                140

Pro Leu Glu Ser Pro Gln Glu Pro Asp Ser Ser Ser Gly Ile Gly Lys
145                150                155                160

Lys Gly Lys Gln Pro Ala Lys Lys Arg Leu Asn Phe Glu Glu Asp Thr
                165                170                175
```

```
Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Gly Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
```

```
            595                 600                 605
Ile Tyr Tyr Gln Gly Pro Ile Trp Ala Lys Ile Pro His Ala Asp Gly
610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                    645                 650                 655

Thr Thr Phe Thr Ala Ala Arg Val Asp Ser Phe Ile Thr Gln Tyr Ser
                660                 665                 670

Thr Gly Gln Val Ala Val Gln Ile Glu Trp Glu Ile Glu Lys Glu Arg
            675                 680                 685

Ser Lys Arg Arg Asn Pro Glu Val Gln Phe Thr Ser Asn Tyr Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730
```

<210> SEQ ID NO 27
<211> LENGTH: 733
<212> TYPE: PRT
<213> ORGANISM: adeno-associated virus rh34

<400> SEQUENCE: 27

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Glu Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240
```

```
Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Thr Ala Tyr Asn Phe Glu Lys Val Pro Phe His Ser Met
                405                 410                 415

Tyr Ala His Ser Gln Ser Leu Asp Gly Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Tyr Pro Ala
                645                 650                 655

Thr Thr Phe Thr Ala Ala Arg Val Asp Ser Phe Ile Thr Gln Tyr Ser
```

```
            660                 665                 670
Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Cys Gly Asn
        690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 28
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 28

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
            165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285
```

```
Gln Arg Leu Ile Asn Asn Asn Trp Gly Met Arg Pro Lys Ala Met Arg
    290                 295                 300
Val Lys Ile Phe Asn Ile Gln Val Lys Glu Val Thr Thr Ser Asn Gly
305                 310                 315                 320
Glu Thr Thr Val Ala Asn Asn Leu Thr Ser Thr Val Gln Ile Phe Ala
                325                 330                 335
Asp Ser Ser Tyr Glu Leu Pro Tyr Val Met Asp Ala Gly Gln Glu Gly
            340                 345                 350
Ser Leu Pro Pro Phe Pro Asn Asp Val Phe Met Val Pro Gln Tyr Gly
        355                 360                 365
Tyr Cys Gly Leu Val Thr Gly Asn Thr Ser Gln Gln Gln Thr Asp Arg
    370                 375                 380
Asn Ala Phe Tyr Cys Leu Glu Tyr Phe Pro Ser Gln Met Leu Arg Thr
385                 390                 395                 400
Gly Asn Asn Phe Glu Ile Thr Tyr Ser Phe Glu Lys Val Pro Phe His
                405                 410                 415
Ser Met Tyr Ala His Ser Gln Ser Leu Asp Arg Leu Met Asn Pro Leu
            420                 425                 430
Ile Asp Gln Tyr Leu Trp Gly Leu Gln Ser Thr Thr Thr Gly Thr Thr
        435                 440                 445
Leu Asn Ala Gly Thr Ala Thr Thr Asn Phe Thr Lys Leu Arg Pro Thr
    450                 455                 460
Asn Phe Ser Asn Phe Lys Lys Asn Trp Leu Pro Gly Pro Ser Ile Lys
465                 470                 475                 480
Gln Gln Gly Phe Ser Lys Thr Ala Asn Gln Asn Tyr Glu Ile Pro Ala
                485                 490                 495
Thr Gly Ser Asp Ser Leu Ile Glu Tyr Glu Thr His Ser Thr Leu Asp
            500                 505                 510
Gly Arg Trp Ser Ala Leu Thr Pro Gly Pro Pro Met Ala Thr Ala Gly
        515                 520                 525
Pro Ala Asp Ser Lys Phe Ser Asn Ser Gln Leu Ile Phe Ala Gly Pro
    530                 535                 540
Lys Gln Asn Gly Asn Thr Ala Thr Val Pro Gly Thr Leu Ile Phe Thr
545                 550                 555                 560
Ser Glu Glu Glu Leu Ala Ala Thr Asn Ala Thr Asp Thr Asp Met Trp
                565                 570                 575
Gly Asn Leu Pro Gly Gly Asp Gln Ser Ser Asn Leu Pro Thr Val
            580                 585                 590
Asp Arg Leu Thr Ala Leu Gly Ala Val Pro Gly Met Val Trp Gln Asn
        595                 600                 605
Arg Asp Ile Tyr Tyr Gln Gly Pro Ile Trp Ala Lys Ile Pro His Thr
    610                 615                 620
Asp Gly His Phe His Pro Ser Pro Leu Ile Gly Gly Phe Gly Leu Lys
625                 630                 635                 640
His Pro Pro Pro Gln Ile Phe Ile Lys Asn Thr Pro Val Pro Ala Asn
                645                 650                 655
Pro Ala Thr Thr Phe Ser Ser Thr Pro Val Asn Ser Phe Ile Thr Gln
            660                 665                 670
Tyr Ser Thr Gly Gln Val Ser Val Gln Ile Asp Trp Glu Ile Gln Lys
        675                 680                 685
Glu Arg Ser Lys Arg Trp Asn Pro Glu Val Gln Phe Thr Ser Asn Tyr
    690                 695                 700
Gly Gln Gln Asn Ser Leu Leu Trp Ala Pro Asp Ala Ala Gly Lys Tyr
```

```
                705                 710                 715                 720

Thr Glu Pro Arg Ala Ile Gly Thr Arg Tyr Leu Thr His His Leu
                725                 730                 735

<210> SEQ ID NO 29
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 29

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
145                 150                 155                 160

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
    290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335
```

-continued

Asp Ser Ser Tyr Glu Leu Pro Tyr Val Met Asp Ala Gly Gln Gly
                340                 345                 350

Ser Leu Pro Pro Phe Pro Asn Asp Val Phe Met Val Pro Gln Tyr Gly
            355                 360                 365

Tyr Cys Gly Leu Val Thr Gly Asn Thr Ser Gln Gln Gln Thr Asp Arg
        370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
        435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Glu Ile Pro Ala
                485                 490                 495

Thr Gly Ser Asp Ser Leu Ile Glu Tyr Glu Thr His Ser Thr Leu Asp
            500                 505                 510

Gly Arg Trp Ser Ala Leu Thr Pro Gly Pro Met Ala Thr Ala Gly
        515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Leu Ala Ala Thr Asn Ala Thr Asp Thr Asp Met Trp
                565                 570                 575

Gly Asn Leu Pro Gly Gly Asp Gln Ser Ser Ser Asn Leu Pro Val Val
            580                 585                 590

Arg Gly Leu Arg Ala Leu Gly Ala Val Pro Gly Met Val Trp Gln Asn
        595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
            660                 665                 670

Tyr Ser Thr Gly Gln Val Ser Val Gln Ile Asp Trp Glu Ile Gln Lys
        675                 680                 685

Glu Arg Ser Lys Arg Trp Asn Pro Glu Val Gln Phe Thr Ser Asn Tyr
690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 30
<211> LENGTH: 735
<212> TYPE: PRT

<213> ORGANISM: Artificial
<220> FEATURE:
<223> OTHER INFORMATION: Recombinant adeno-associated virus 4 capsid protein sequence

<400> SEQUENCE: 30

```
Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
    130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
        195                 200                 205

Gly Gly Gln Gly Ala Asp Gly Val Gly Asn Ala Ser Gly Asp Trp His
    210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
    290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
    370                 375                 380
```

```
Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
            405                 410                 415

Ser Met Tyr Ala His Ser Gln Ser Leu Asp Arg Leu Met Asn Pro Leu
                420                 425                 430

Ile Asp Gln Tyr Leu Trp Gly Leu Gln Ser Thr Thr Gly Thr Thr
        435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Glu Ile Pro Ala
                485                 490                 495

Thr Gly Ser Asp Ser Leu Ile Glu Tyr Glu Thr His Ser Thr Leu Asp
                500                 505                 510

Gly Arg Trp Ser Ala Leu Thr Pro Gly Pro Pro Met Ala Thr Ala Gly
                515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Gly Gly Asp Gln Ser Ser Asn Leu Pro Val Val
                580                 585                 590

Asn Arg Leu Ser Ala Leu Gly Ala Val Pro Gly Met Val Trp Gln Asn
            595                 600                 605

Arg Asp Ile Tyr Tyr Gln Gly Pro Ile Trp Ala Lys Ile Pro His Thr
                610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
                660                 665                 670

Tyr Ser Thr Gly Gln Val Ser Val Gln Ile Asp Trp Glu Ile Gln Lys
        675                 680                 685

Glu Arg Ser Lys Arg Trp Asn Pro Glu Val Gln Phe Thr Ser Asn Tyr
    690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 31
<211> LENGTH: 735
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 31

Met Ala Ala Asp Gly Tyr Leu Pro Asp Trp Leu Glu Asp Asn Leu Ser
1               5                   10                  15
```

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
 50                  55                  60

Val Asn Ala Ala Asp Ala Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
            130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Ala Gly Gly Ala Ala Val Glu
            195                 200                 205

Gly Gly Gln Gly Ala Asp Gly Val Gly Asn Ala Ser Gly Asp Trp His
            210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
            275                 280                 285

Gln Arg Leu Ile Asn Asn Asn Trp Gly Met Arg Pro Lys Ala Met Arg
            290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
            355                 360                 365

Tyr Cys Gly Leu Val Thr Gly Asn Thr Ser Gln Gln Gln Thr Asp Arg
            370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

```
Ile Asp Gln Tyr Leu Trp Gly Leu Gln Ser Thr Thr Thr Gly Thr Thr
            435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Glu Ile Pro Ala
                485                 490                 495

Thr Gly Ser Asp Ser Leu Ile Glu Tyr Glu Thr His Ser Thr Leu Asp
                500                 505                 510

Gly Arg Trp Ser Ala Leu Thr Pro Gly Pro Pro Met Ala Thr Ala Gly
            515                 520                 525

Pro Ala Asp Ser Lys Phe Ser Asn Ser Gln Leu Ile Phe Ala Gly Pro
530                 535                 540

Lys Gln Asn Gly Asn Thr Ala Thr Val Pro Gly Thr Leu Ile Phe Thr
545                 550                 555                 560

Ser Glu Glu Glu Leu Ala Ala Thr Asn Ala Thr Asp Thr Asp Met Trp
                565                 570                 575

Gly Asn Leu Pro Gly Gly Asp Gln Ser Ser Ser Asn Leu Pro Pro Val
            580                 585                 590

Met Gly Leu Gly Ala Leu Gly Ala Val Pro Gly Met Val Trp Gln Asn
            595                 600                 605

Arg Asp Ile Tyr Tyr Gln Gly Pro Ile Trp Ala Lys Ile Pro His Thr
610                 615                 620

Asp Gly His Phe His Pro Ser Pro Leu Ile Gly Gly Phe Gly Leu Lys
625                 630                 635                 640

His Pro Pro Pro Gln Ile Phe Ile Lys Asn Thr Pro Val Pro Ala Asn
                645                 650                 655

Pro Ala Thr Thr Phe Ser Ser Thr Pro Val Asn Ser Phe Ile Thr Gln
                660                 665                 670

Tyr Ser Thr Gly Gln Val Ser Val Gln Ile Asp Trp Glu Ile Gln Lys
            675                 680                 685

Glu Arg Ser Lys Arg Trp Asn Pro Glu Val Gln Phe Thr Ser Asn Tyr
690                 695                 700

Gly Gln Gln Asn Ser Leu Leu Trp Ala Pro Asp Ala Ala Gly Lys Tyr
705                 710                 715                 720

Thr Glu Pro Arg Ala Ile Gly Thr Arg Tyr Leu Thr His His Leu
                725                 730                 735

<210> SEQ ID NO 32
<211> LENGTH: 736
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 32

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Gln Arg Leu Gln Gly Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gln Ala Gly Glu Thr Ala Pro Gly Lys Lys Arg
130                 135                 140

Pro Leu Ile Glu Ser Pro Gln Gln Pro Asp Ser Ser Thr Gly Ile Gly
145                 150                 155                 160

Lys Lys Gly Lys Gln Pro Ala Lys Lys Lys Leu Val Phe Glu Asp Glu
                165                 170                 175

Thr Gly Ala Gly Asp Gly Pro Pro Glu Gly Ser Thr Ser Gly Ala Met
            180                 185                 190

Ser Asp Asp Ser Glu Met Arg Ala Ala Gly Gly Ala Ala Val Glu
        195                 200                 205

Gly Gly Gln Gly Ala Asp Gly Val Gly Asn Ala Ser Gly Asp Trp His
210                 215                 220

Cys Asp Ser Thr Trp Ser Glu Gly His Val Thr Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
            340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
            420                 425                 430

Ile Asp Gln Tyr Leu Trp Gly Leu Gln Ser Thr Thr Thr Gly Thr Thr
        435                 440                 445

Leu Asn Ala Gly Thr Ala Thr Thr Asn Phe Thr Lys Leu Arg Pro Thr
450                 455                 460

Asn Phe Ser Asn Phe Lys Lys Asn Trp Leu Pro Gly Pro Ser Ile Lys
465                 470                 475                 480
```

```
Gln Gln Gly Phe Ser Lys Thr Ala Asn Gln Asn Tyr Glu Ile Pro Ala
                485                 490                 495

Thr Gly Ser Asp Ser Leu Ile Glu Tyr Glu Thr His Ser Thr Leu Asp
            500                 505                 510

Gly Arg Trp Ser Ala Leu Thr Pro Gly Pro Pro Met Ala Thr Ala Gly
        515                 520                 525

Pro Ala Asp Ser Lys Phe Ser Asn Ser Gln Leu Ile Phe Ala Gly Pro
    530                 535                 540

Lys Gln Asn Gly Asn Thr Ala Thr Val Pro Gly Thr Leu Ile Phe Thr
545                 550                 555                 560

Ser Glu Glu Leu Ala Ala Thr Asn Ala Thr Asp Thr Asp Met Trp
                565                 570                 575

Gly Asn Leu Pro Gly Gly Asp Gln Ser Arg Val Asp Arg Leu Pro Thr
                580                 585                 590

Val Asp Arg Leu Thr Ala Leu Gly Ala Val Pro Gly Met Val Trp Gln
            595                 600                 605

Asn Arg Asp Ile Tyr Tyr Gln Gly Pro Ile Trp Ala Lys Ile Pro His
        610                 615                 620

Thr Asp Gly His Phe His Pro Ser Pro Leu Ile Gly Phe Gly Leu
625                 630                 635                 640

Lys His Pro Pro Gln Ile Phe Ile Lys Asn Thr Pro Val Pro Ala
                645                 650                 655

Asn Pro Ala Thr Thr Phe Ser Ser Thr Pro Val Asn Ser Phe Ile Thr
                660                 665                 670

Gln Tyr Ser Thr Gly Gln Val Ser Val Gln Ile Asp Trp Glu Ile Gln
            675                 680                 685

Lys Glu Arg Ser Lys Arg Trp Asn Pro Glu Val Gln Phe Thr Ser Asn
690                 695                 700

Tyr Gly Gln Gln Asn Ser Leu Leu Trp Ala Pro Asp Ala Ala Gly Lys
705                 710                 715                 720

Tyr Thr Glu Pro Arg Ala Ile Gly Thr Arg Tyr Leu Thr His His Leu
                725                 730                 735

<210> SEQ ID NO 33
<211> LENGTH: 736
<212> TYPE: PRT
<213> ORGANISM: Artificial
<220> FEATURE:
<223> OTHER INFORMATION: Recombinant adeno-associated virus 4 capsid
      protein sequence

<400> SEQUENCE: 33

Met Ala Ala Asp Gly Tyr Leu Pro Asp Trp Leu Glu Asp Asn Leu Ser
1               5                   10                  15

Glu Gly Val Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Gln Arg Leu Gln Gly Asp Thr Ser Phe Gly Gly
            100                 105                 110
```

```
Asn Leu Gly Arg Ala Val Phe Gln Ala Lys Lys Arg Val Leu Glu Pro
            115                 120                 125

Leu Gly Leu Val Glu Gln Ala Gly Glu Thr Ala Pro Gly Lys Lys Arg
        130                 135                 140

Pro Leu Ile Glu Ser Pro Gln Pro Asp Ser Ser Thr Gly Ile Gly
145                 150                 155                 160

Lys Lys Gly Lys Gln Pro Ala Lys Lys Leu Val Phe Glu Asp Glu
                165                 170                 175

Thr Gly Ala Gly Asp Gly Pro Pro Glu Gly Ser Thr Ser Gly Ala Met
                180                 185                 190

Ser Asp Asp Ser Glu Met Arg Ala Ala Gly Gly Ala Ala Val Glu
        195                 200                 205

Gly Gly Gln Gly Ala Asp Gly Val Gly Asn Ala Ser Gly Asp Trp His
        210                 215                 220

Cys Asp Ser Thr Trp Ser Glu Gly His Val Thr Thr Ser Thr Arg
225                 230                 235                 240

Thr Trp Val Leu Pro Thr Tyr Asn Asn His Leu Tyr Lys Arg Leu Gly
                245                 250                 255

Glu Ser Leu Gln Ser Asn Thr Tyr Asn Gly Phe Ser Thr Pro Trp Gly
        260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Met Arg Pro Lys Ala Met Arg
        290                 295                 300

Val Lys Ile Phe Asn Ile Gln Val Lys Glu Val Thr Thr Ser Asn Gly
305                 310                 315                 320

Glu Thr Thr Val Ala Asn Asn Leu Thr Ser Thr Val Gln Ile Phe Ala
                325                 330                 335

Asp Ser Ser Tyr Glu Leu Pro Tyr Val Met Asp Ala Gly Gln Glu Gly
                340                 345                 350

Ser Leu Pro Pro Phe Pro Asn Asp Val Phe Met Val Pro Gln Tyr Gly
        355                 360                 365

Tyr Cys Gly Leu Val Thr Gly Asn Thr Ser Gln Gln Gln Thr Asp Arg
        370                 375                 380

Asn Ala Phe Tyr Cys Leu Glu Tyr Phe Pro Ser Gln Met Leu Arg Thr
385                 390                 395                 400

Gly Asn Asn Phe Glu Ile Thr Tyr Ser Phe Glu Lys Val Pro Phe His
                405                 410                 415

Ser Met Tyr Ala His Ser Gln Ser Leu Asp Arg Leu Met Asn Pro Leu
        420                 425                 430

Ile Asp Gln Tyr Leu Trp Gly Leu Gln Ser Thr Thr Thr Gly Thr Thr
        435                 440                 445

Leu Asn Ala Gly Thr Ala Thr Thr Asn Phe Thr Lys Leu Arg Pro Thr
        450                 455                 460

Asn Phe Ser Asn Phe Lys Lys Asn Trp Leu Pro Gly Pro Ser Ile Lys
465                 470                 475                 480

Gln Gln Gly Phe Ser Lys Thr Ala Asn Gln Asn Tyr Glu Ile Pro Ala
                485                 490                 495

Thr Gly Ser Asp Ser Leu Ile Glu Tyr Glu Thr His Ser Thr Leu Asp
                500                 505                 510

Gly Arg Trp Ser Ala Leu Thr Pro Gly Pro Pro Met Ala Thr Ala Gly
        515                 520                 525
```

```
Pro Ala Asp Ser Lys Phe Ser Asn Ser Gln Leu Ile Phe Ala Gly Pro
    530                 535                 540

Lys Gln Asn Gly Asn Thr Ala Thr Val Pro Gly Thr Leu Ile Phe Thr
545                 550                 555                 560

Ser Glu Glu Leu Ala Ala Thr Asn Ala Thr Asp Thr Asp Met Trp
                565                 570                 575

Gly Asn Leu Pro Gly Gly Asp Gln Ser Arg Ala Leu Arg Leu Pro Thr
                580                 585                 590

Val Asp Arg Leu Thr Ala Leu Gly Ala Val Pro Gly Met Val Trp Gln
            595                 600                 605

Asn Arg Asp Ile Tyr Tyr Gln Gly Pro Ile Trp Ala Lys Ile Pro His
    610                 615                 620

Thr Asp Gly His Phe His Pro Ser Pro Leu Ile Gly Gly Phe Gly Leu
625                 630                 635                 640

Lys His Pro Pro Pro Gln Ile Phe Ile Lys Asn Thr Pro Val Pro Ala
                645                 650                 655

Asn Pro Ala Thr Thr Phe Ser Ser Thr Pro Val Asn Ser Phe Ile Thr
                660                 665                 670

Gln Tyr Ser Thr Gly Gln Val Ser Val Gln Ile Asp Trp Glu Ile Gln
            675                 680                 685

Lys Glu Arg Ser Lys Arg Trp Asn Pro Glu Val Gln Phe Thr Ser Asn
690                 695                 700

Tyr Gly Gln Gln Asn Ser Leu Leu Trp Ala Pro Asp Ala Ala Gly Lys
705                 710                 715                 720

Tyr Thr Glu Pro Arg Ala Ile Gly Thr Arg Tyr Leu Thr His His Leu
                725                 730                 735

<210> SEQ ID NO 34
<211> LENGTH: 20
<212> TYPE: DNA
<213> ORGANISM: Artificial
<220> FEATURE:
<223> OTHER INFORMATION: PCR primer sequence

<400> SEQUENCE: 34
cgtcaatggg tggagtattt                                            20

<210> SEQ ID NO 35
<211> LENGTH: 21
<212> TYPE: DNA
<213> ORGANISM: Artificial
<220> FEATURE:
<223> OTHER INFORMATION: PCR primer sequence

<400> SEQUENCE: 35
gcgatgacta atacgtagat g                                          21

<210> SEQ ID NO 36
<211> LENGTH: 150
<212> TYPE: PRT
<213> ORGANISM: Artificial
<220> FEATURE:
<223> OTHER INFORMATION: adeno-associated virus 4

<400> SEQUENCE: 36

Lys Ile Pro Ala Thr Gly Ser Asp Ser Leu Ile Lys Tyr Glu Thr His
1               5                   10                  15

Ser Thr Leu Asp Gly Arg Trp Ser Ala Leu Thr Pro Gly Pro Pro Met
            20                  25                  30
```

```
Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
 50                  55                  60

Leu Ile Phe Thr Ser Glu Glu Glu Leu Ala Ala Thr Asn Ala Thr Asp
 65                  70                  75                  80

Thr Asp Met Trp Gly Asn Leu Pro Gly Gly Asp Gln Ser Asn Ser Asn
                 85                  90                  95

Leu Pro Thr Val Asp Arg Leu Thr Ala Leu Gly Ala Val Pro Gly Met
                100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
        130                 135                 140

Phe Gly Leu Lys His Pro
145                 150

<210> SEQ ID NO 37
<211> LENGTH: 150
<212> TYPE: PRT
<213> ORGANISM: Artificial
<220> FEATURE:
<223> OTHER INFORMATION: adeno-associated virus 4_1

<400> SEQUENCE: 37

Leu Ile Pro Ala Thr Gly Ser Asp Ser Leu Ile Cys Tyr Glu Thr His
 1               5                  10                  15

Ser Thr Leu Asp Gly Arg Trp Ser Ala Leu Thr Pro Gly Pro Pro Gly
                 20                  25                  30

Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
 50                  55                  60

Leu Ile Phe Thr Ser Glu Glu Glu Leu Ala Ala Thr Asn Ala Thr Asp
 65                  70                  75                  80

Thr Asp Met Trp Gly Asn Leu Pro Asp His Asp Leu Ser Leu Ser Asn
                 85                  90                  95

Leu Pro Thr Val Asp Arg Asp Thr Trp Leu Gly Ala Val Pro Gly Met
                100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
        130                 135                 140

Phe Gly Leu Lys His Pro
145                 150

<210> SEQ ID NO 38
<211> LENGTH: 150
<212> TYPE: PRT
<213> ORGANISM: Artificial
<220> FEATURE:
<223> OTHER INFORMATION: adeno-associated virus 4_2

<400> SEQUENCE: 38

Gly Ile Pro Ala Thr Gly Ser Asp Ser Leu Ile Lys Tyr Glu Thr His
 1               5                  10                  15

Ser Thr Leu Asp Gly Arg Trp Ser Ala Leu Thr Pro Gly Pro Pro Ile
                 20                  25                  30
```

```
Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
            50                  55                  60

Leu Ile Phe Thr Ser Glu Glu Leu Ala Ala Thr Asn Ala Thr Asp
65                  70                  75                  80

Thr Asp Met Trp Gly Asn Leu Pro Leu Tyr Asp Ala Ser Ser Asn
                85                  90                  95

Leu Pro Thr Val Asp Arg Leu Thr Leu Leu Gly Ala Val Pro Gly Met
            100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
            130                 135                 140

Phe Gly Leu Lys His Pro
145                 150

<210> SEQ ID NO 39
<211> LENGTH: 150
<212> TYPE: PRT
<213> ORGANISM: Artificial
<220> FEATURE:
<223> OTHER INFORMATION: adeno-associated virus 4_3

<400> SEQUENCE: 39

Thr Ile Pro Ala Thr Gly Ser Asp Ser Leu Ile Thr Tyr Glu Thr His
1               5                   10                  15

Ser Thr Leu Asp Gly Arg Trp Ser Ala Leu Thr Pro Gly Pro Pro Gly
            20                  25                  30

Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
            50                  55                  60

Leu Ile Phe Thr Ser Glu Glu Leu Ala Ala Thr Asn Ala Thr Asp
65                  70                  75                  80

Thr Asp Met Trp Gly Asn Leu Pro Arg Val Asp Thr Ser Ala Ser Asn
                85                  90                  95

Leu Pro Thr Val Asp Arg Tyr Thr Asn Leu Gly Ala Val Pro Gly Met
            100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
            130                 135                 140

Phe Gly Leu Lys His Pro
145                 150

<210> SEQ ID NO 40
<211> LENGTH: 150
<212> TYPE: PRT
<213> ORGANISM: Artificial
<220> FEATURE:
<223> OTHER INFORMATION: adeno-associated virus 4_10

<400> SEQUENCE: 40

Ser Ile Pro Ala Thr Gly Ser Asp Ser Leu Ile Lys Tyr Glu Thr His
1               5                   10                  15

Ser Thr Leu Asp Gly Arg Trp Ser Ala Leu Thr Pro Gly Pro Pro Phe
```

```
            20                  25                  30
Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
        50                  55                  60

Leu Ile Phe Thr Ser Glu Glu Glu Leu Ala Ala Thr Asn Ala Thr Asp
65                  70                  75                  80

Thr Asp Met Trp Gly Asn Leu Pro Asp Tyr Asp Ser Ser Leu Ser Asn
                85                  90                  95

Leu Pro Thr Val Asp Arg Asp Thr Thr Leu Gly Ala Val Pro Gly Met
            100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
        130                 135                 140

Phe Gly Leu Lys His Pro
145                 150

<210> SEQ ID NO 41
<211> LENGTH: 150
<212> TYPE: PRT
<213> ORGANISM: Artificial
<220> FEATURE:
<223> OTHER INFORMATION: adeno-associated virus 4_13

<400> SEQUENCE: 41

Ser Ile Pro Ala Thr Gly Ser Asp Ser Leu Ile Trp Tyr Glu Thr His
1               5                   10                  15

Ser Thr Leu Asp Gly Arg Trp Ser Ala Leu Thr Pro Gly Pro Pro Cys
            20                  25                  30

Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
        50                  55                  60

Leu Ile Phe Thr Ser Glu Glu Glu Leu Ala Ala Thr Asn Ala Thr Asp
65                  70                  75                  80

Thr Asp Met Trp Gly Asn Leu Pro Gln Gly Asp Ser Ser Leu Ser Asn
                85                  90                  95

Leu Pro Thr Val Asp Arg Met Thr Val Leu Gly Ala Val Pro Gly Met
            100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
        130                 135                 140

Phe Gly Leu Lys His Pro
145                 150

<210> SEQ ID NO 42
<211> LENGTH: 150
<212> TYPE: PRT
<213> ORGANISM: Artificial
<220> FEATURE:
<223> OTHER INFORMATION: adeno-associated virus 4_14

<400> SEQUENCE: 42

Leu Ile Pro Ala Thr Gly Ser Asp Ser Leu Ile Arg Tyr Glu Thr His
1               5                   10                  15
```

Ser Thr Leu Asp Gly Arg Trp Ser Ala Leu Thr Pro Gly Pro Pro Met
            20                  25                  30

Ala Thr Ala Gly Pro Ala Asp Ser Lys Phe Ser Asn Ser Gln Leu Ile
        35                  40                  45

Phe Ala Gly Pro Lys Gln Asn Gly Asn Thr Ala Thr Val Pro Gly Thr
50                  55                  60

Leu Ile Phe Thr Ser Glu Glu Leu Ala Ala Thr Asn Ala Thr Asp
65                  70                  75                  80

Thr Asp Met Trp Gly Asn Leu Pro Phe Arg Asp Leu Ser Ser Asn
                85                  90                  95

Leu Pro Thr Val Asp Arg Ser Thr Pro Leu Gly Ala Val Pro Gly Met
            100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
        130                 135                 140

Phe Gly Leu Lys His Pro
145                 150

<210> SEQ ID NO 43
<211> LENGTH: 150
<212> TYPE: PRT
<213> ORGANISM: Artificial
<220> FEATURE:
<223> OTHER INFORMATION: adeno-associated virus 4_20

<400> SEQUENCE: 43

Cys Ile Pro Ala Thr Gly Ser Asp Ser Leu Ile Arg Tyr Glu Thr His
1               5                   10                  15

Ser Thr Leu Asp Gly Arg Trp Ser Ala Leu Thr Pro Gly Pro Pro Leu
            20                  25                  30

Ala Thr Ala Gly Pro Ala Asp Ser Lys Phe Ser Asn Ser Gln Leu Ile
        35                  40                  45

Phe Ala Gly Pro Lys Gln Asn Gly Asn Thr Ala Thr Val Pro Gly Thr
50                  55                  60

Leu Ile Phe Thr Ser Glu Glu Leu Ala Ala Thr Asn Ala Thr Asp
65                  70                  75                  80

Thr Asp Met Trp Gly Asn Leu Pro Tyr Lys Asp Ser Ser Arg Ser Asn
                85                  90                  95

Leu Pro Thr Val Asp Arg Glu Thr Ser Leu Gly Ala Val Pro Gly Met
            100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
        130                 135                 140

Phe Gly Leu Lys His Pro
145                 150

<210> SEQ ID NO 44
<211> LENGTH: 150
<212> TYPE: PRT
<213> ORGANISM: Artificial
<220> FEATURE:
<223> OTHER INFORMATION: adeno-associated virus 4_22

<400> SEQUENCE: 44

Ile Ile Pro Ala Thr Gly Ser Asp Ser Leu Ile Tyr Tyr Glu Thr His
1               5                   10                  15

```
Ser Thr Leu Asp Gly Arg Trp Ser Ala Leu Thr Pro Gly Pro Pro Arg
            20                  25                  30

Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
 50                  55                  60

Leu Ile Phe Thr Ser Glu Glu Leu Ala Ala Thr Asn Ala Thr Asp
 65                  70                  75                  80

Thr Asp Met Trp Gly Asn Leu Pro Trp Ile Asp Asn Ser Arg Ser Asn
                 85                  90                  95

Leu Pro Thr Val Asp Arg Pro Thr Ser Leu Gly Ala Val Pro Gly Met
            100                 105                 110

Val Trp Gln Asn Lys Asn Ile Tyr Tyr Gln Gly Pro Ile Trp Ala Lys
                115                 120                 125

Ile Pro His Thr Asp Gly His Phe His Pro Ser Pro Leu Ile Gly Gly
            130                 135                 140

Phe Gly Leu Lys His Pro
145                 150

<210> SEQ ID NO 45
<211> LENGTH: 150
<212> TYPE: PRT
<213> ORGANISM: Artificial
<220> FEATURE:
<223> OTHER INFORMATION: adeno-associated virus 4_24

<400> SEQUENCE: 45

Cys Ile Gly Ala Pro Arg Glu Tyr Ser Leu Ile Val Tyr Glu Thr His
 1                   5                  10                  15

Ser Thr Leu Asp Gly Glu Trp Ser Ala Val Thr Pro Gly Pro Pro Asp
            20                  25                  30

Ala Arg Gly Gly Pro Ala Asp Ser Lys Phe Ser Asn Ser Gln Leu Ile
            35                  40                  45

Phe Gly Gly Pro Lys Gln Asn Gly Asn Thr Ala Thr Val Pro Gly Thr
 50                  55                  60

Leu Ile Phe Thr Ser Glu Glu Leu Ala Ala Thr Asn Ala Thr Asp
 65                  70                  75                  80

Thr Asp Met Trp Gly Asn Leu Pro Gly Phe Asp Phe Ser Phe Ser Ser
                 85                  90                  95

Leu Pro Thr Val Asp Arg Asp Thr Ile Leu Gly Gly Val Pro Gly Met
            100                 105                 110

Val Trp Gln Asn Lys Tyr Ile Tyr Tyr Gln Gly Pro Ile Trp Ala Lys
                115                 120                 125

Ile Pro His Thr Asp Gly His Phe His Pro Ser Pro Gly Ile Gly Gly
            130                 135                 140

Phe Gly Leu Lys His Pro
145                 150

<210> SEQ ID NO 46
<211> LENGTH: 150
<212> TYPE: PRT
<213> ORGANISM: Artificial
<220> FEATURE:
<223> OTHER INFORMATION: adeno-associated virus 4_26

<400> SEQUENCE: 46

Met Ile Pro Ala Thr Gly Ser Asp Ser Leu Ile Trp Tyr Glu Thr Gly
```

```
                1               5                  10                 15
            Arg Ala Leu Glu Gly Arg Trp Gly Ala Val Arg Ala Gly Pro Pro Asp
                            20                  25                  30

Asp Ser Ala Gly Pro Ala Asp Ser Lys Val Val Asn Ile Leu Val Ile
                            35                  40                  45

Phe Gly Gly Pro Lys Gln Asn Gly Asn Thr Ala Thr Val Pro Gly Thr
                            50                  55                  60

Leu Ile Phe Thr Ser Glu Glu Leu Ala Ala Thr Asn Ala Thr Asp
            65                  70                  75                  80

Thr Asp Val Trp Gly Asn Leu Pro Ile Thr Asp His Asn Pro Ser Asn
                            85                  90                  95

Leu Pro Thr Val Asp Arg Ala Thr Phe Leu Gly Val Ala Gly Met
                            100                 105                 110

Val Trp Gln Asn Arg Asp Ile Tyr Tyr Gln Gly Pro Ile Trp Ala Lys
                            115                 120                 125

Ile Pro His Thr Asp Gly His Phe His Pro Ser Pro Leu Ile Gly Gly
                            130                 135                 140

Phe Gly Leu Lys His Pro
            145                 150

<210> SEQ ID NO 47
<211> LENGTH: 150
<212> TYPE: PRT
<213> ORGANISM: Artificial
<220> FEATURE:
<223> OTHER INFORMATION: adeno-associated virus 4_27

<400> SEQUENCE: 47

Gly Ile Pro Ala Thr Gly Ser Asp Ser Leu Ile Ile Tyr Glu Thr His
1               5                  10                  15

Ser Thr Leu Asp Gly Arg Trp Ser Ala Leu Thr Pro Gly Pro Pro Arg
                20                  25                  30

Ala Thr Ala Gly Pro Ala Asp Ser Lys Phe Ser Asn Ser Gln Leu Ile
                35                  40                  45

Phe Ala Gly Pro Lys Gln Asn Gly Asn Thr Ala Thr Val Pro Gly Thr
                50                  55                  60

Leu Ile Phe Thr Ser Glu Glu Leu Ala Ala Thr Asn Ala Thr Asp
65                  70                  75                  80

Thr Asp Met Trp Gly Asn Leu Pro Gly Gly Asp Gln Ser Asn Ser Asn
                85                  90                  95

Leu Pro Thr Val Asp Arg Leu Thr Ala Leu Gly Ala Val Pro Gly Met
                100                 105                 110

Val Trp Gln Asn Arg Asp Ile Tyr Tyr Gln Gly Pro Ile Trp Ala Lys
                115                 120                 125

Ile Pro His Thr Asp Gly His Phe His Pro Ser Pro Leu Ile Gly Gly
                130                 135                 140

Phe Gly Leu Lys His Pro
145                 150

<210> SEQ ID NO 48
<211> LENGTH: 150
<212> TYPE: PRT
<213> ORGANISM: Artificial
<220> FEATURE:
<223> OTHER INFORMATION: adeno-associated virus 4_28

<400> SEQUENCE: 48
```

```
Val Ile Pro Ala Thr Glu Ser Asp Ser Leu Ile Tyr Tyr Glu Thr His
1               5                   10                  15

Ser Thr Leu Asp Gly Arg Trp Ser Ala Leu Thr Pro Gly Pro Pro Tyr
                20                  25                  30

Ala Thr Ala Gly Pro Ala Asp Ser Lys Phe Ser Asn Ser Gln Leu Ile
                35                  40                  45

Phe Ala Gly Pro Lys Gln Asn Gly Asn Thr Ala Thr Val Pro Gly Thr
    50                  55                  60

Leu Ile Phe Thr Ser Glu Glu Leu Ala Ala Thr Asn Ala Thr Asp
65                  70                  75                  80

Thr Asp Met Trp Gly Asn Leu Pro Pro Arg Asp Asp Ser Thr Ser Asn
                85                  90                  95

Leu Pro Thr Val Asp Arg Lys Thr Tyr Leu Gly Ala Val Pro Gly Met
                100                 105                 110

Val Trp Gln Asn Arg Asp Ile Tyr Tyr Gln Gly Pro Ile Trp Ala Lys
                115                 120                 125

Ile Pro His Thr Asp Gly His Phe His Pro Ser Pro Leu Ile Gly Gly
            130                 135                 140

Phe Gly Leu Lys His Pro
145                 150

<210> SEQ ID NO 49
<211> LENGTH: 150
<212> TYPE: PRT
<213> ORGANISM: Artificial
<220> FEATURE:
<223> OTHER INFORMATION: adeno-associated virus 4_31

<400> SEQUENCE: 49

Tyr Ile Pro Ala Thr Gly Ser Asp Ser Leu Ile Ile Tyr Glu Thr His
1               5                   10                  15

Ser Thr Leu Asp Gly Arg Trp Ser Ala Leu Thr Pro Gly Pro Pro Ile
                20                  25                  30

Ala Thr Ala Gly Pro Ala Asp Ser Lys Phe Ser Asn Ser Gln Leu Ile
                35                  40                  45

Phe Ala Gly Pro Lys Gln Asn Gly Asn Thr Ala Thr Val Pro Gly Thr
    50                  55                  60

Leu Ile Phe Thr Ser Glu Glu Glu Leu Ala Ala Thr Asn Ser Thr Asp
65                  70                  75                  80

Thr Asp Met Trp Gly Asn Leu Pro Thr Asp Asp Ser Arg Ser Asn
                85                  90                  95

Leu Pro Thr Val Asp Arg Met Thr Leu Leu Gly Ala Val Pro Gly Met
                100                 105                 110

Val Trp Gln Asn Arg Asp Ile Tyr Tyr Gln Gly Pro Ile Trp Ala Lys
                115                 120                 125

Ile Pro His Thr Asp Gly His Phe His Pro Ser Pro Leu Ile Gly Gly
            130                 135                 140

Phe Gly Leu Lys His Pro
145                 150

<210> SEQ ID NO 50
<211> LENGTH: 150
<212> TYPE: PRT
<213> ORGANISM: Artificial
<220> FEATURE:
<223> OTHER INFORMATION: adeno-associated virus 4_39

<400> SEQUENCE: 50
```

-continued

```
His Ile Pro Ala Thr Gly Ser Asp Ser Leu Ile Tyr Tyr Glu Thr His
1               5                   10                  15

Ser Thr Leu Asp Gly Arg Trp Ser Ala Leu Thr Pro Gly Pro Pro Ser
                20                  25                  30

Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
        50                  55                  60

Leu Ile Phe Thr Ser Glu Glu Glu Leu Ala Ala Thr Asn Ala Thr Asp
65                  70                  75                  80

Thr Asp Met Trp Gly Asn Leu Pro Arg Arg Asp Ser Ser Val Ser Asn
                85                  90                  95

Leu Pro Thr Val Asp Arg Tyr Thr Asp Leu Gly Ala Val Pro Gly Met
                100                 105                 110

Val Trp Gln Asn Arg Asp Ile Tyr Tyr Gln Gly Pro Ile Trp Ala Lys
                115                 120                 125

Ile Pro His Thr Asp Gly His Phe His Pro Ser Pro Leu Ile Gly Gly
        130                 135                 140

Phe Gly Leu Lys His Pro
145                 150
```

<210> SEQ ID NO 51
<211> LENGTH: 150
<212> TYPE: PRT
<213> ORGANISM: Artificial
<220> FEATURE:
<223> OTHER INFORMATION: adeno-associated virus 4_40

<400> SEQUENCE: 51

```
Tyr Ile Pro Ala Thr Gly Ser Asp Ser Leu Ile Leu Tyr Glu Thr His
1               5                   10                  15

Ser Thr Leu Asp Gly Arg Trp Ser Ala Leu Thr Pro Gly Pro Pro Met
                20                  25                  30

Ala Thr Ala Gly Pro Ala Asp Ser Lys Phe Ser Asn Ser Gln Leu Ile
            35                  40                  45

Phe Ala Gly Pro Lys Gln Asn Gly Asn Thr Ala Thr Val Pro Gly Thr
        50                  55                  60

Leu Ile Phe Thr Ser Glu Glu Glu Leu Ala Ala Thr Asn Ala Thr Asp
65                  70                  75                  80

Thr Asp Met Trp Gly Asn Leu Pro Gly Gly Asp Gln Ser Asn Ser Asn
                85                  90                  95

Leu Pro Thr Val Asp Arg Leu Thr Ala Leu Gly Ala Val Pro Gly Met
                100                 105                 110

Val Trp Gln Asn Arg Asp Ile Tyr Tyr Gln Gly Pro Ile Trp Ala Lys
                115                 120                 125

Ile Pro His Thr Asp Gly His Phe His Pro Ser Pro Leu Ile Gly Gly
        130                 135                 140

Phe Gly Leu Lys His Pro
145                 150
```

<210> SEQ ID NO 52
<211> LENGTH: 150
<212> TYPE: PRT
<213> ORGANISM: Artificial
<220> FEATURE:
<223> OTHER INFORMATION: adeno-associated virus 4_43

<400> SEQUENCE: 52

Ser Ile Pro Ala Thr Gly Ser Asp Ser Leu Ile Ser Tyr Glu Thr His
1               5                   10                  15

Ser Thr Leu Asp Gly Arg Trp Ser Ala Leu Thr Pro Gly Pro Pro Arg
            20                  25                  30

Ala Thr Ala Gly Pro Ala Asp Ser Lys Phe Ser Asn Ser Gln Leu Ile
        35                  40                  45

Phe Ala Gly Pro Lys Gln Asn Gly Asn Thr Ala Thr Val Pro Gly Thr
    50                  55                  60

Leu Ile Phe Thr Ser Glu Glu Glu Leu Ala Ala Thr Asn Ala Thr Asp
65                  70                  75                  80

Thr Asp Met Trp Gly Asn Leu Pro Arg His Asp Ser Ser Leu Ser Asn
                85                  90                  95

Leu Pro Thr Val Asp Arg Asn Thr Gly Leu Gly Ala Val Pro Gly Met
            100                 105                 110

Val Trp Gln Asn Arg Asp Ile Tyr Tyr Gln Gly Pro Ile Trp Ala Lys
                115                 120                 125

Ile Pro His Thr Asp Gly His Phe His Pro Ser Pro Leu Ile Gly Gly
            130                 135                 140

Phe Gly Leu Lys His Pro
145                 150

<210> SEQ ID NO 53
<211> LENGTH: 150
<212> TYPE: PRT
<213> ORGANISM: Artificial
<220> FEATURE:
<223> OTHER INFORMATION: adeno-associated virus 4_49

<400> SEQUENCE: 53

Lys Ile Pro Ala Thr Gly Ser Asp Ser Leu Ile Lys Tyr Glu Thr His
1               5                   10                  15

Ser Thr Leu Asp Gly Arg Trp Ser Ala Leu Thr Pro Gly Pro Pro Met
            20                  25                  30

Ala Thr Ala Gly Pro Ala Asp Ser Lys Phe Ser Asn Ser Gln Leu Ile
        35                  40                  45

Phe Ala Gly Pro Lys Gln Asn Gly Asn Thr Ala Thr Val Pro Gly Thr
    50                  55                  60

Leu Ile Phe Thr Ser Glu Glu Glu Leu Ala Ala Thr Asn Ala Thr Asp
65                  70                  75                  80

Thr Asp Met Trp Gly Asn Leu Pro Val Arg Asp Phe Ser Leu Ser Asn
                85                  90                  95

Leu Pro Thr Val Asp Arg Thr Thr Lys Leu Gly Ala Val Pro Gly Met
            100                 105                 110

Val Trp Gln Asn Arg Asp Ile Tyr Tyr Gln Gly Pro Ile Trp Ala Lys
                115                 120                 125

Ile Pro His Thr Asp Gly His Phe His Pro Ser Pro Leu Ile Gly Gly
            130                 135                 140

Phe Gly Leu Lys His Pro
145                 150

<210> SEQ ID NO 54
<211> LENGTH: 150
<212> TYPE: PRT
<213> ORGANISM: Artificial
<220> FEATURE:
<223> OTHER INFORMATION: adeno-associated virus 4_60

<400> SEQUENCE: 54

Phe Ile Pro Ala Thr Gly Ser Asp Ser Leu Ile Gln Tyr Glu Thr His
1               5                   10                  15

Ser Thr Leu Asp Gly Arg Trp Ser Ala Leu Thr Pro Gly Pro Pro Met
            20                  25                  30

Ala Thr Ala Gly Pro Ala Asp Ser Lys Phe Ser Asn Ser Gln Leu Ile
        35                  40                  45

Phe Ala Gly Pro Lys Gln Asn Gly Asn Thr Ala Thr Val Pro Gly Thr
    50                  55                  60

Leu Ile Phe Thr Ser Glu Glu Leu Ala Ala Thr Asn Ala Thr Asp
65                  70                  75                  80

Thr Asp Met Trp Gly Asn Leu Pro Gly Gly Asp Gln Ser Asn Ser Asn
                85                  90                  95

Leu Pro Thr Val Asp Arg Leu Thr Ala Leu Gly Ala Val Pro Gly Met
            100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
        130                 135                 140

Phe Gly Leu Lys His Pro
145                 150

<210> SEQ ID NO 55
<211> LENGTH: 150
<212> TYPE: PRT
<213> ORGANISM: Artificial
<220> FEATURE:
<223> OTHER INFORMATION: adeno-associated virus 4_63

<400> SEQUENCE: 55

Glu Met Pro Ala Thr Gly Ser Asp Ser Leu Ile Ile Tyr Glu Thr His
1               5                   10                  15

Ser Thr Leu Asp Gly Arg Trp Ser Ala Leu Thr Pro Gly Pro Pro Phe
            20                  25                  30

Ala Thr Ala Gly Pro Ala Asp Ser Lys Phe Ser Asn Ser Gln Leu Ile
        35                  40                  45

Phe Ala Gly Pro Lys Gln Asn Gly Asn Thr Ala Thr Val Pro Gly Thr
    50                  55                  60

Leu Ile Phe Thr Ser Glu Glu Leu Ala Ala Thr Asn Ala Thr Asp
65                  70                  75                  80

Thr Asp Val Trp Gly Asn Leu Pro Ser Gly Asp His Ser Gln Ser Asn
                85                  90                  95

Leu Pro Thr Val Asp Arg Pro Thr Met Leu Gly Ala Val Pro Gly Met
            100                 105                 110

Val Trp Gln Asn Arg Asp Ile Tyr Tyr Gln Gly Pro Ile Trp Ala Lys
            115                 120                 125

Ile Pro His Thr Asp Gly His Phe His Pro Ser Pro Leu Ile Gly Gly
        130                 135                 140

Phe Gly Leu Lys His Pro
145                 150

<210> SEQ ID NO 56
<211> LENGTH: 150
<212> TYPE: PRT
<213> ORGANISM: Artificial
<220> FEATURE:

<223> OTHER INFORMATION: adeno-associated virus 4_80

<400> SEQUENCE: 56

Asp Ile Pro Ala Thr Gly Ser Asp Ser Leu Ile Lys Tyr Glu Thr His
1               5                   10                  15

Ser Thr Leu Asp Gly Arg Trp Ser Ala Leu Thr Pro Gly Pro Pro Met
            20                  25                  30

Ala Thr Ala Gly Pro Ala Asp Ser Lys Phe Ser Asn Ser Gln Leu Ile
        35                  40                  45

Phe Ala Gly Pro Lys Gln Asn Gly Asn Thr Ala Thr Val Pro Gly Thr
    50                  55                  60

Leu Ile Phe Thr Ser Glu Glu Glu Leu Ala Ala Thr Asn Ala Thr Asp
65                  70                  75                  80

Thr Asp Met Trp Gly Asn Leu Pro Gly Gly Asp Gln Ser Asn Ser Asn
                85                  90                  95

Leu Pro Thr Val Asp Arg Leu Thr Ala Leu Gly Ala Val Pro Gly Met
            100                 105                 110

Val Trp Gln Asn Arg Asp Ile Tyr Tyr Gln Gly Pro Ile Trp Ala Lys
        115                 120                 125

Ile Pro His Thr Asp Gly His Phe His Pro Ser Pro Leu Ile Gly Gly
    130                 135                 140

Phe Gly Leu Lys His Pro
145             150

<210> SEQ ID NO 57
<211> LENGTH: 150
<212> TYPE: PRT
<213> ORGANISM: Artificial
<220> FEATURE:
<223> OTHER INFORMATION: adeno-associated virus 4_90

<400> SEQUENCE: 57

Ile Ile Pro Ala Thr Gly Ser Asp Ser Leu Ile Thr Tyr Glu Thr His
1               5                   10                  15

Ser Thr Leu Asp Gly Arg Trp Ser Ala Leu Thr Pro Gly Pro Pro Val
            20                  25                  30

Ala Thr Ala Gly Pro Ala Asp Ser Lys Phe Ser Asn Ser Gln Leu Ile
        35                  40                  45

Phe Ala Gly Pro Lys Gln Asn Gly Asn Thr Ala Thr Val Pro Gly Thr
    50                  55                  60

Leu Ile Phe Thr Ser Glu Glu Glu Leu Ala Ala Thr Asn Ala Thr Asp
65                  70                  75                  80

Thr Asp Met Trp Gly Asn Leu Pro Phe Asn Asp Asp Ser Ser Ser Asn
                85                  90                  95

Leu Pro Thr Val Asp Arg Ser Thr Phe Leu Gly Ala Val Pro Gly Met
            100                 105                 110

Val Trp Gln Asn Arg Asp Ile Tyr Tyr Gln Gly Pro Ile Trp Ala Lys
        115                 120                 125

Ile Pro His Thr Asp Gly His Phe His Pro Ser Pro Leu Ile Gly Gly
    130                 135                 140

Phe Gly Leu Lys His Pro
145             150